(12) United States Patent
Yen et al.

(10) Patent No.: US 11,211,568 B2
(45) Date of Patent: Dec. 28, 2021

(54) COMPOUND FOR ORGANIC ELECTROLUMINESCENCE DEVICE USING THE SAME

(71) Applicants: Feng-Wen Yen, Taipei (TW);
Wen-Feng Hsiao, Nantou (TW)

(72) Inventors: Feng-Wen Yen, Taipei (TW);
Wen-Feng Hsiao, Nantou (TW)

(73) Assignee: LUMINESCENCE TECHNOLOGY CORP., Hsin-Chu (TW)

(*) Notice: Subject to any disclaimer, the term of this patent is extended or adjusted under 35 U.S.C. 154(b) by 395 days.

(21) Appl. No.: 16/252,740

(22) Filed: Jan. 21, 2019

(65) Prior Publication Data

US 2020/0235311 A1  Jul. 23, 2020

(51) Int. Cl.
*H01L 51/00* (2006.01)
*C07D 495/04* (2006.01)
*C09K 11/06* (2006.01)
*H01L 51/50* (2006.01)

(52) U.S. Cl.
CPC ........ *H01L 51/0072* (2013.01); *C07D 495/04* (2013.01); *C09K 11/06* (2013.01); *H01L 51/0067* (2013.01); *H01L 51/0071* (2013.01); *H01L 51/0073* (2013.01); *C09K 2211/1018* (2013.01); *H01L 51/5016* (2013.01); *H01L 2251/5376* (2013.01)

(58) Field of Classification Search
None
See application file for complete search history.

(56) References Cited

U.S. PATENT DOCUMENTS

2015/0144898 A1*  5/2015  Dai ............... H01L 51/0058
                                                                    257/40
2018/0006242 A1   1/2018  Jang et al.

FOREIGN PATENT DOCUMENTS

KR   10-2017-0139895   * 12/2017

OTHER PUBLICATIONS

Machine English translation of Lee et al. (KR-10-2017-0139895). Apr. 19, 2021.*

* cited by examiner

*Primary Examiner* — Jay Yang

(57) ABSTRACT

The present invention discloses an organic compound and an organic electroluminescence device using the organic compound as a material in the light emitting layer of the organic electroluminescence device. The organic compound may be for lowering a driving voltage, power consumption or increasing a current efficiency or 90% life time of the organic electroluminescence device.

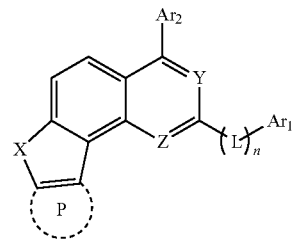

formula (A)

The same definition as described in the present invention.

9 Claims, 1 Drawing Sheet

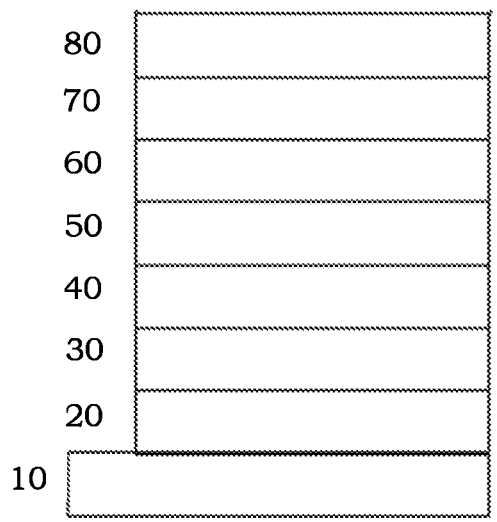

COMPOUND FOR ORGANIC ELECTROLUMINESCENCE DEVICE USING THE SAME

FIELD OF INVENTION

The present invention relates generally to a compound, and, more specifically, to an organic electroluminescence (hereinafter referred to as organic EL) device using the compound.

BACKGROUND OF THE INVENTION

An organic EL device is a light-emitting diode (LED) in which the light emitting layer is a film made from organic compounds, which emits light in response to an electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

The first observation of electroluminescence in organic materials was in the early 1950s by Andre Bernanose and his co-workers at the Nancy-University in France. Martin Pope and his co-workers at New York University first observed direct current (DC) electroluminescence on a single pure crystal of anthracene and on anthracene crystals doped with tetracene under vacuum in 1963. The first diode device was created by Ching W. Tang and Steven Van Slyke at Eastman Kodak in 1987. The diode device used a two-layer structure with separate hole transporting and electron transporting layers, resulting in reduction of operating voltage and improvement of the efficiency, thereby leading to the current era of organic EL research and device production.

Typically, organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the light emitting layer to form excitons and then emit light. When luminescent molecules absorb energy to achieve an excited state, the exciton may either be in a singlet state or a triplet state, depending on how the spins of the electrons and holes have been combined. 75% of the excitons is formed by recombination of electrons and holes to achieve the triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is achieved by certain heavy atoms, such as iridium, rhodium, platinum, and palladium, and the phosphorescent transition may be observed from an excited MLCT (metal to ligand charge transfer) state of organic metallic complexes.

The phosphorescent organic EL device utilizes both triplet and singlet excitons. Cause of longer lifetime and diffusion length of triplet excitons compared to those of singlet excitons, the phosphorescent organic EL device generally need an additional hole blocking layer (HBL) between the emitting layer (EML) and the electron transporting layer (ETL) or an electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or the electron blocking materials must have HOMO (highest occupied molecular orbital) and LUMO (lowest unoccupied molecular orbital) energy levels suitable to block hole or electron transport from the EML to the ETL or the HTL.

However, there is still a need for improvement in the case of use of those organic materials in an organic EL device of some prior art displays, for example, in relation to the lift time, current efficiency or driving voltage of the organic EL device.

SUMMARY OF THE INVENTION

According to the reasons described above, the present invention has the objective of resolving the problems of prior arts and offering a novel compound. Another object of the invention is to provide an organic EL device using the compound. The organic EL device of the present invention can operate under reduced voltage and exhibit higher current efficiency and longer life time. The present invention discloses an organic compound of formula (A):

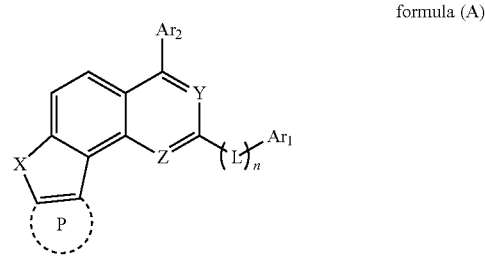

formula (A)

wherein X may be a divalent bridge selected from the group consisting of O and S. Y and Z may be independently C(Rs) or N. Rs may be a hydrogen atom or an alkyl group. At least one of Y and Z may be N. P may represent a substituted or unsubstituted fused ring hydrocarbons unit having two rings. The fused ring hydrocarbons unit may be, for example, a naphthyl group. L may represent a single bonded, a substituted or unsubstituted arylene group having 6 to 30 ring carbon atoms or a substituted or unsubstituted heteroaryl group having 5 to 30 ring atoms. The symbol n may represent an integer of 0 to 1. $Ar_1$ may be selected from the group consisting of a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms. $Ar_2$ may represent a phenyl group or a naphthyl group.

The present invention further discloses an organic electroluminescence device. The organic electroluminescence device comprises a pair of electrodes having a cathode and an anode. Between the pair of electrodes, the organic electroluminescence device comprises at least a light emitting layer and one or more layers of organic thin film layers. The light emitting layer and/or the one or more thin film layers comprise the organic compound of formula (A). The light emitting layer comprising the compound of formula (A) may be a host material. The organic electroluminescence device may be a lighting panel or a backlight panel.

The light emitting layer may be an emitting layer comprising emitting host materials and a phosphorescent dopant material. The emitting host material may be doped with about 15% emitting phosphorescent dopant (guest) material. The light emitting layer may have a thickness of about 30 nm.

An organic EL device of the present invention comprises an organic compound of formula (A) as a dopant material to collocate with, for example, and not limited to a host material CBP, to emit a red light, thereby lowering a driving voltage to about but not limited to 4.2-4.6 V, increasing a current efficiency to about but not limited to 16.4-17.8 cd/A, or increasing a 90% life time to about but not limited to 90-150 hours.

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a compound which can be used as the host material of the organic EL device is disclosed. The compound is represented by the following formula (A):

formula (A)

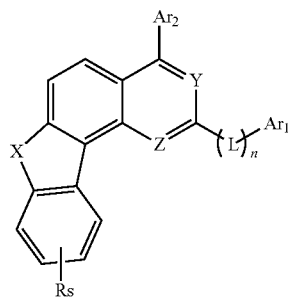

wherein X may be a divalent bridge selected from the group consisting of O and S. Y and Z may be independently C(Rs) or N. Rs may be a hydrogen atom or an alkyl group. At least one of Y and Z may be N. P may represent a substituted or unsubstituted fused ring hydrocarbons unit having two rings. The fused ring hydrocarbons unit may be, for example, a naphthyl group. L may represent a single bonded, a substituted or unsubstituted arylene group having 6 to 30 ring carbon atoms or a substituted or unsubstituted heteroaryl group having 5 to 30 ring atoms. The symbol n may represent an integer of 0 to 1. $Ar_1$ may be selected from the group consisting of a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms. $Ar_2$ may represent a phenyl group or a naphthyl group.

The organic compound may be represented by one of the following formula (B) to formula (J):

formula (B)

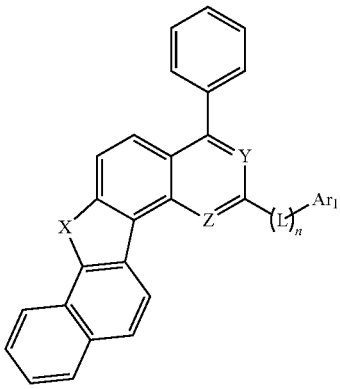

formula (C)

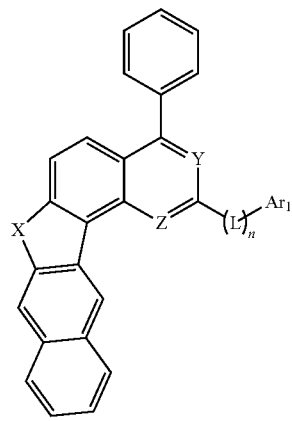

formula (D)

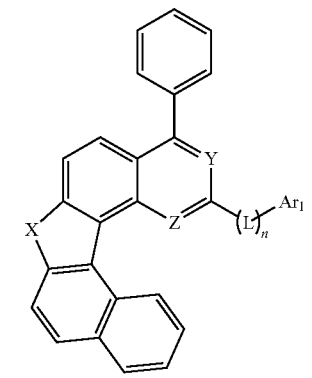

formula (E)

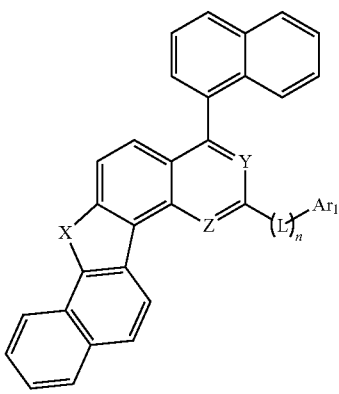

formula (F)

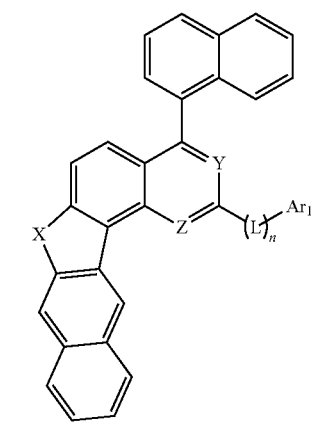

formula (G)

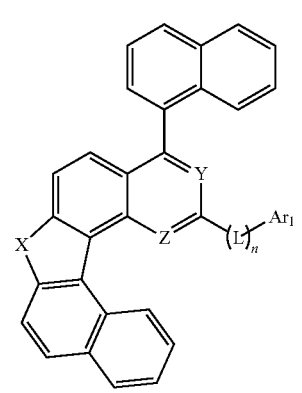

formula (H)

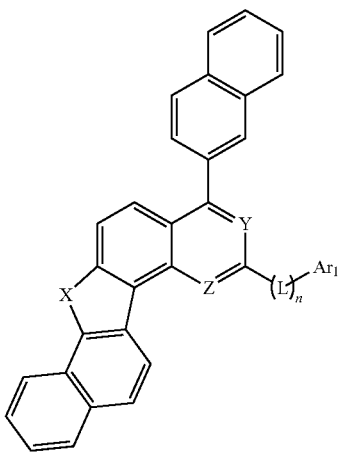

formula (I)

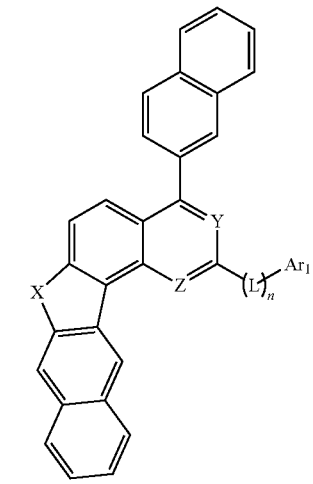

formula (J)

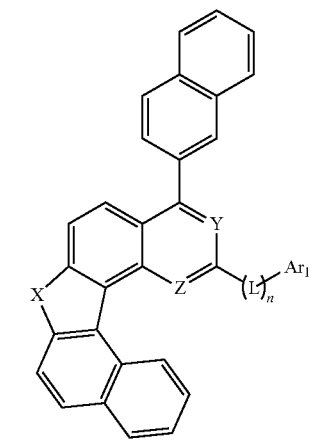

Ar₁ may be a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, or a substituted or unsubstituted pyridinyl group.
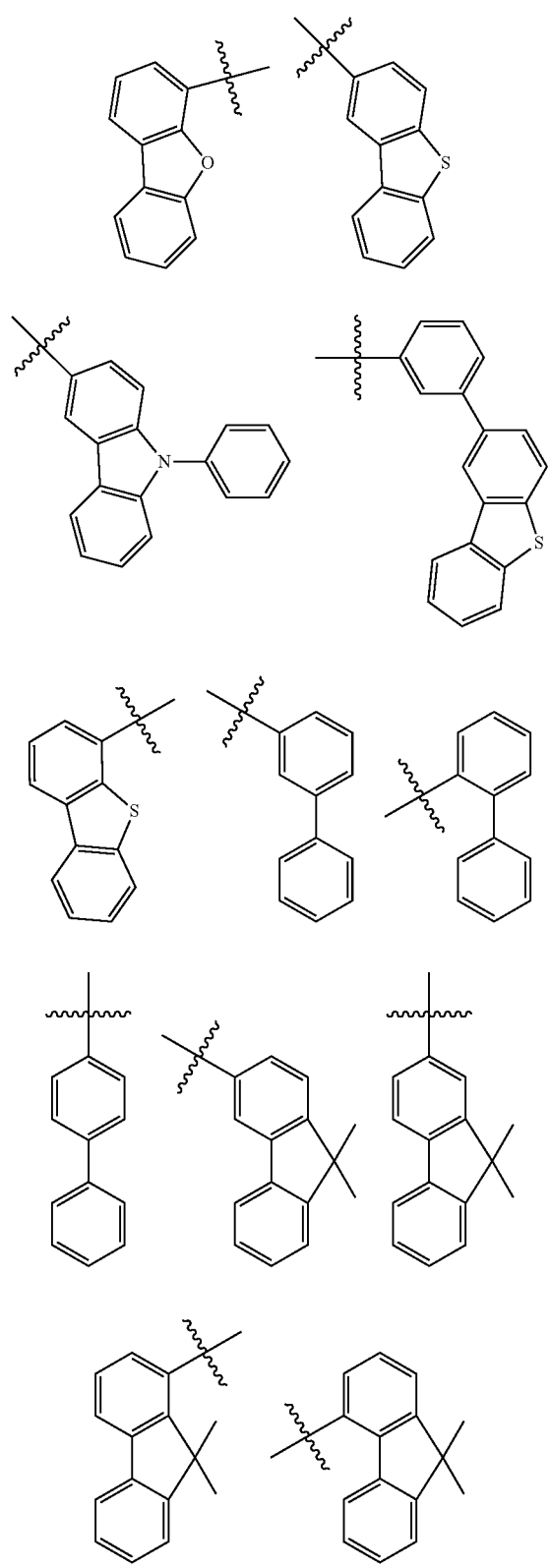
-continued
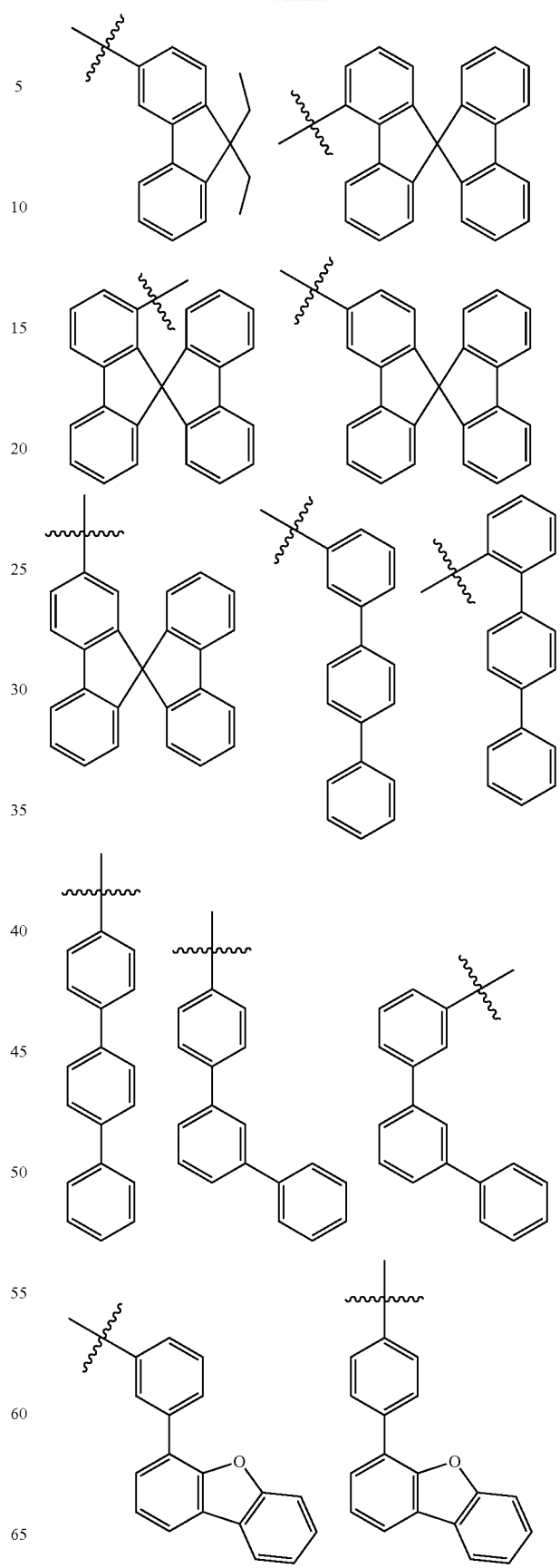

-continued
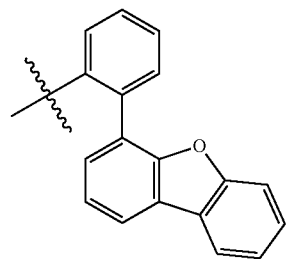
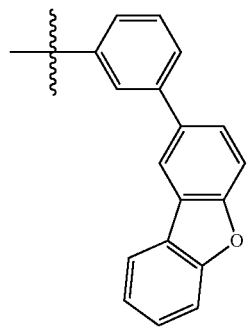
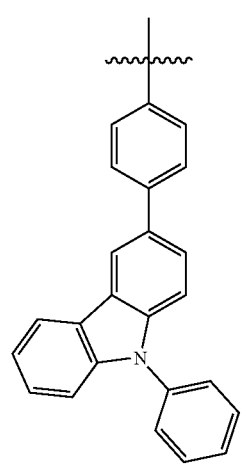
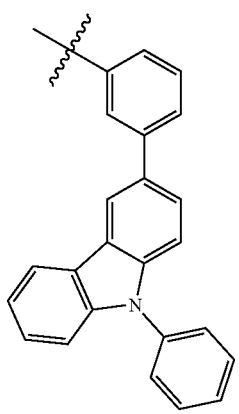
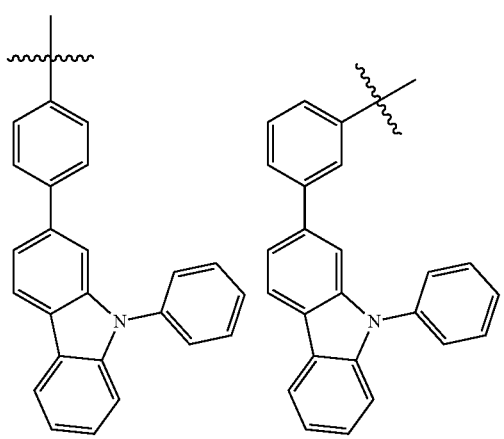
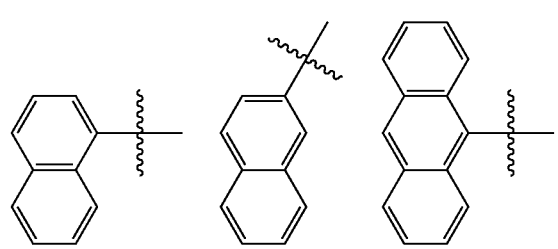
Ar$_1$ may represent one of the following substituents:
C1
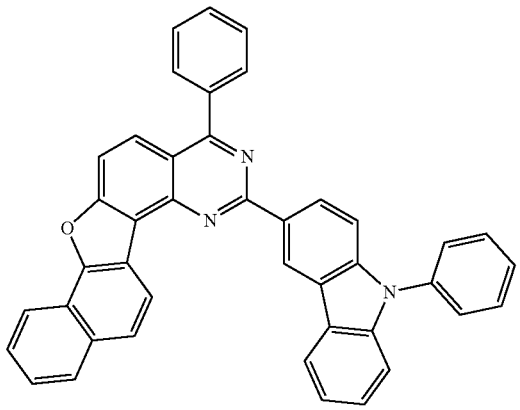
C2
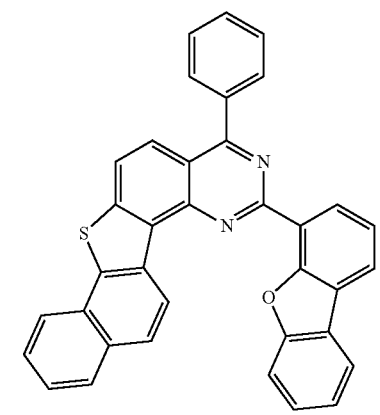
C3
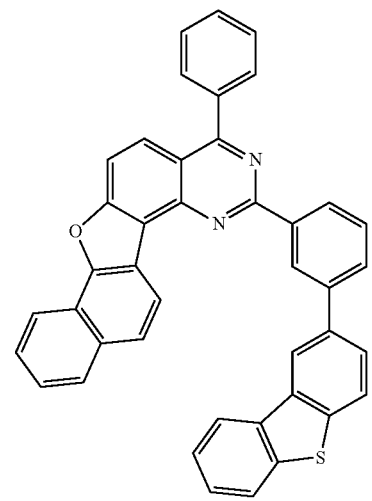

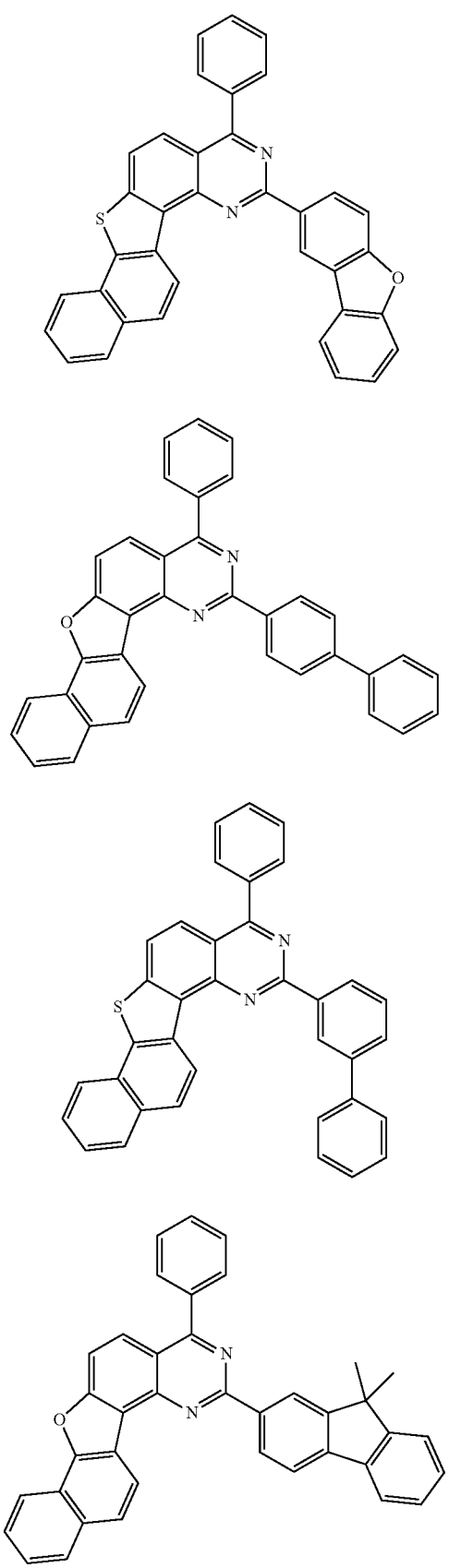
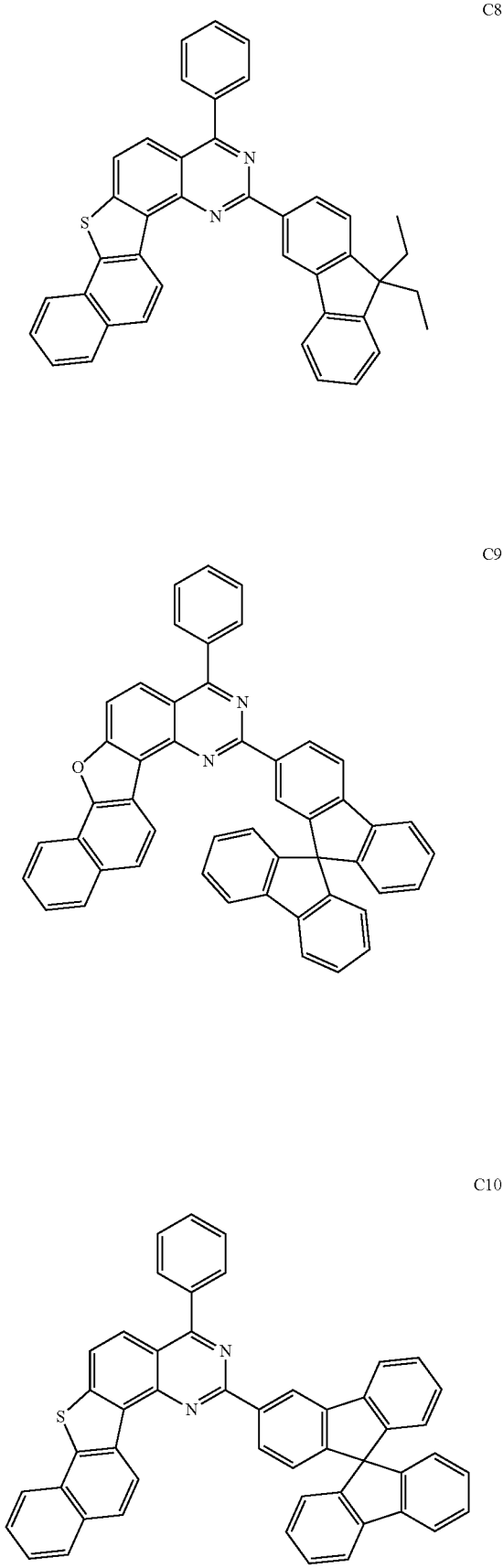

C11
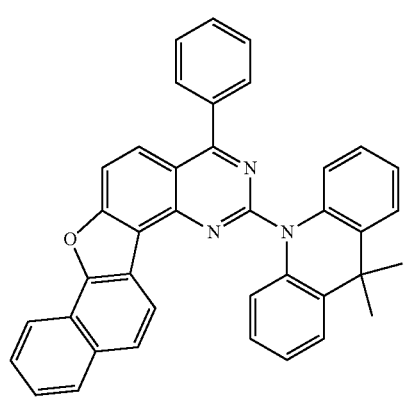
C12
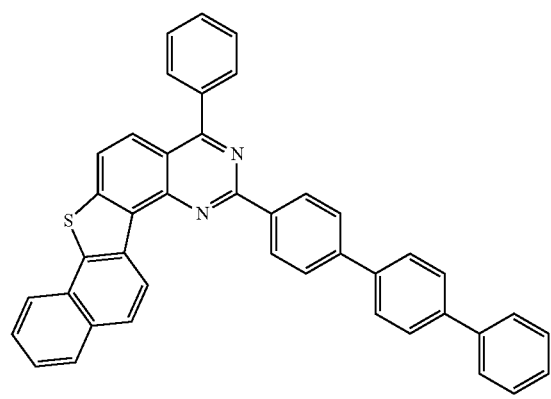
C13
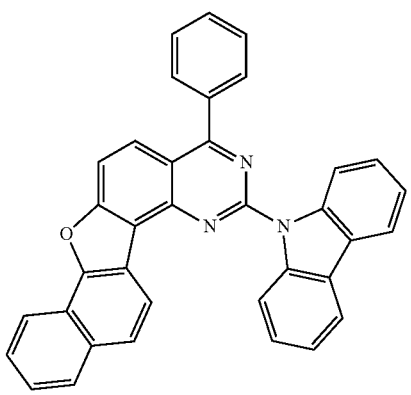
C14
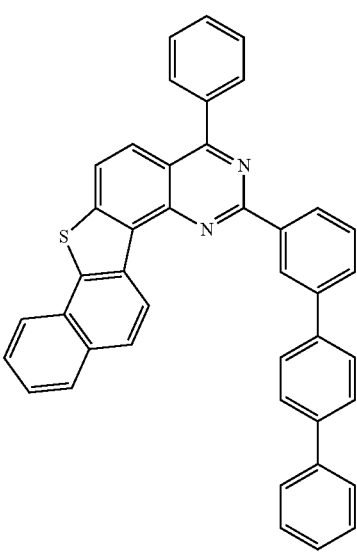
C15
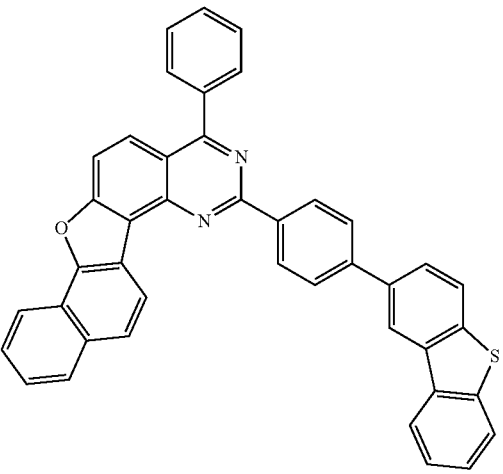
C16
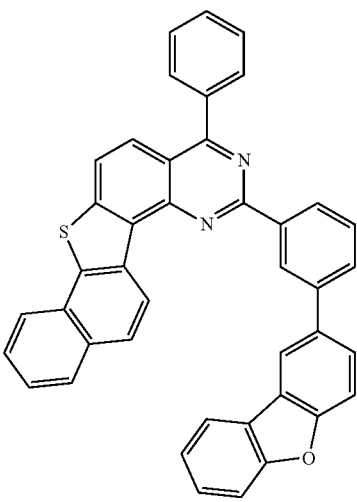

C17
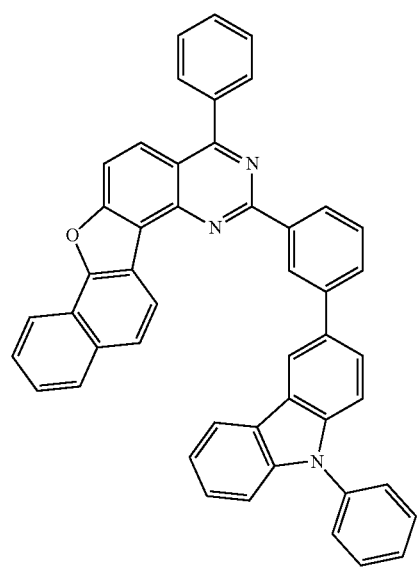
C18
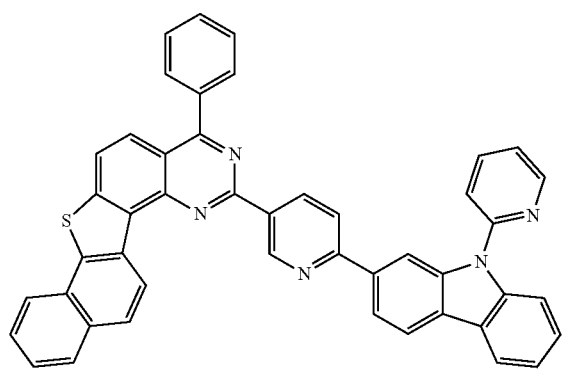
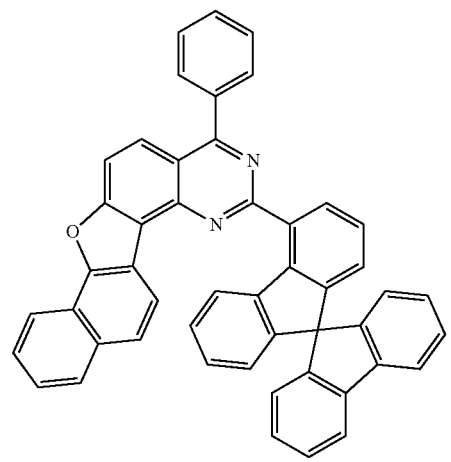
C20
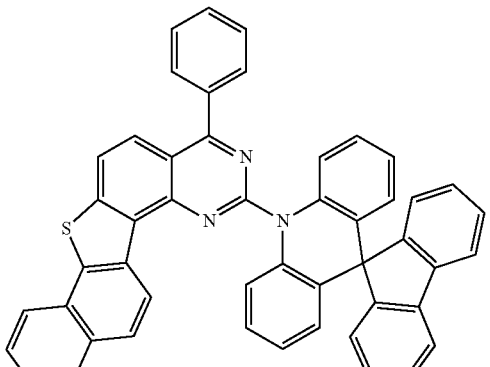
C21
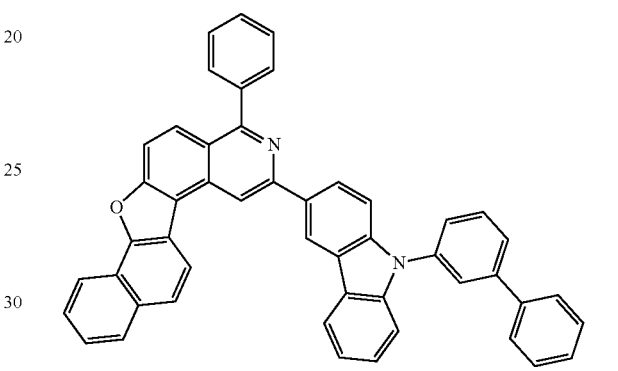
C22
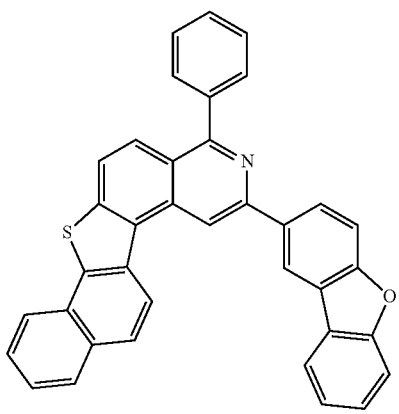
C23
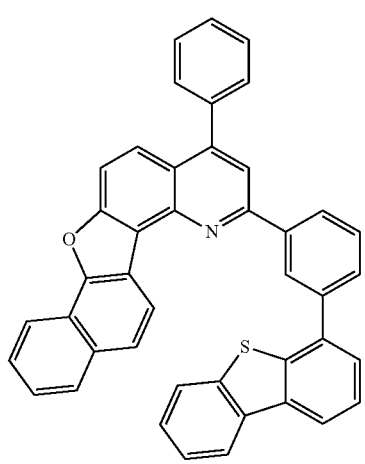

C24
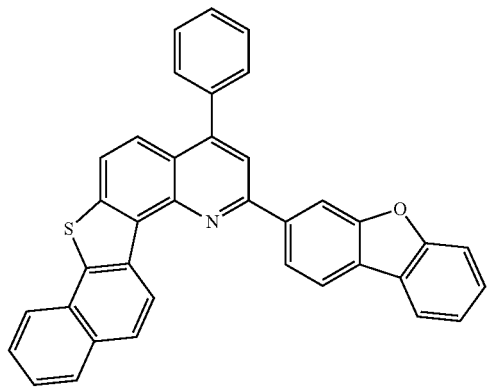
C25
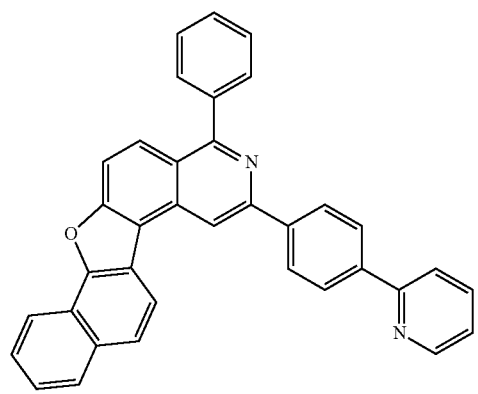
C26
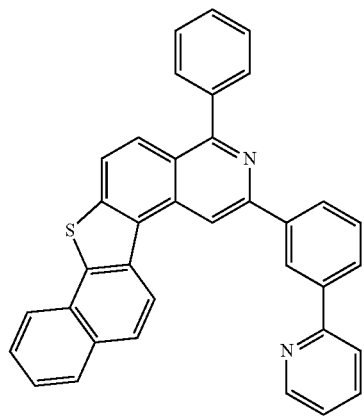
C27
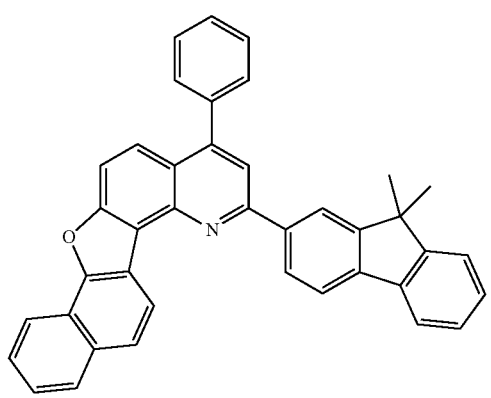
C28
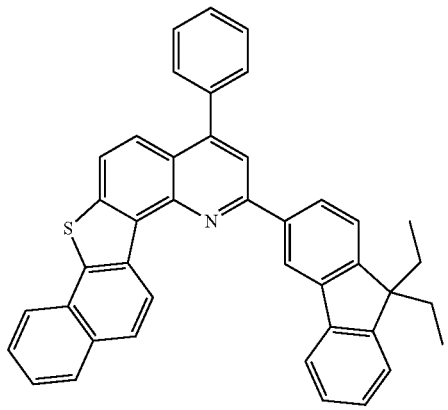
C29
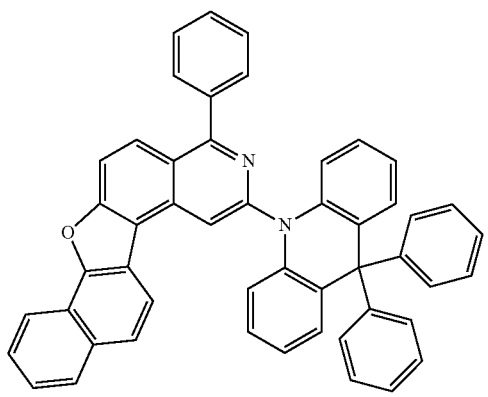
C30
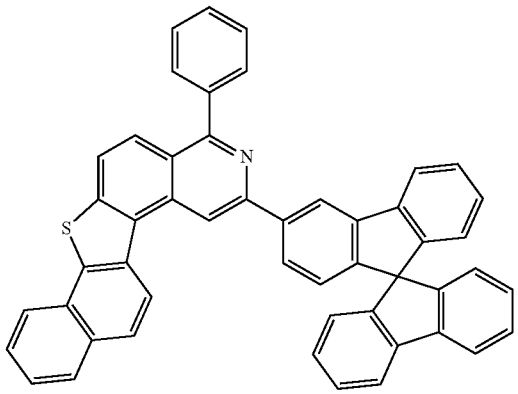
C31
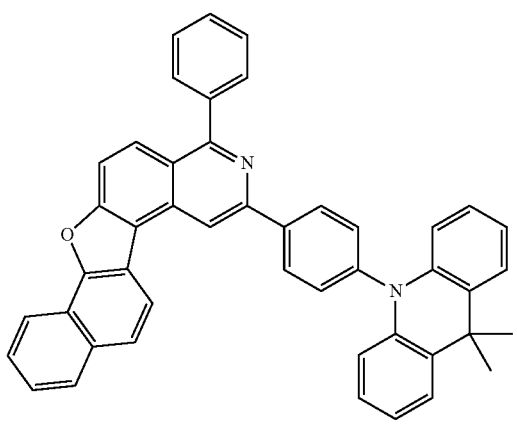

19
-continued
C32
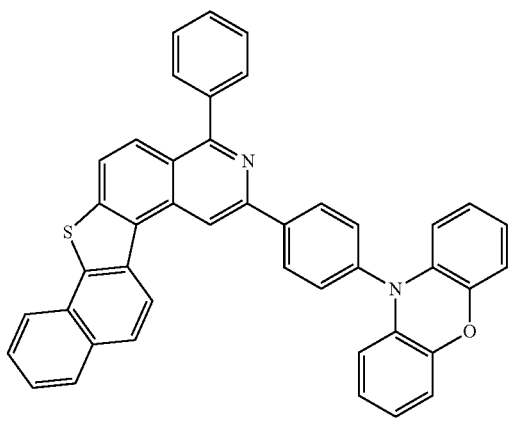
C33
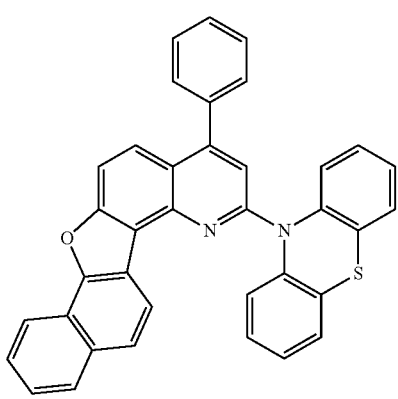
C34
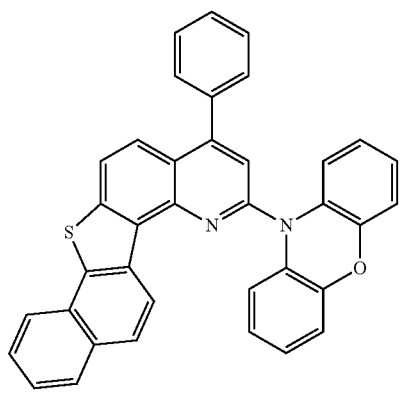
C35
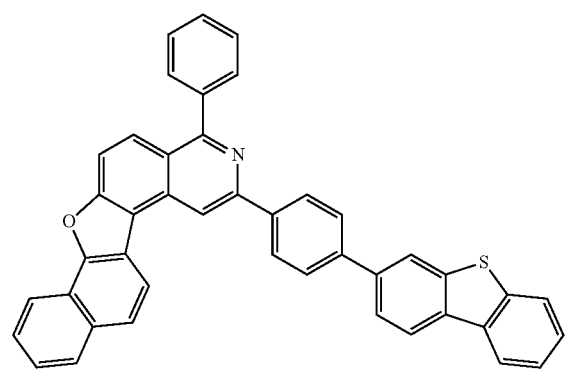
20
-continued
C36
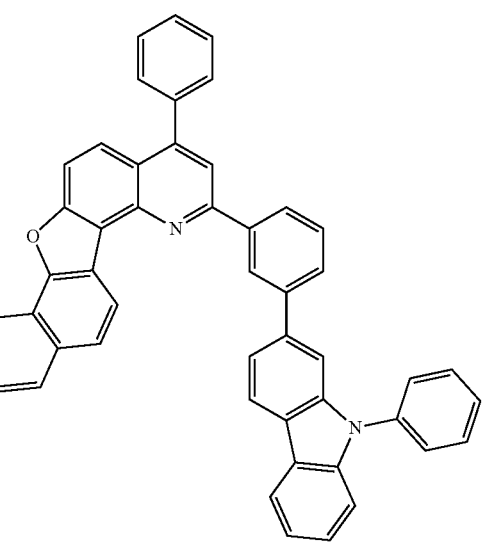
C37
C38
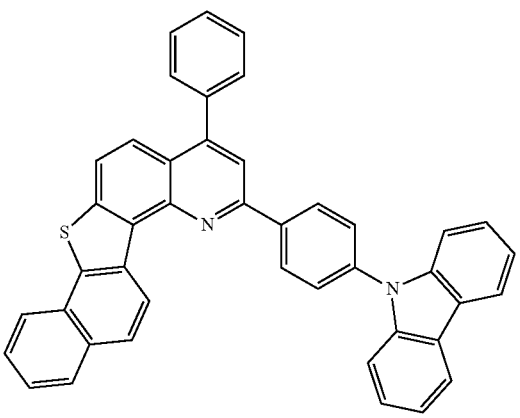

C39
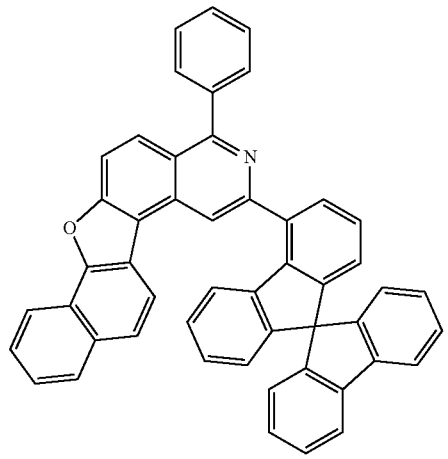
C40
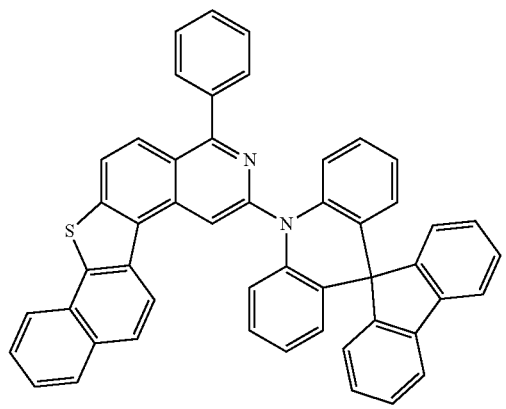
C41
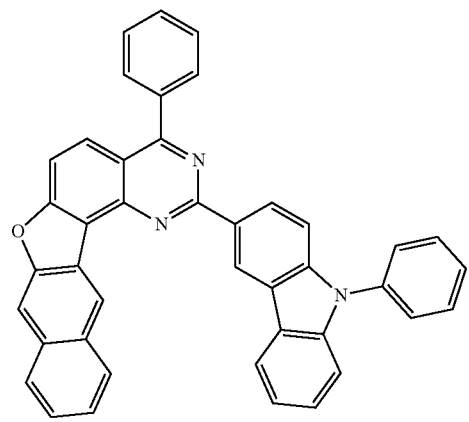
C42
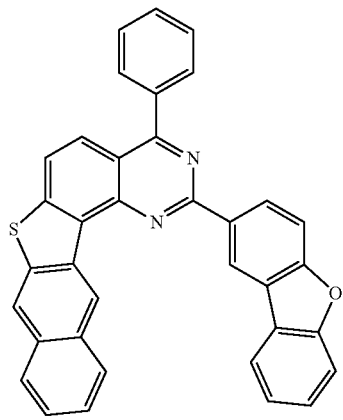
C43
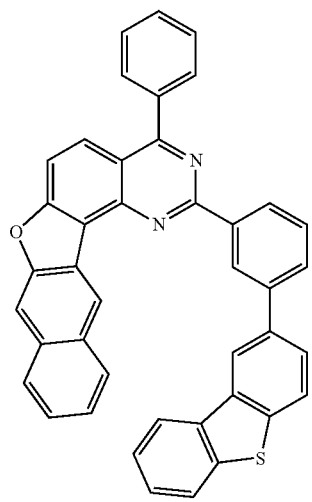
C44
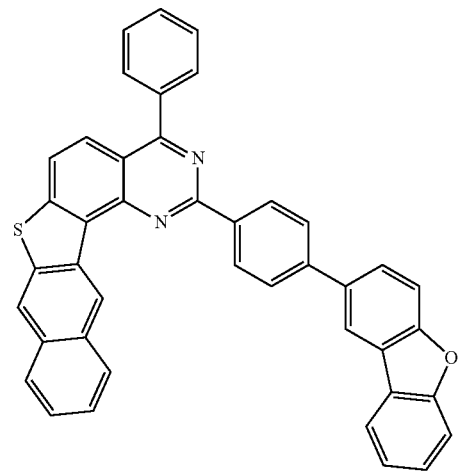

-continued
C45
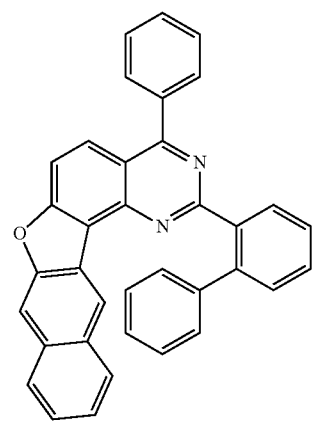
C46
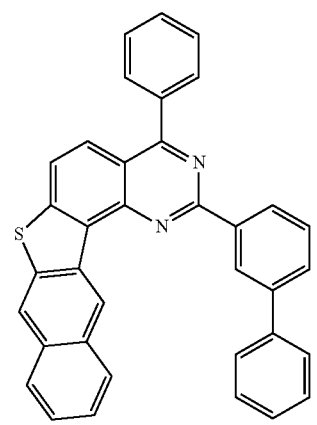
C47
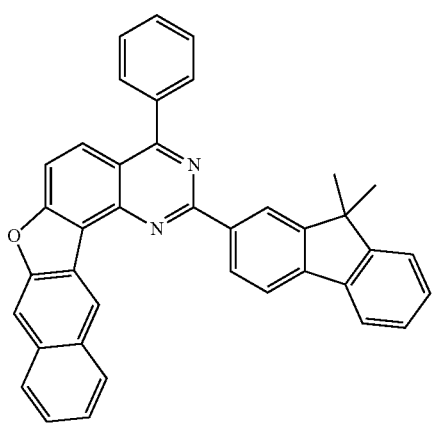
-continued
C48
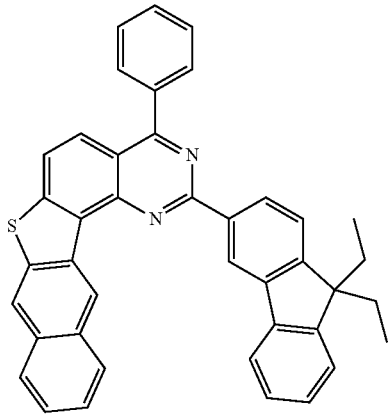
C49
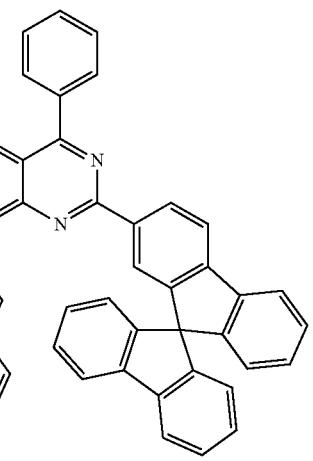
C50
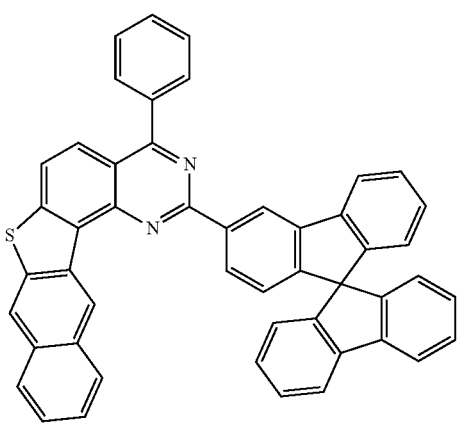

C51
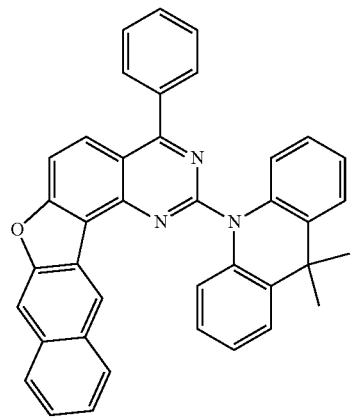
C52
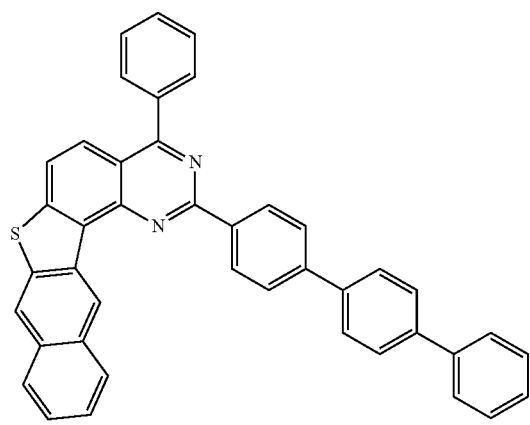
C53
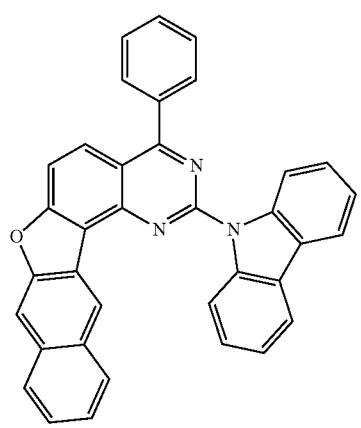
C54
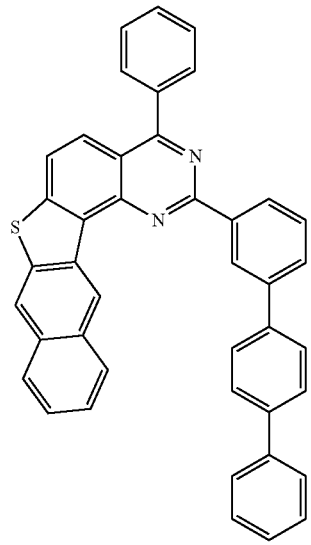
C55
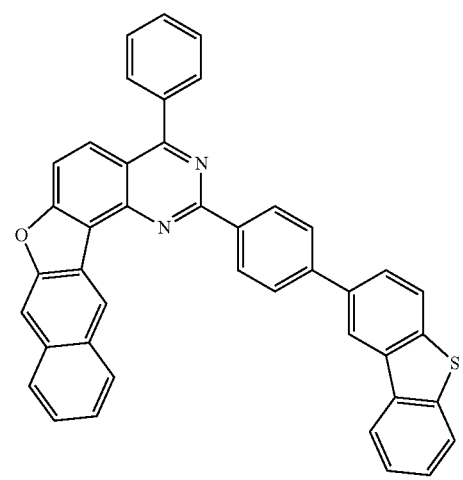
C56
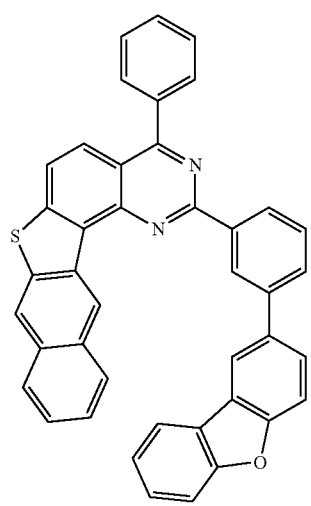

-continued
C57
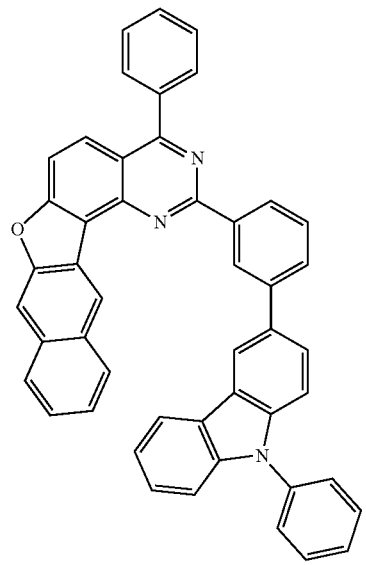
C58
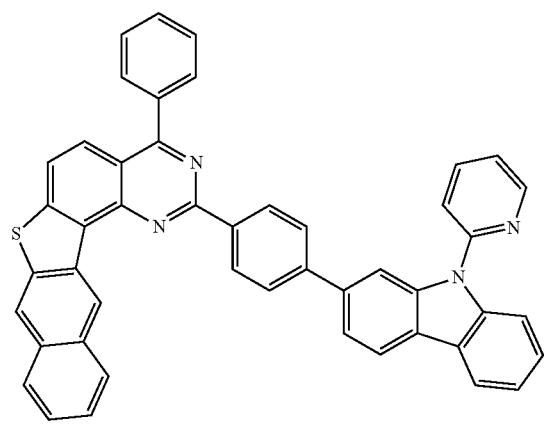
C59
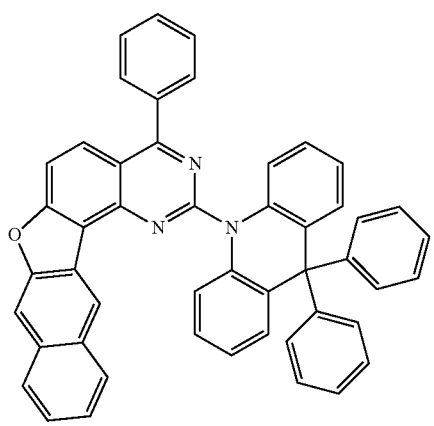
-continued
C60
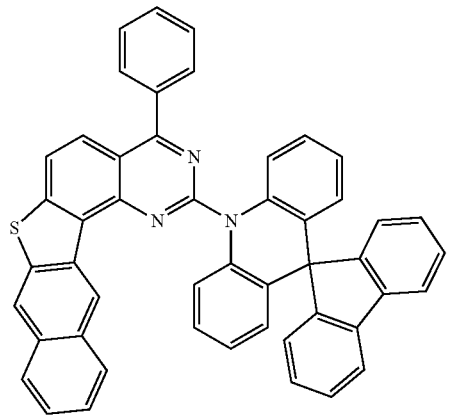
C61
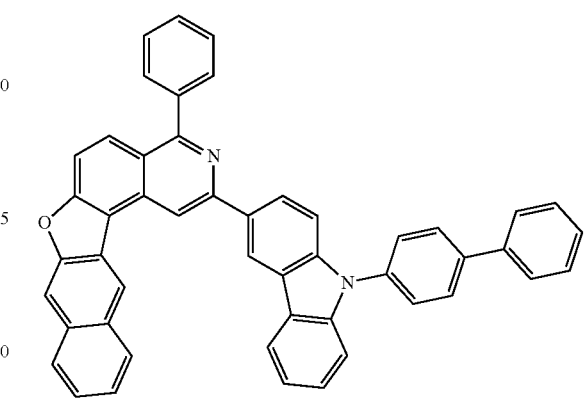
C62
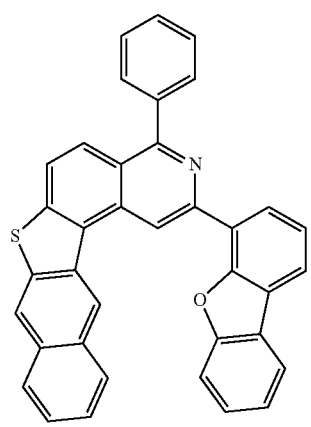

C63
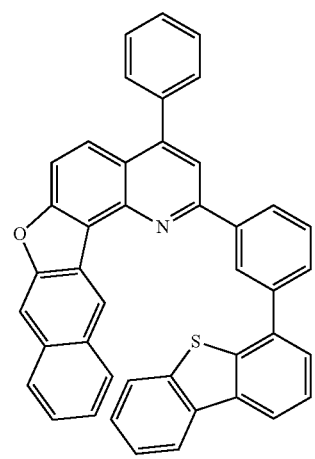
C66
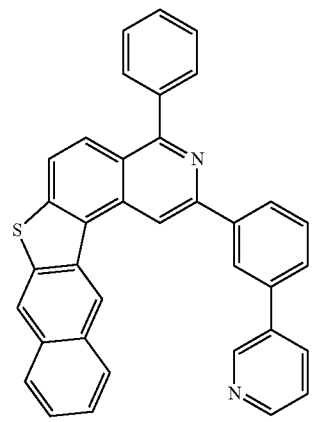
C64
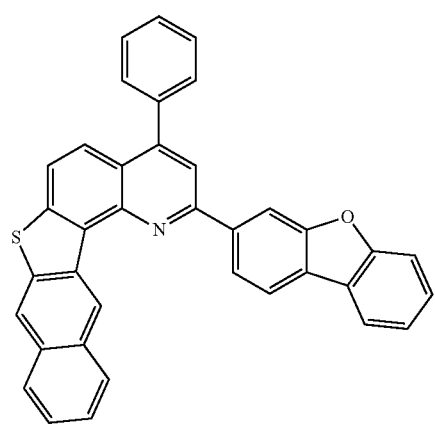
C67
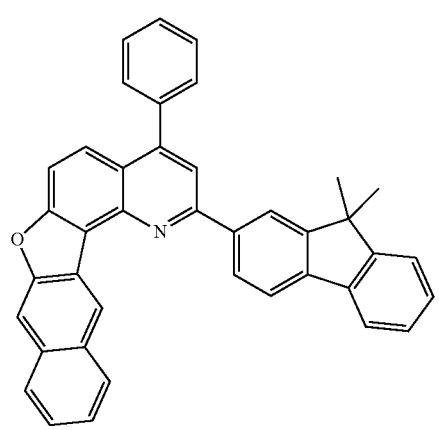
C65
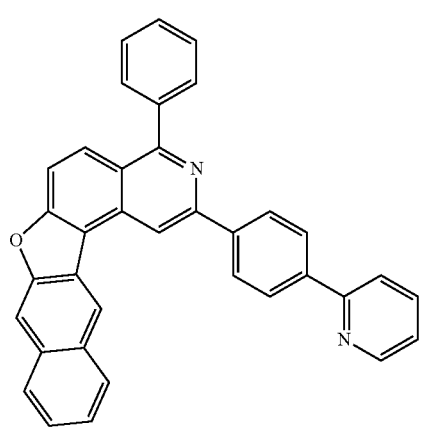
C68
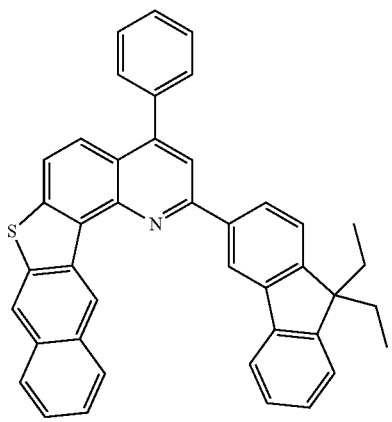

-continued
C69
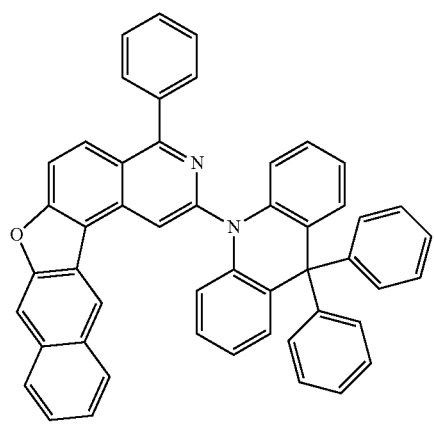
C70
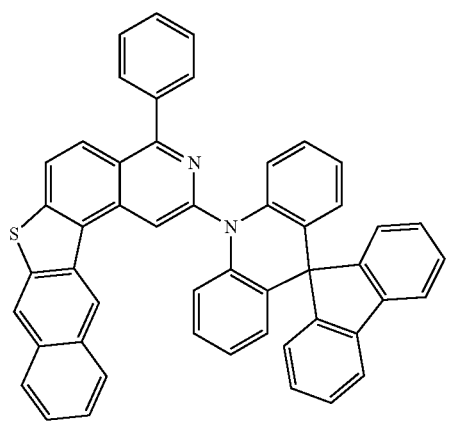
C71
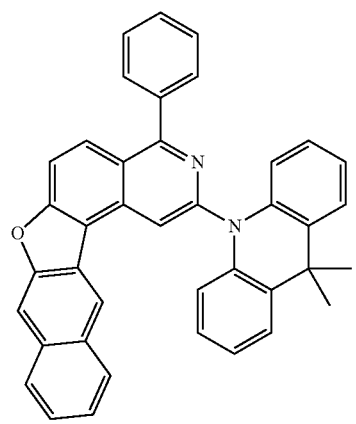
-continued
C72
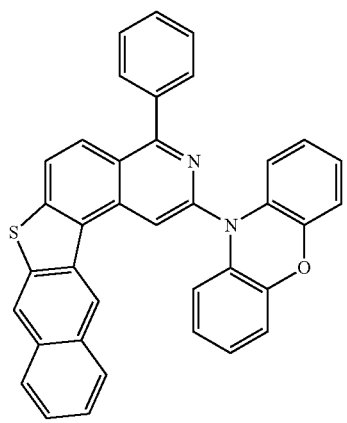
C73
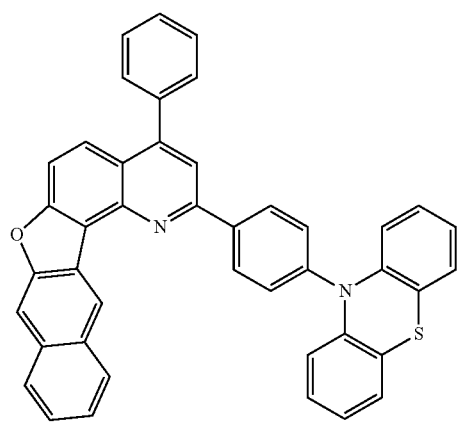
C74
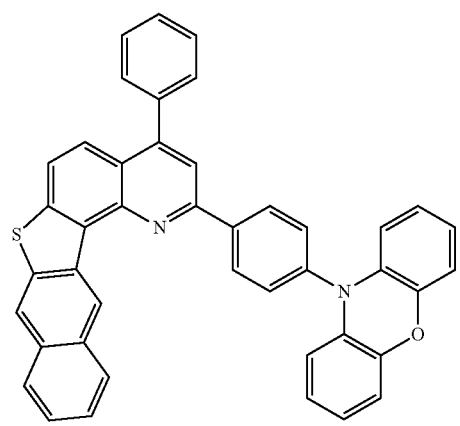

C75
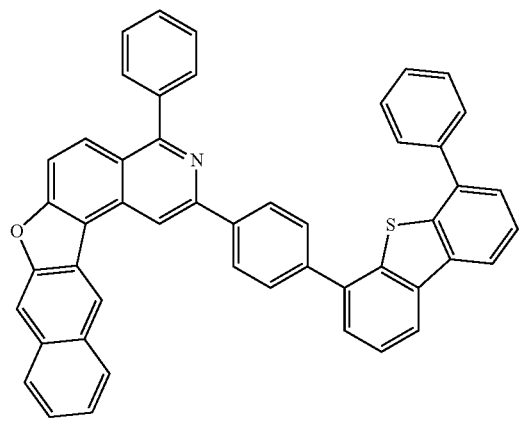
C76
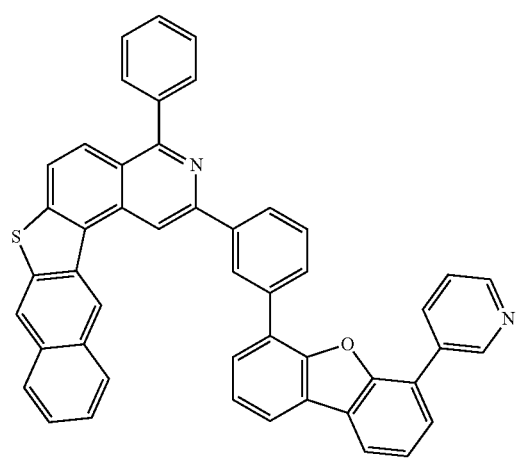
C77
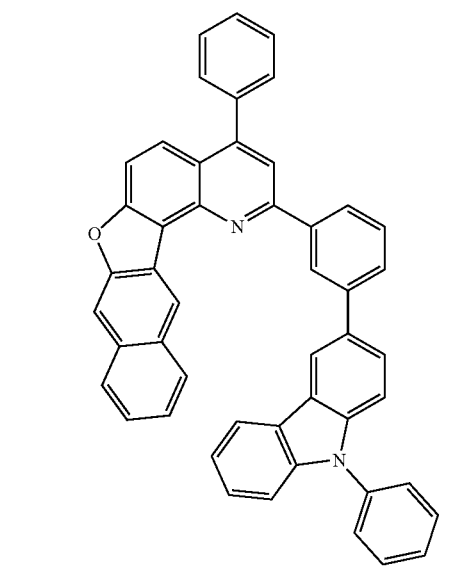
C78
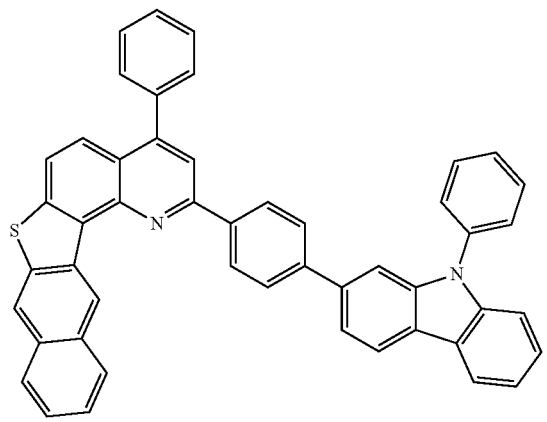
C79
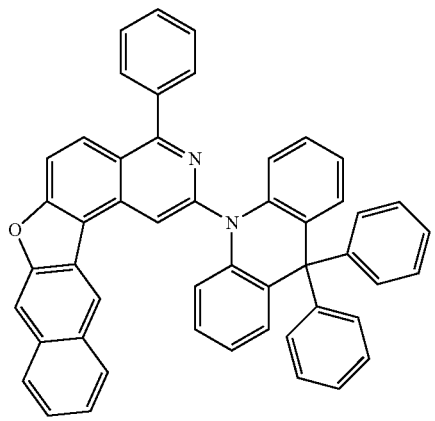
C80
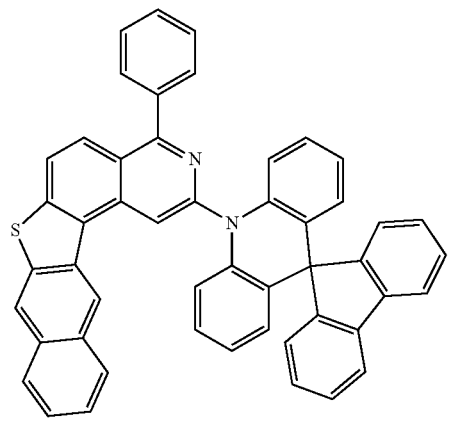
C81
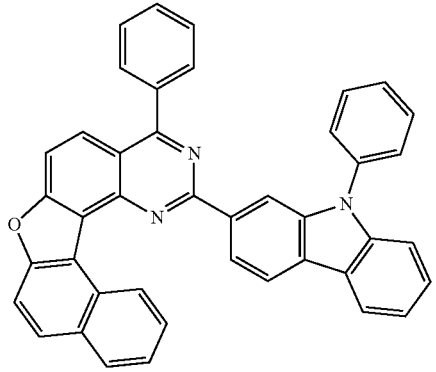

C82
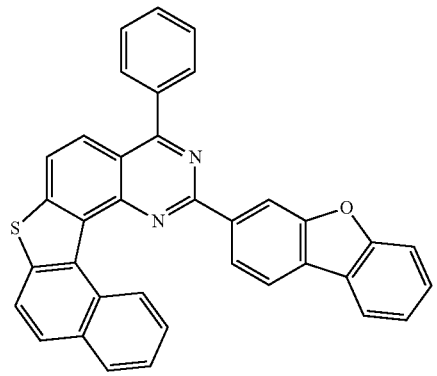
C83
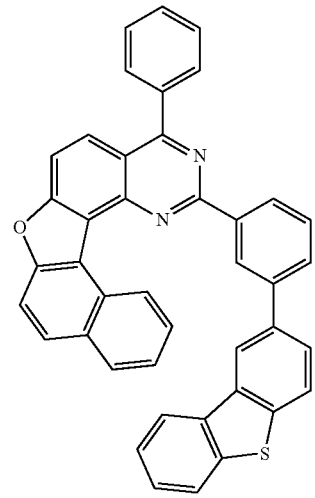
C84
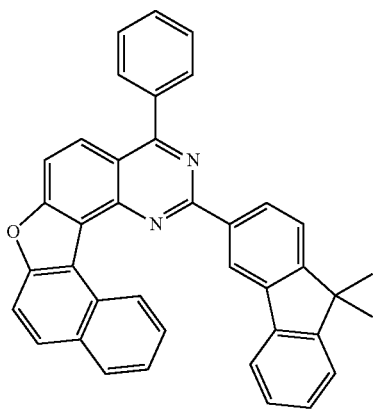
C85
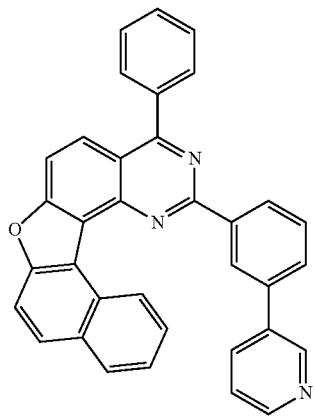
C86
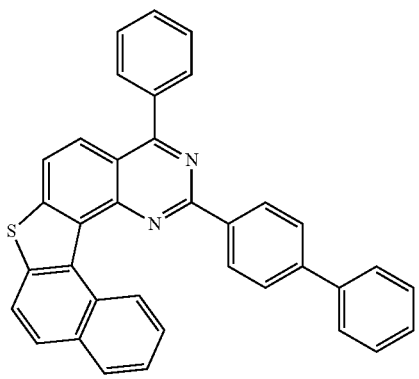
C87
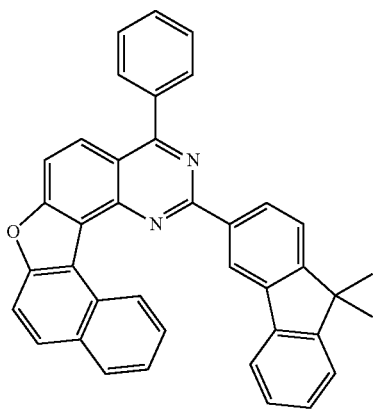
C88
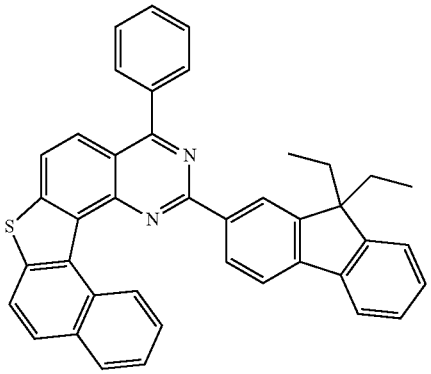

C89
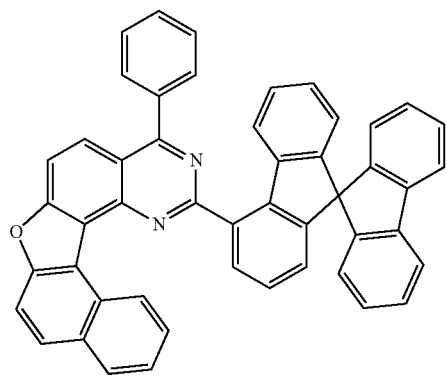
C90
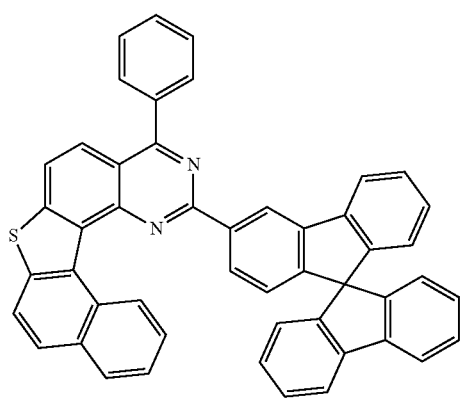
C91
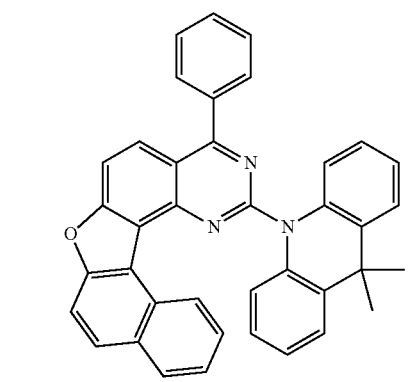
C92
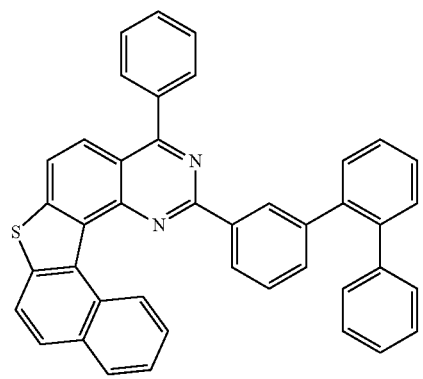
C93
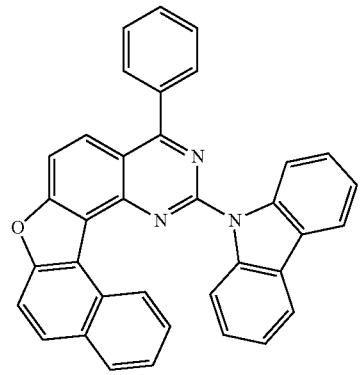
C94
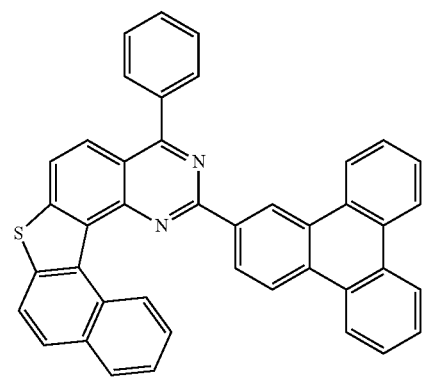
C95
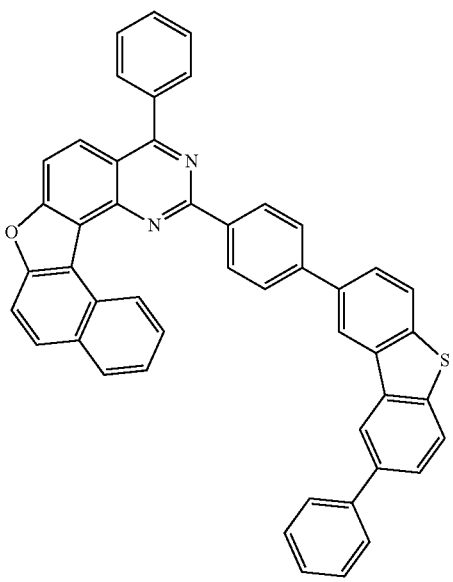

-continued
C96
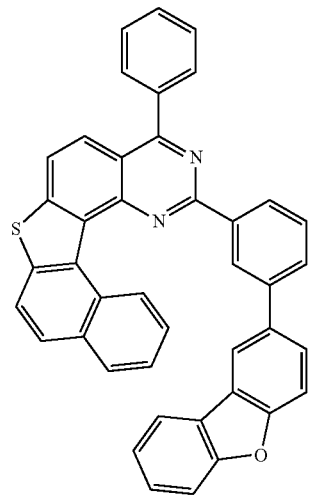
C97
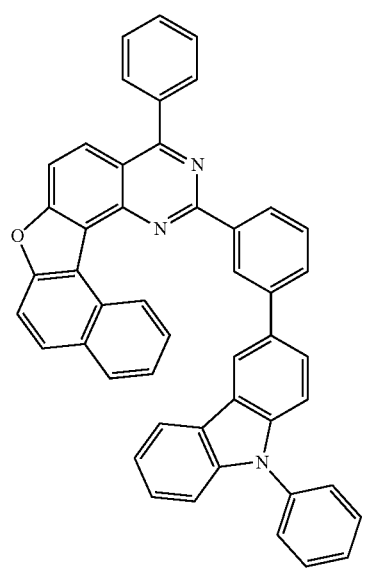
C98
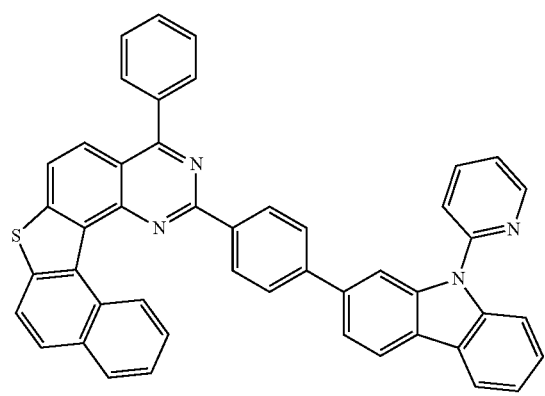
-continued
C99
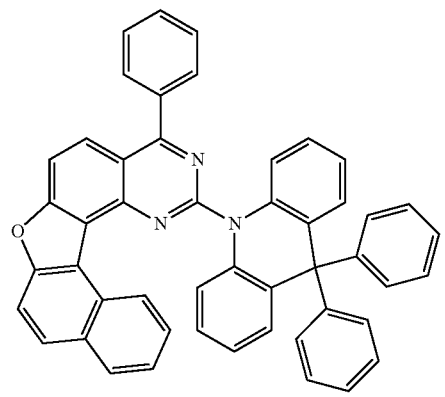
C100
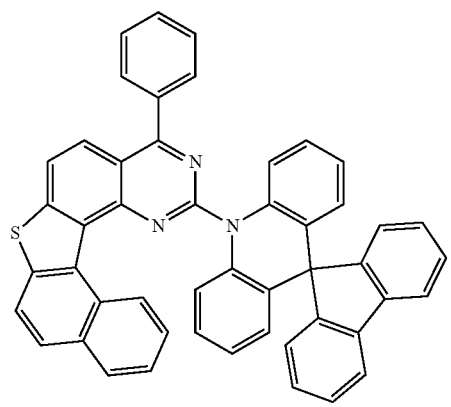
C101
C102
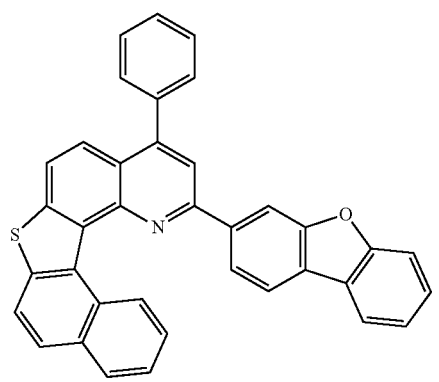

C103
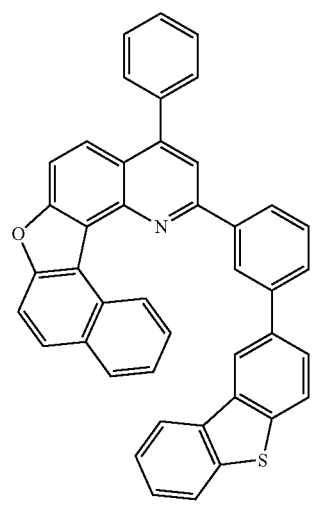
C104
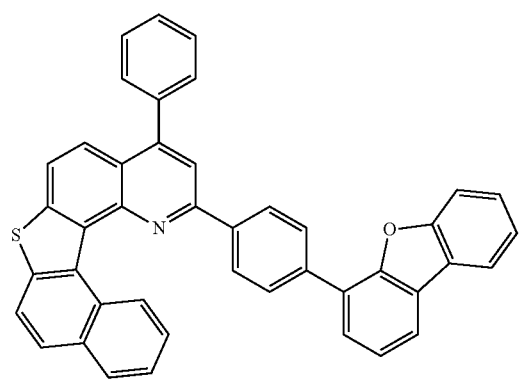
C105
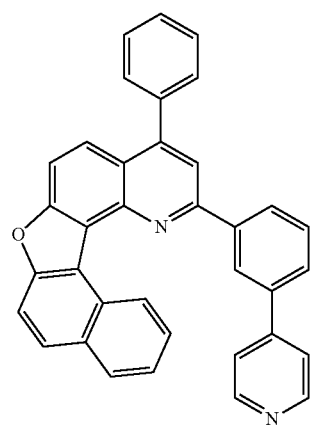
C106
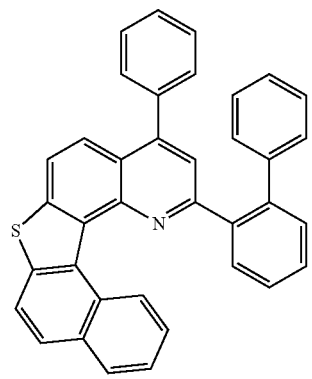
C107
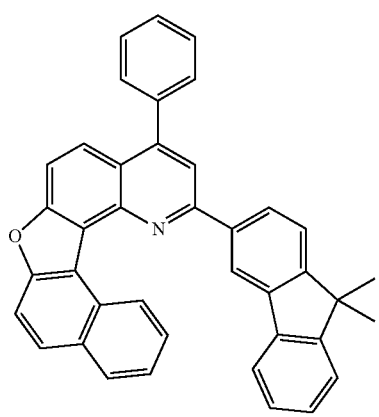
C108
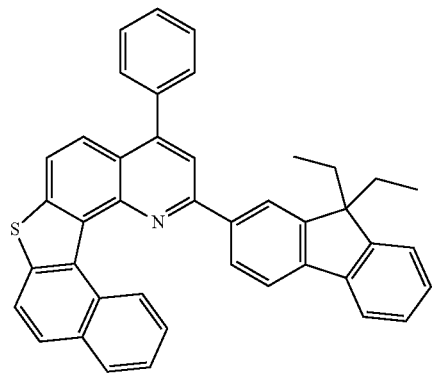
C109
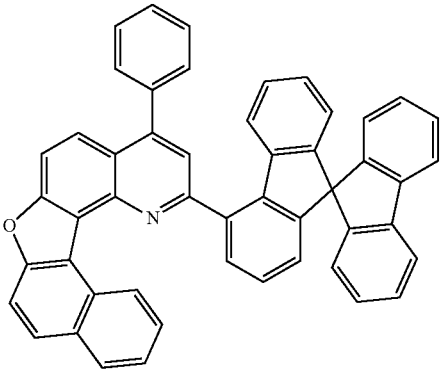

C110
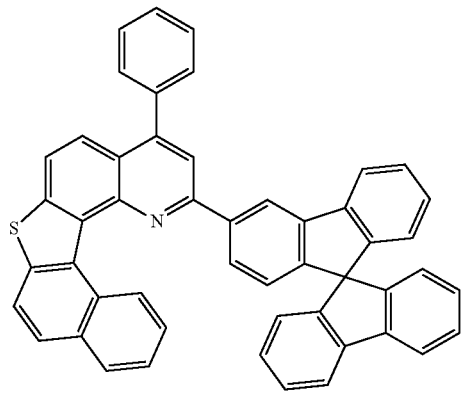
C111
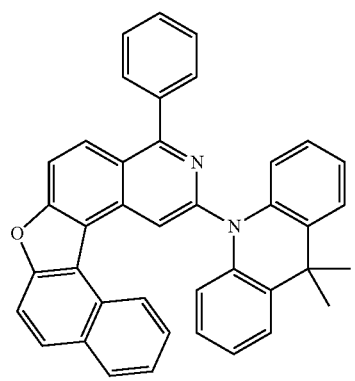
C112
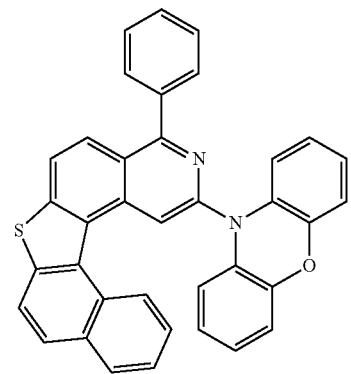
C113
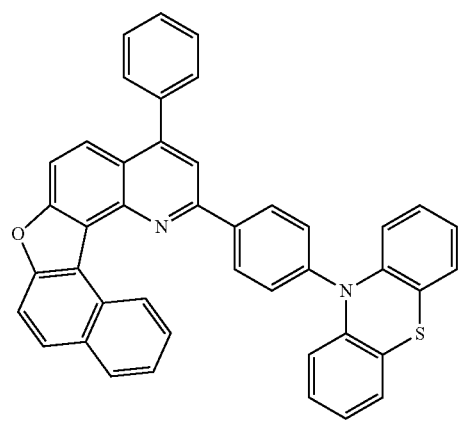
C114
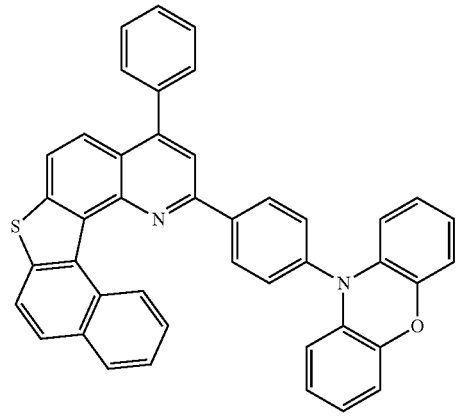
C115
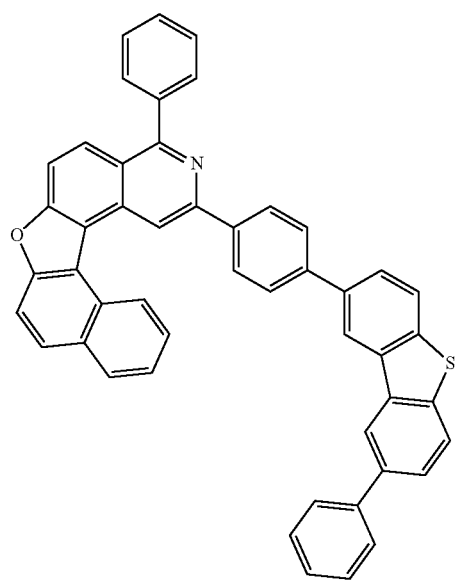
C116
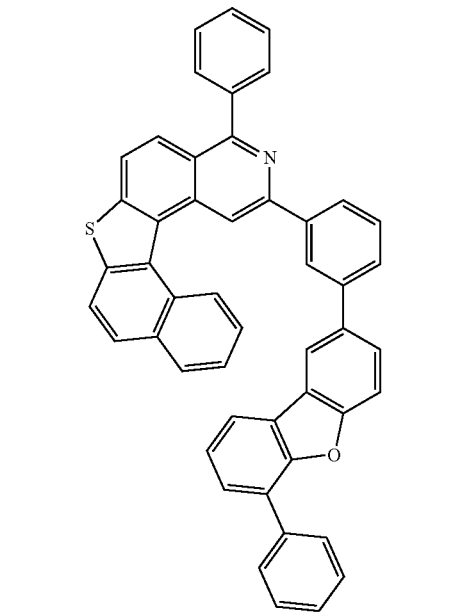

C117
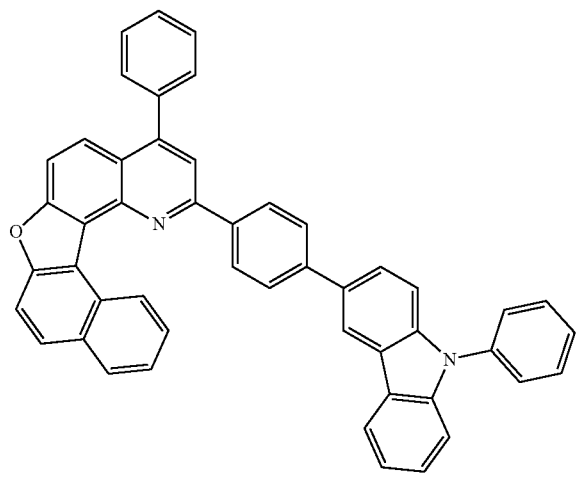
C120
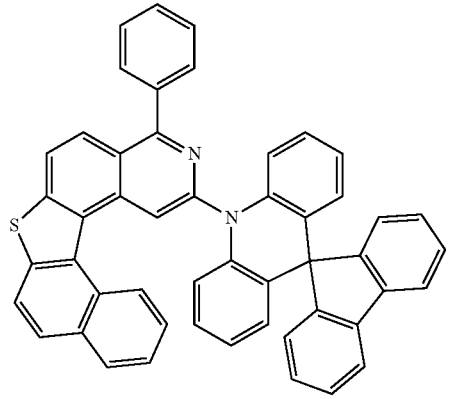
C118
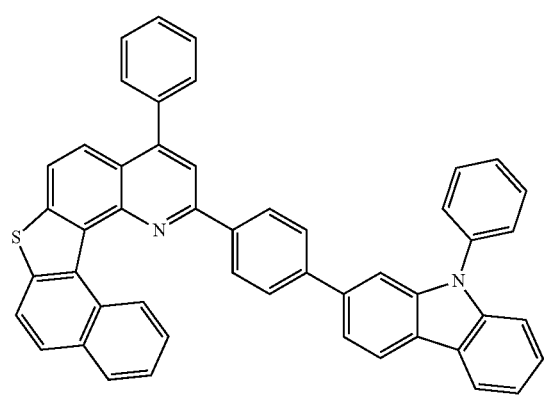
C121
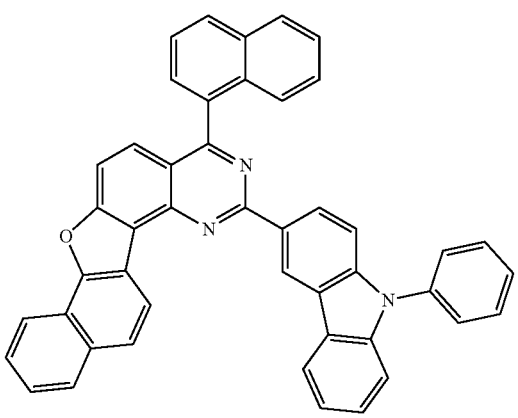
C119
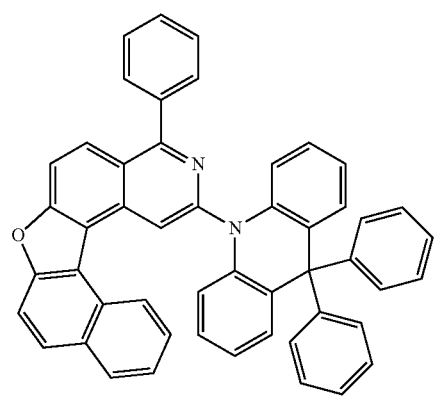
C122
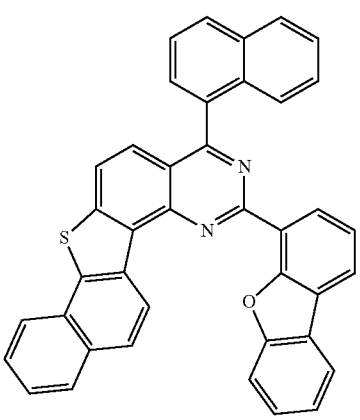

C123
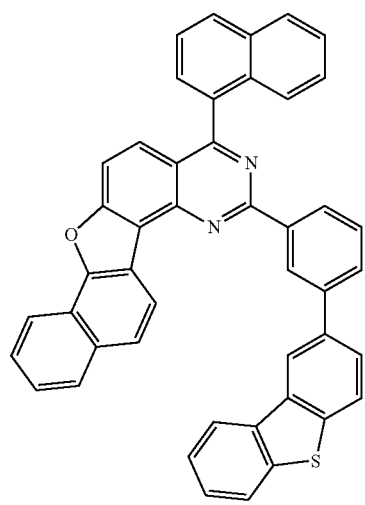
C124
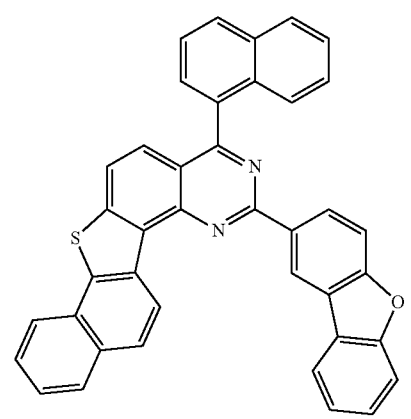
C125
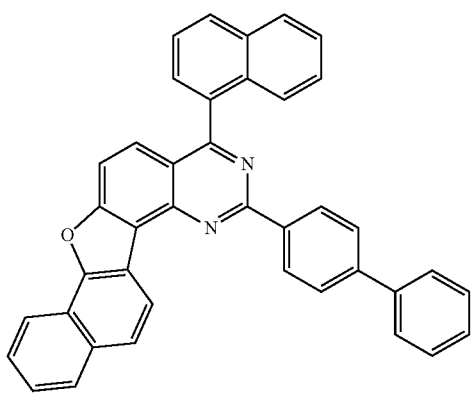
C126
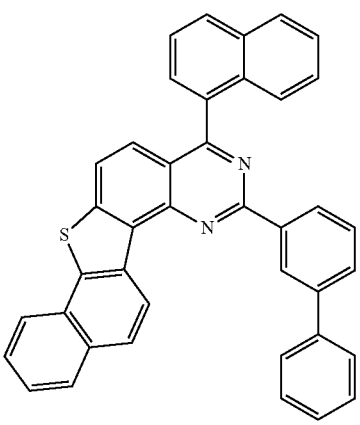
C127
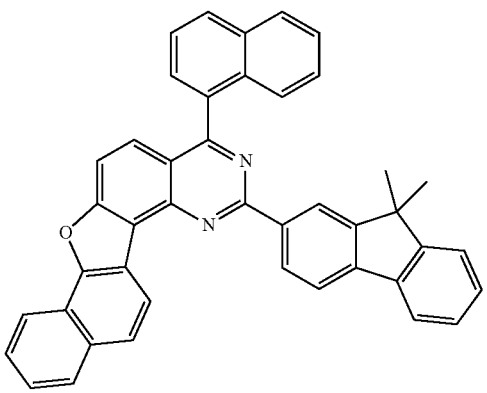
C128
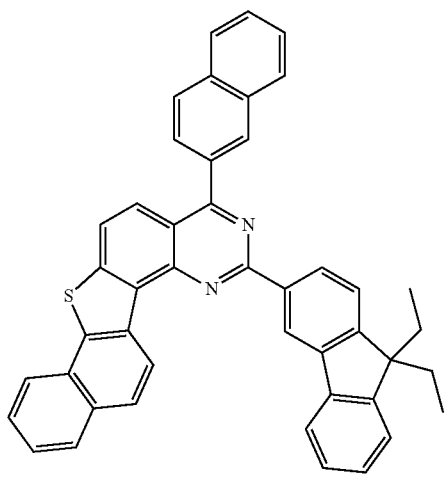

-continued
C129
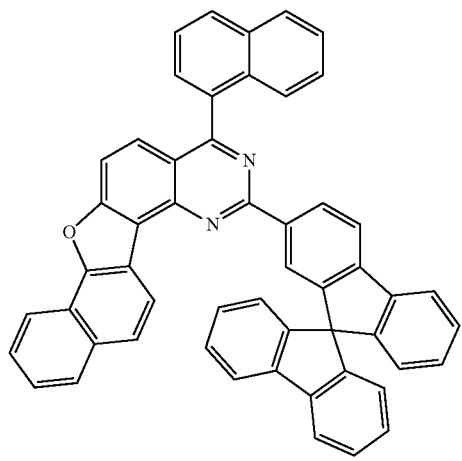
C130
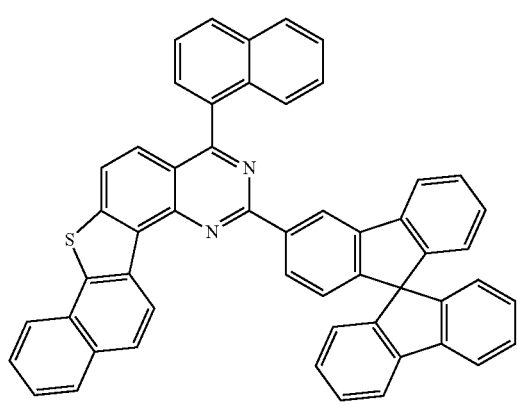
C131
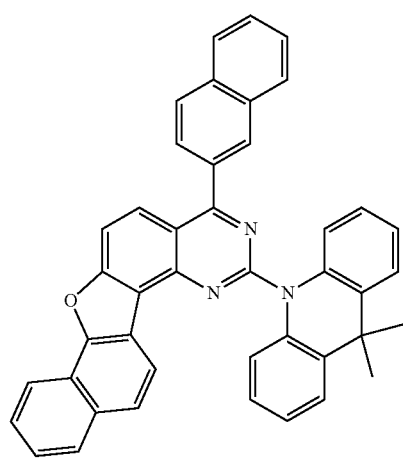
-continued
C132
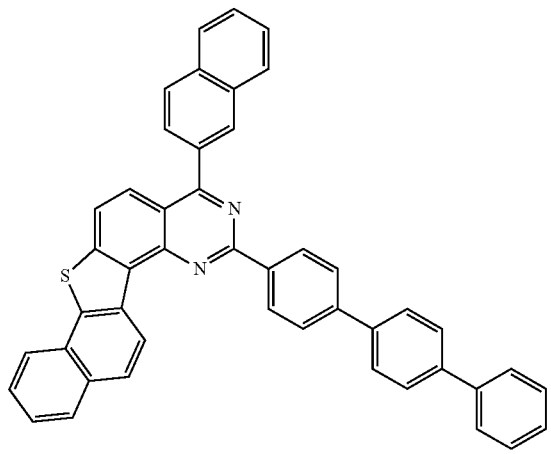
C133
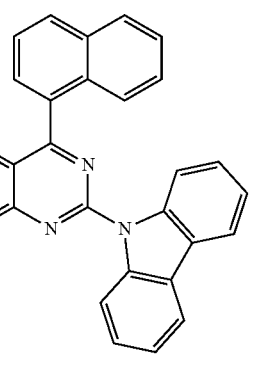
C134
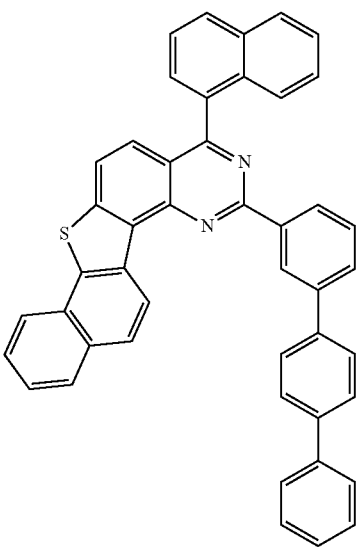

-continued
C135
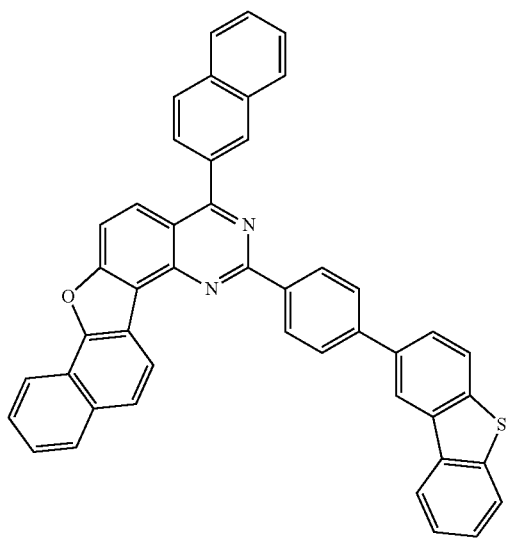
C136
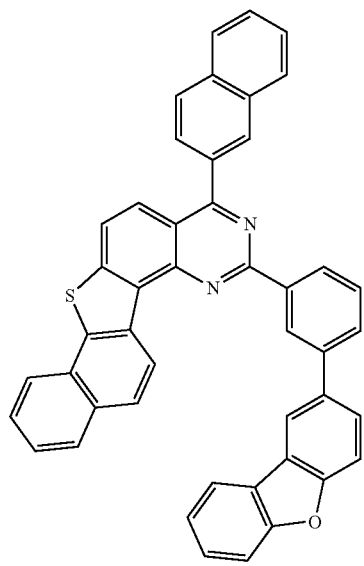
-continued
C137
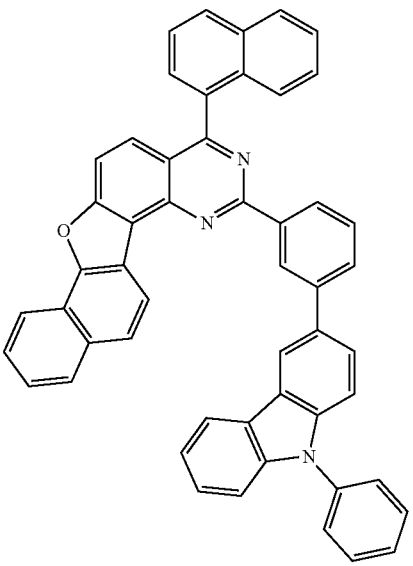
C138
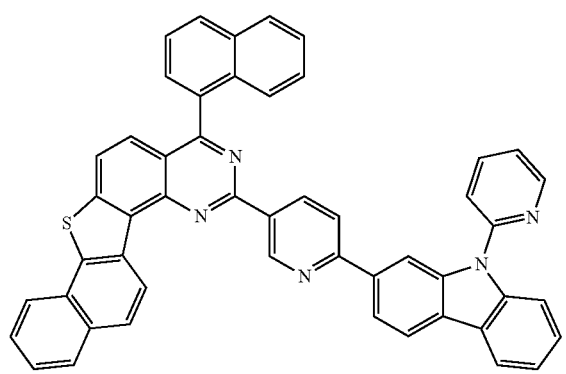
C139
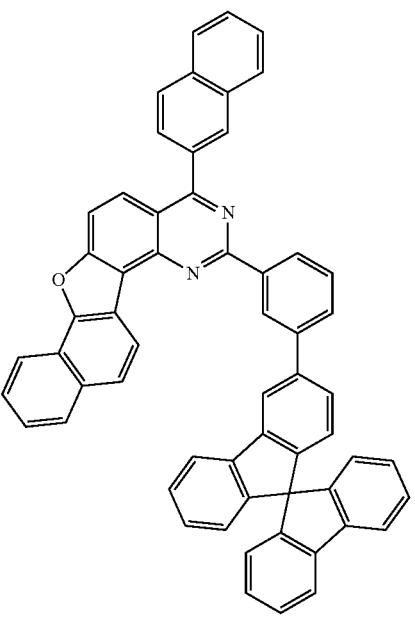

C140
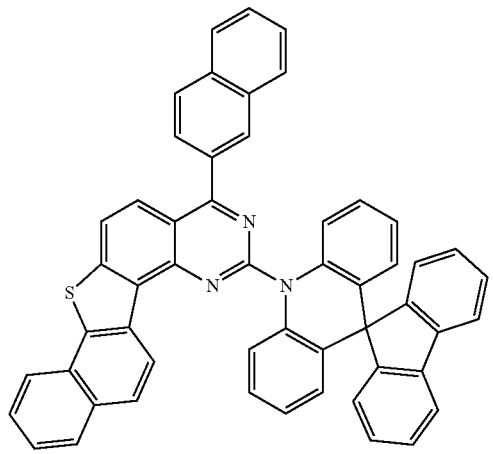
C143
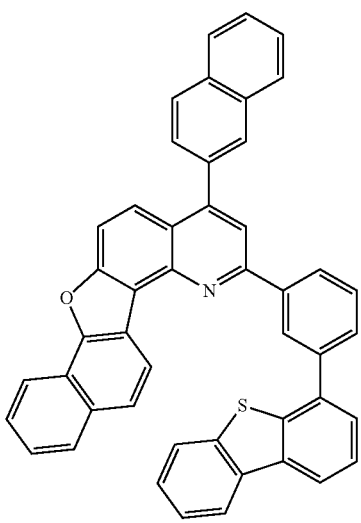
C141
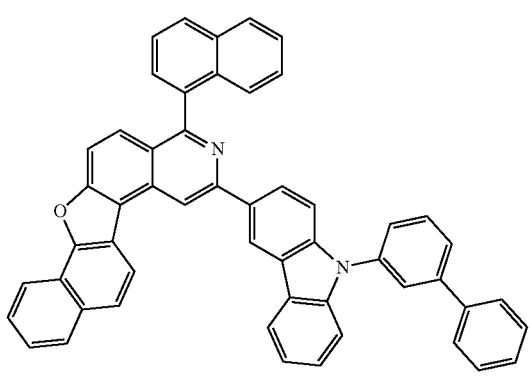
C144
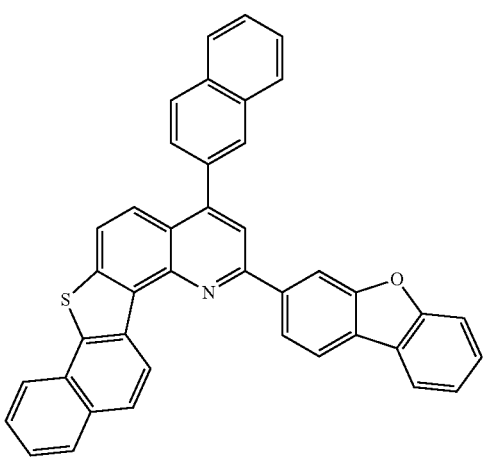
C142
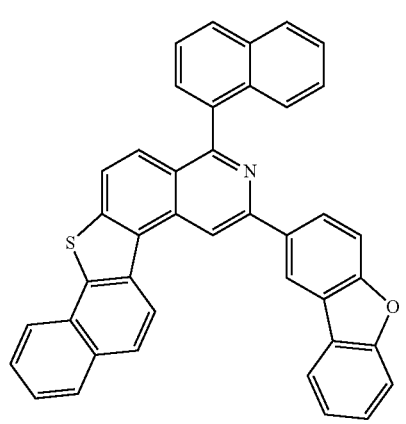
C145
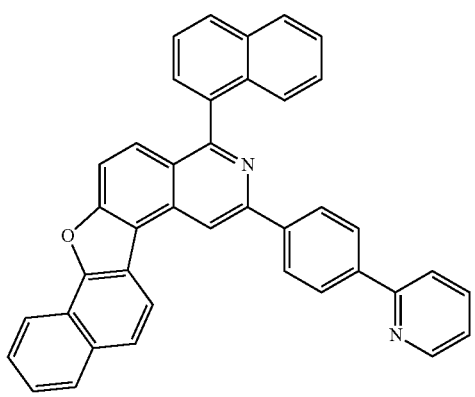

C146
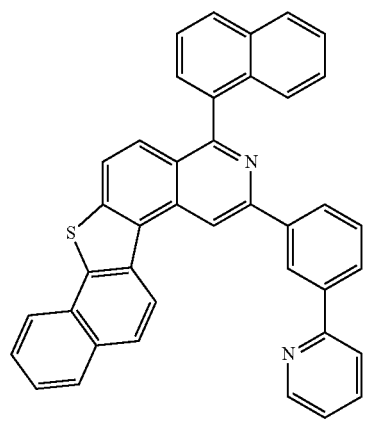
C149
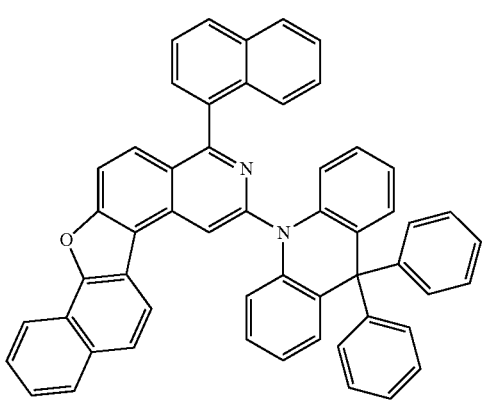
C147
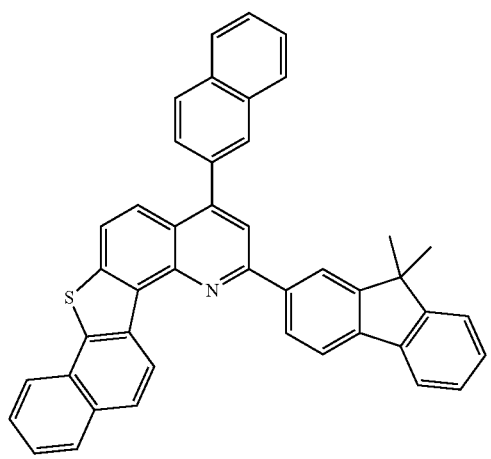
C150
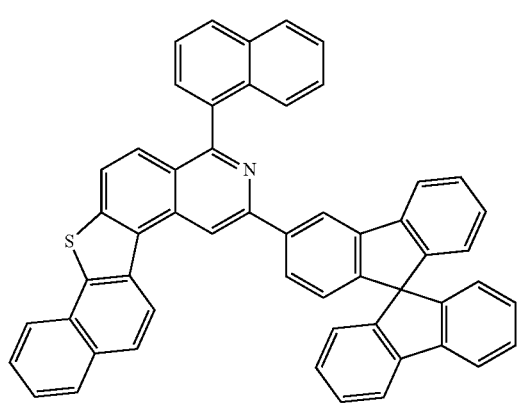
C148
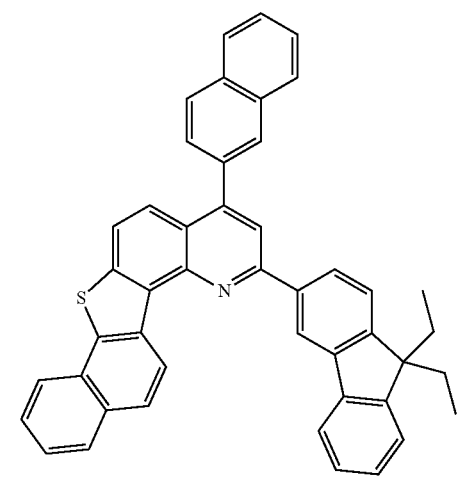
C151
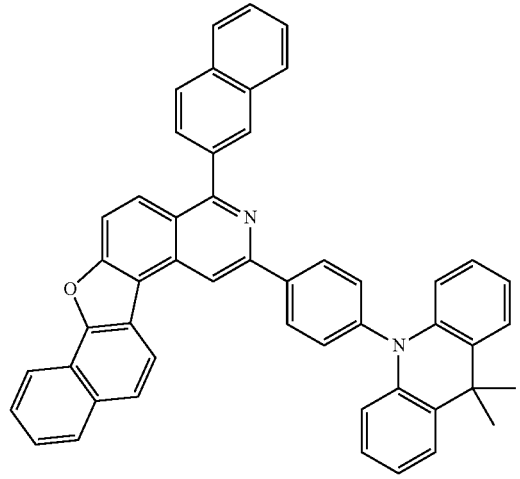

C152
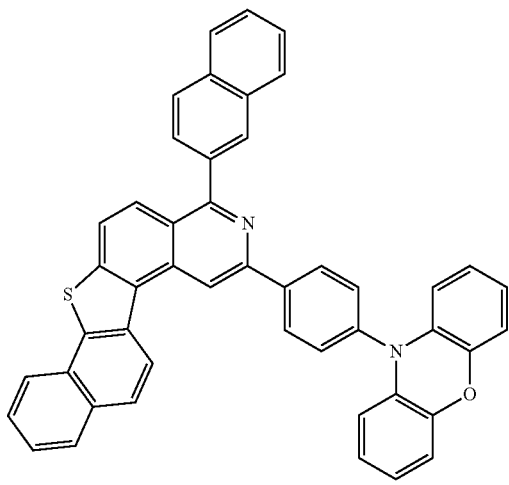
C153
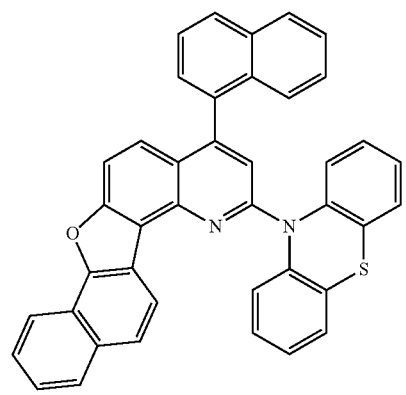
C154
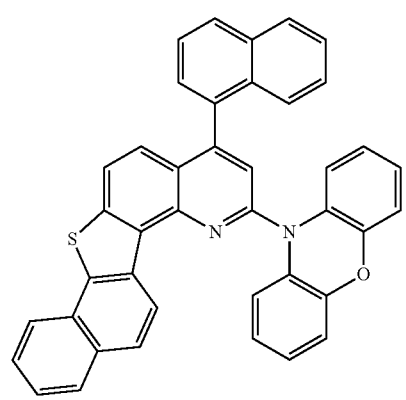
C155
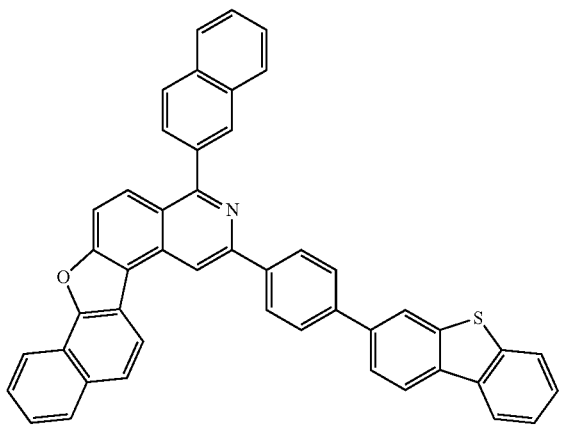
C156
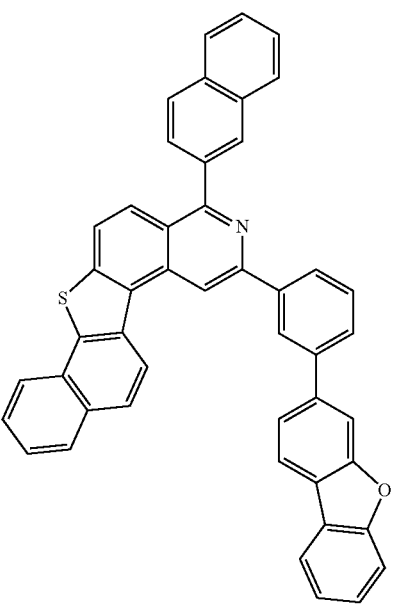
C157
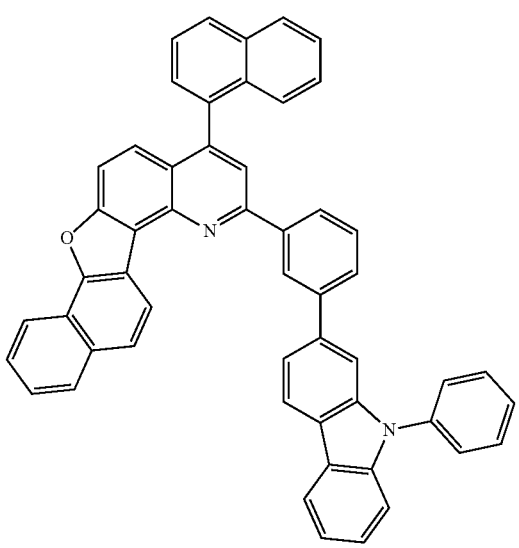

-continued
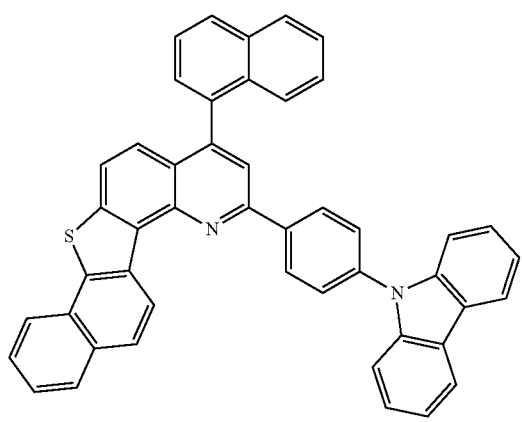
C158
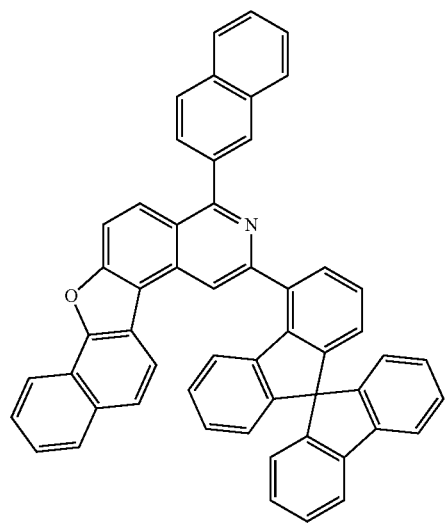
C159
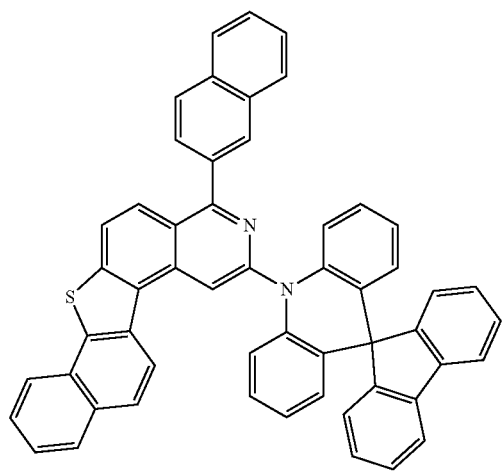
C160
-continued
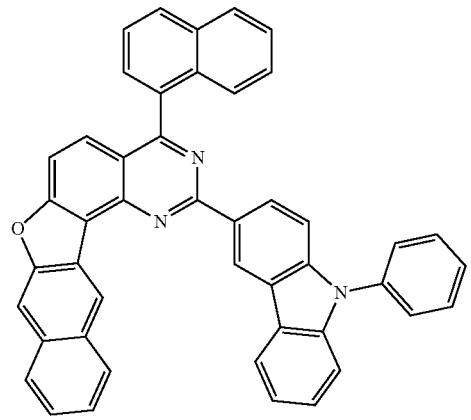
C161
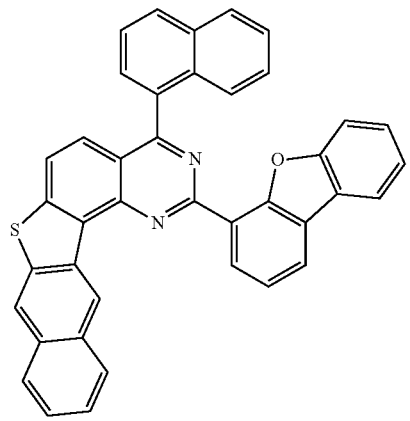
C162
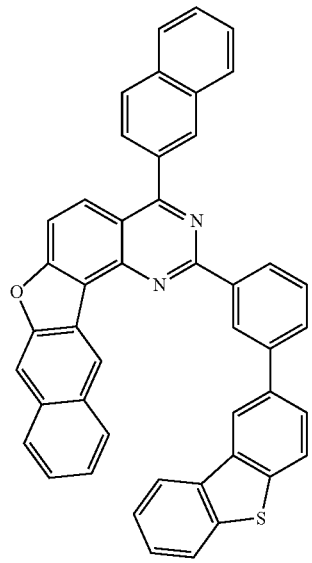
C163

-continued
C164
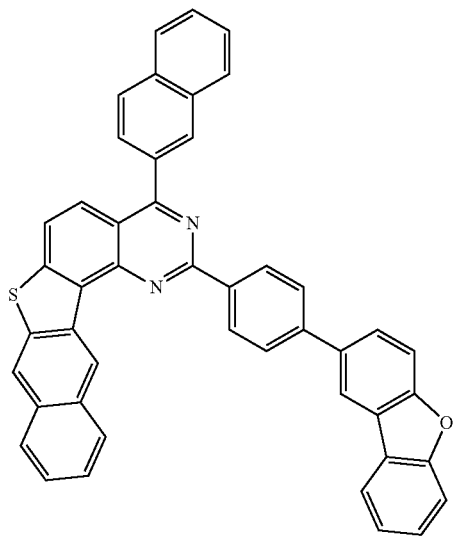
C165
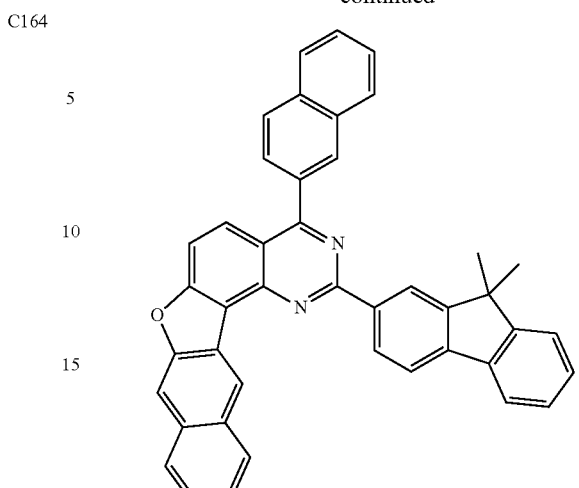
C167
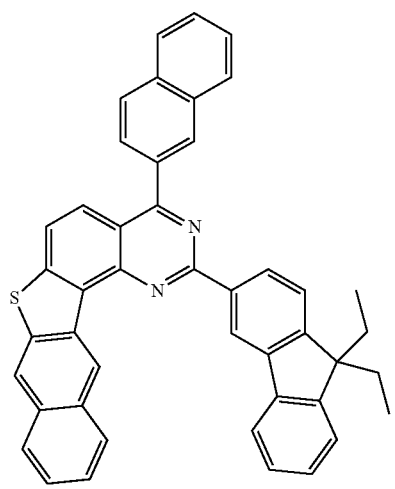
C168
C166
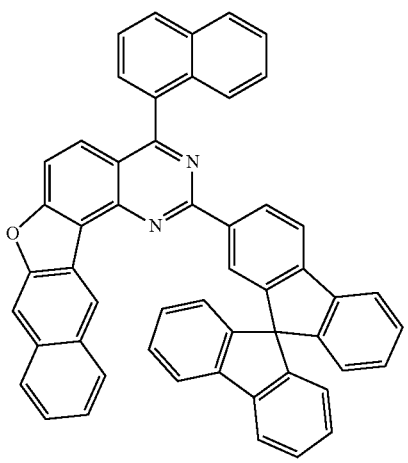
C169

C170
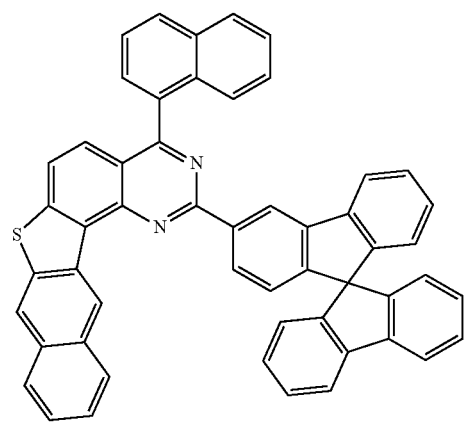
C173
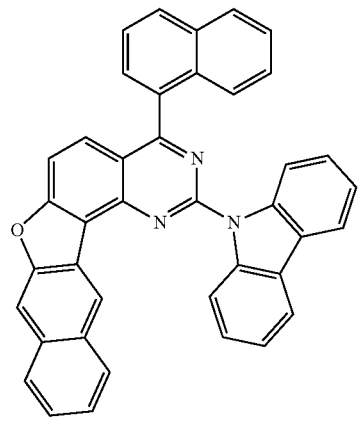
C171
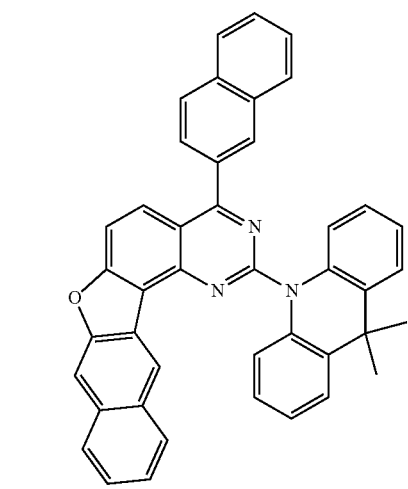
C174
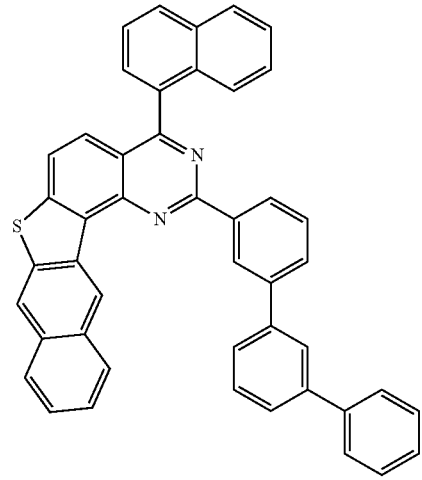
C172
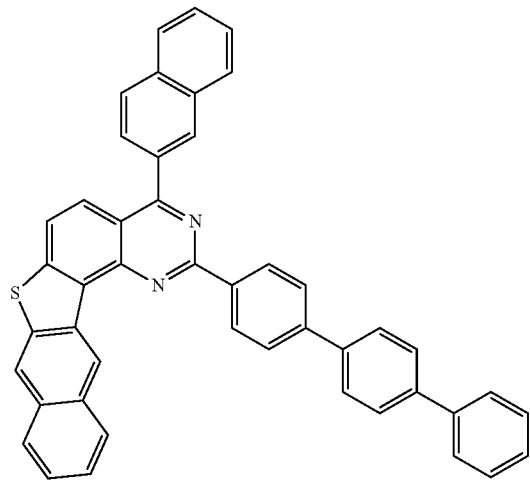
C175
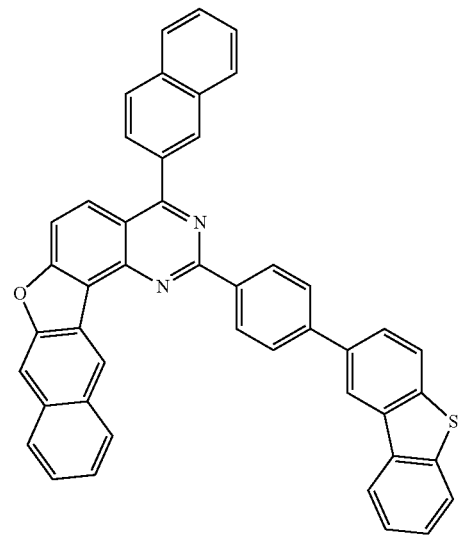

C176
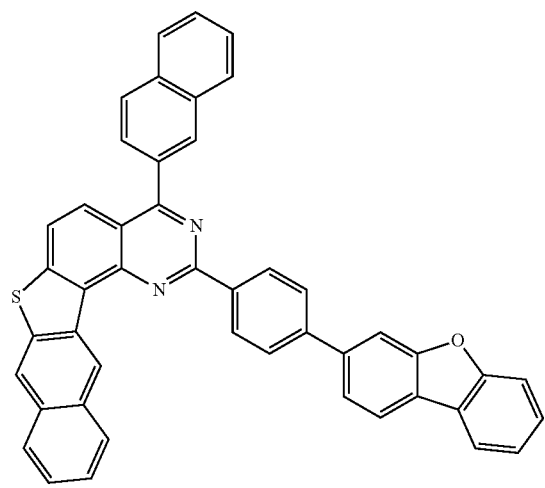
C177
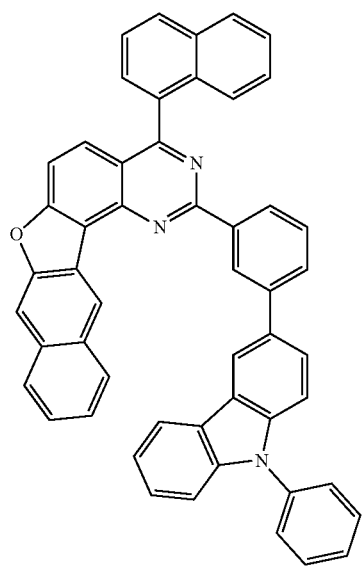
C178
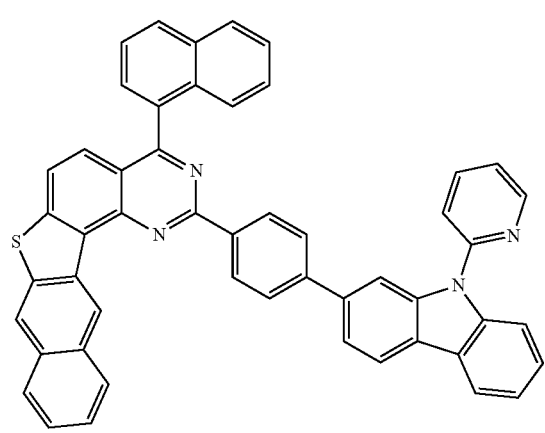
C179
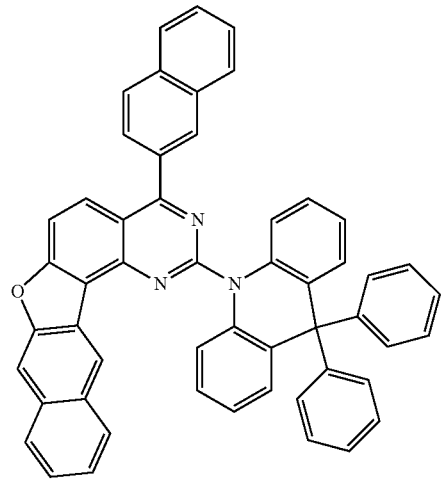
C180
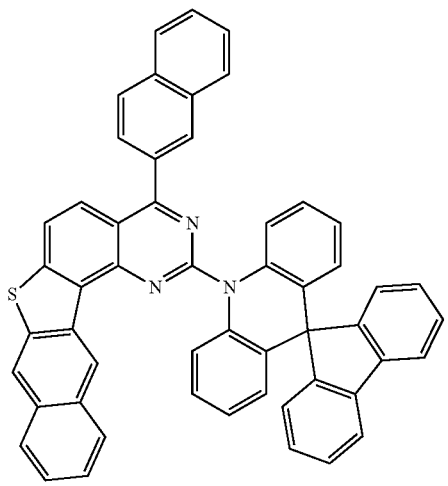
C181
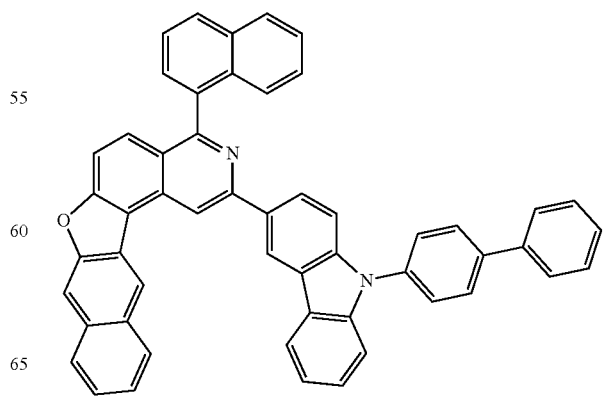

C182
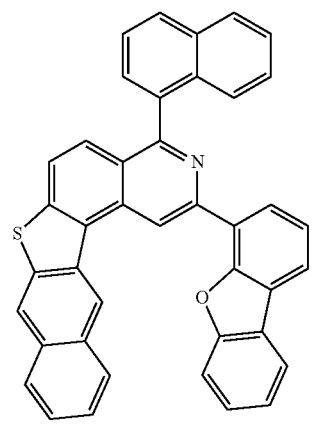
C185
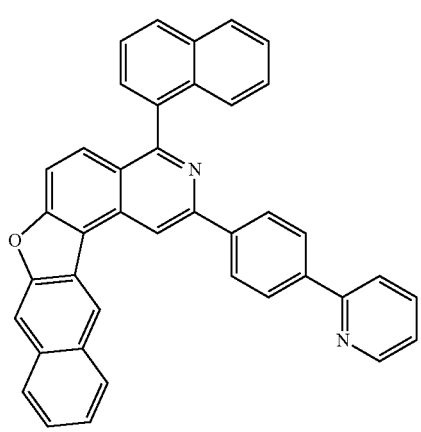
C183
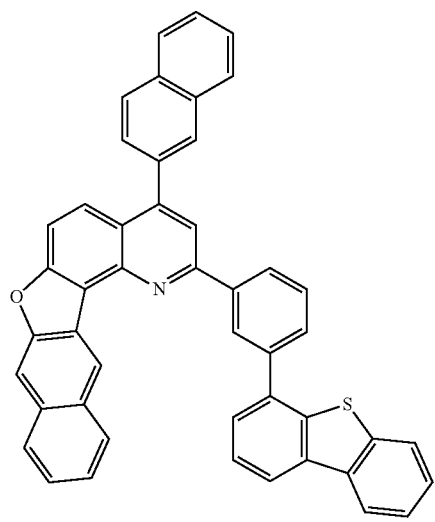
C186
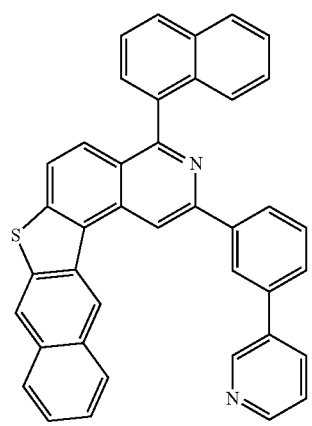
C184
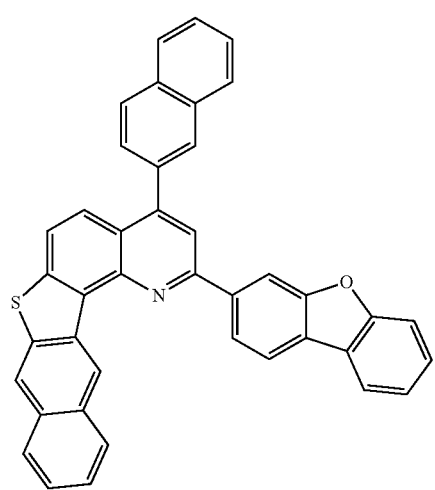
C187
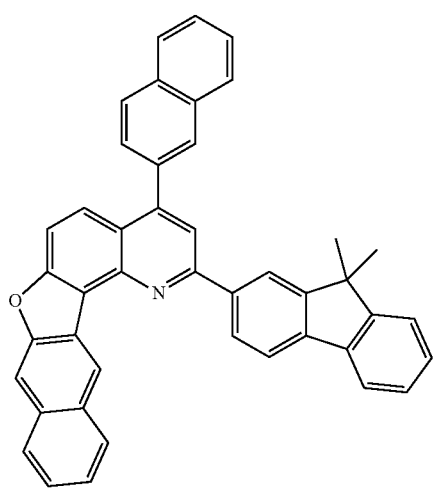

C188
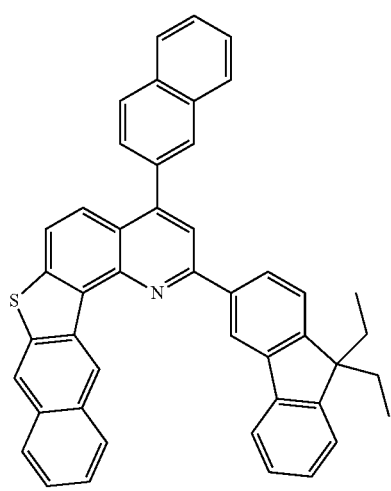
C189
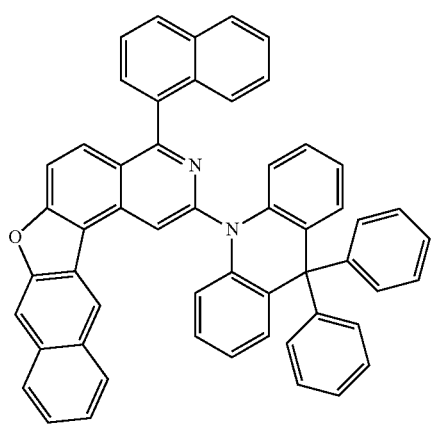
C190
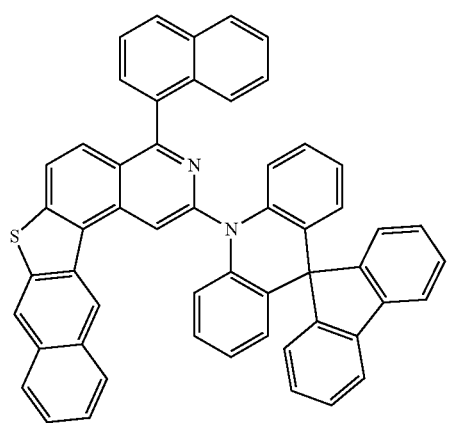
C191
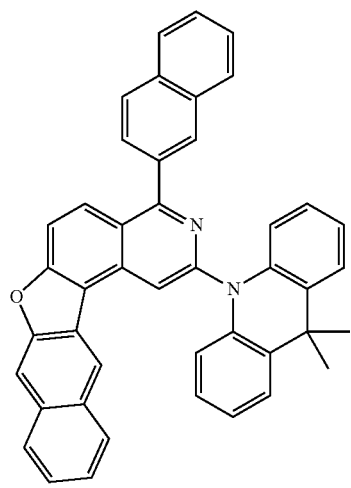
C192
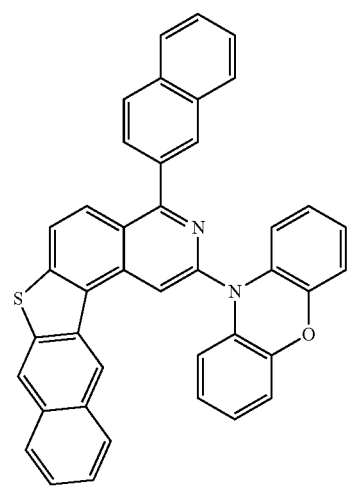
C193
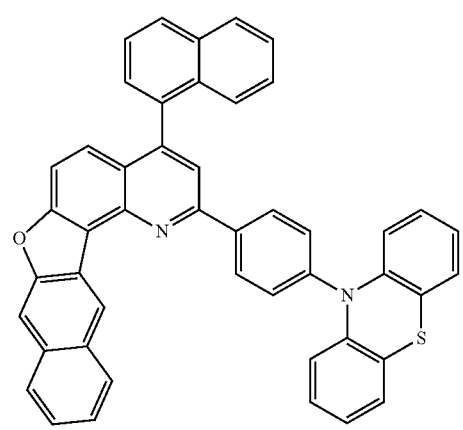

-continued
C194
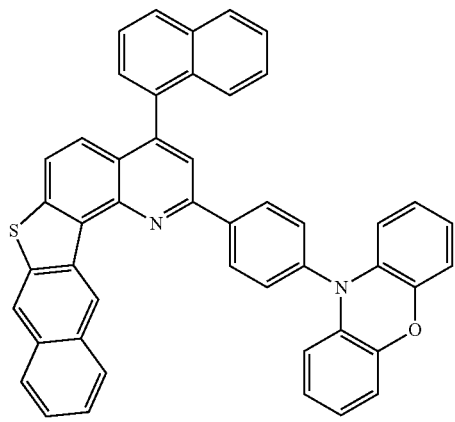
C195
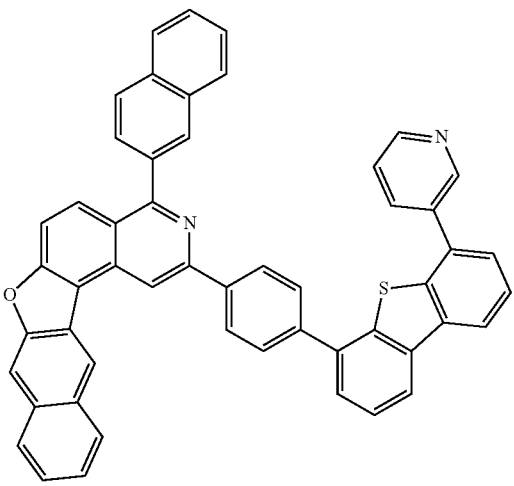
C196
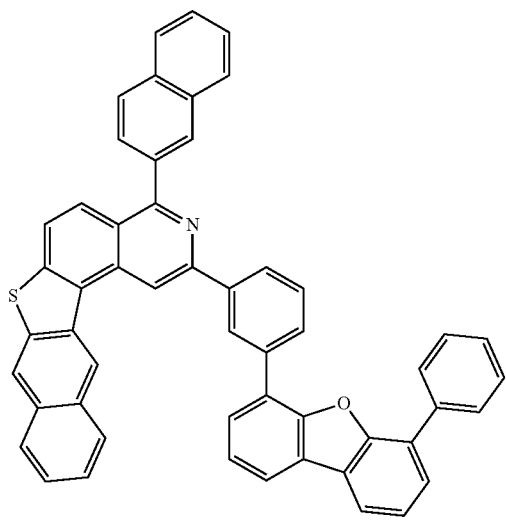
C197
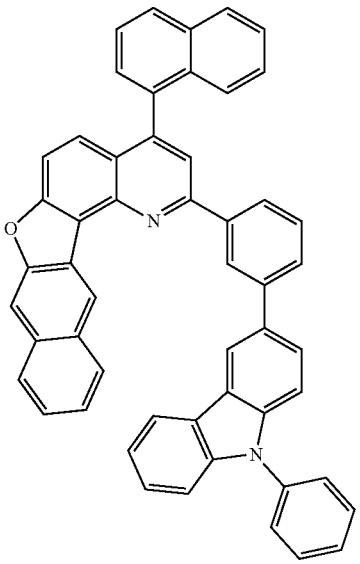
C198
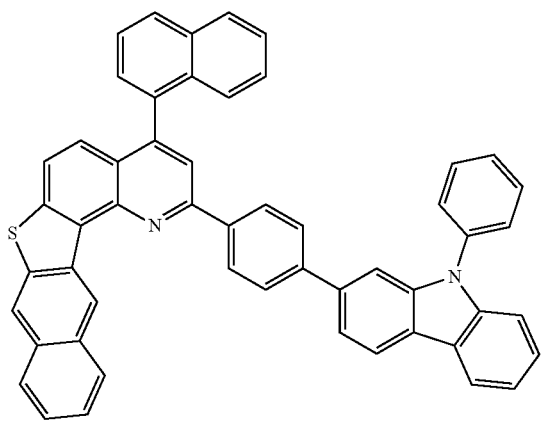
C199
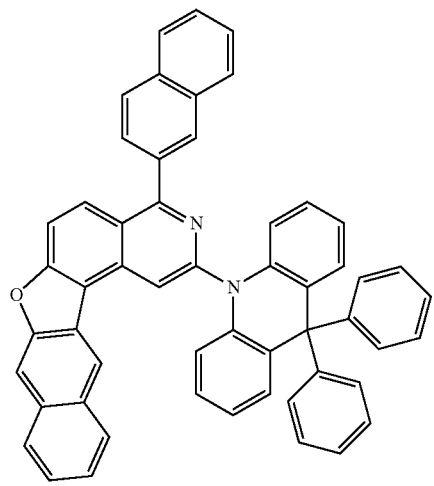

-continued
C200
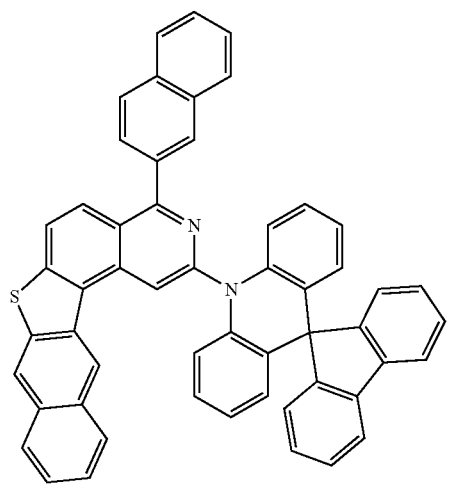
C201
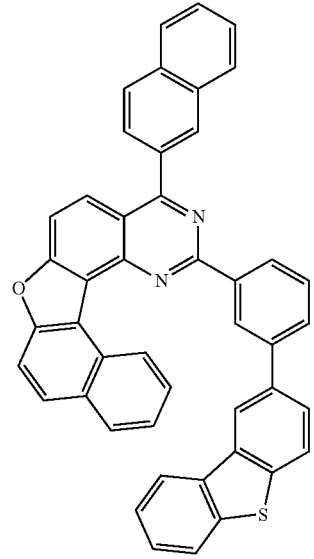
C202
C203
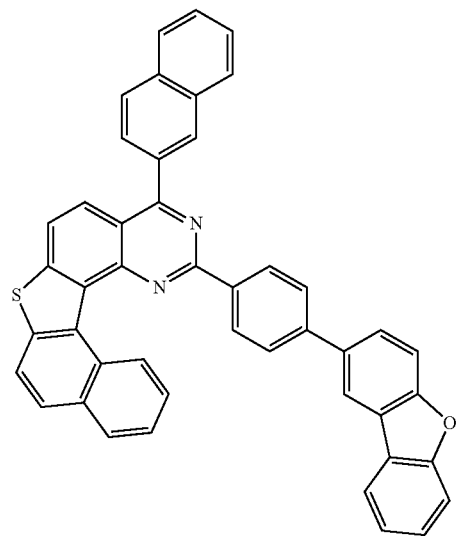
C204
C205
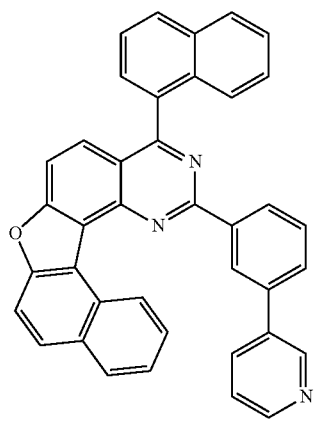

-continued
C206
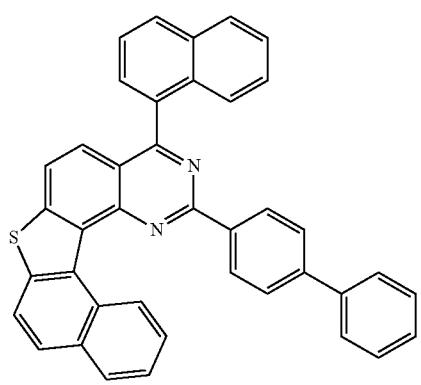
C207
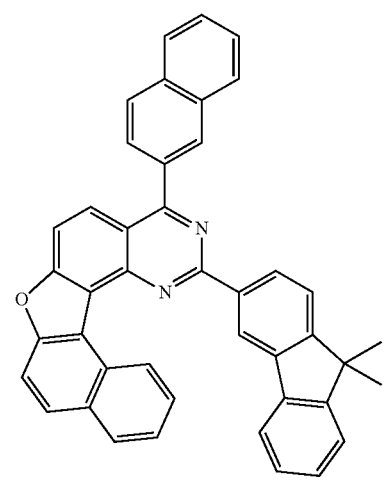
C208
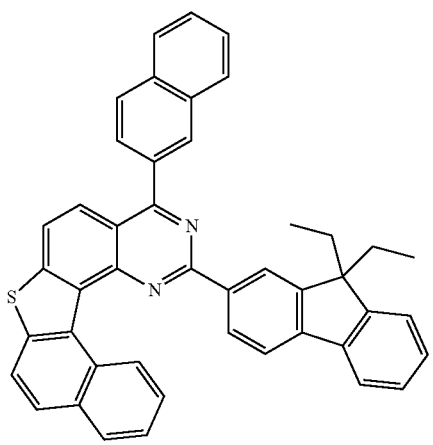
-continued
C209
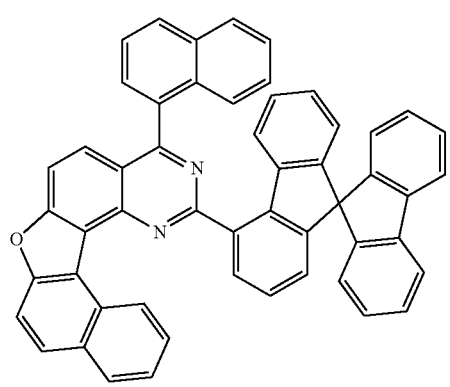
C210
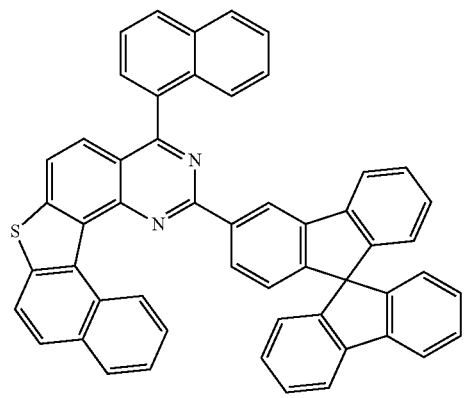
C211
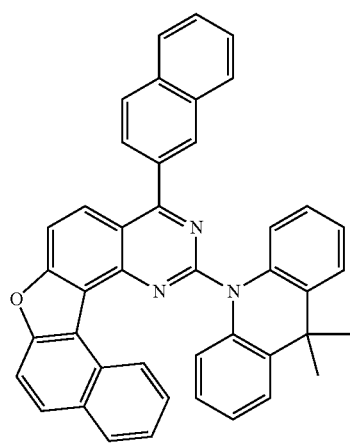
C212
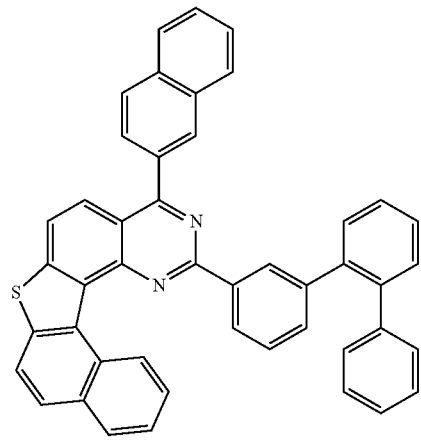

C213
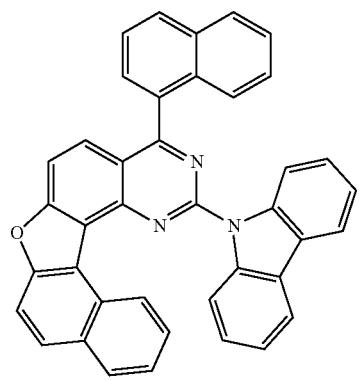
C214
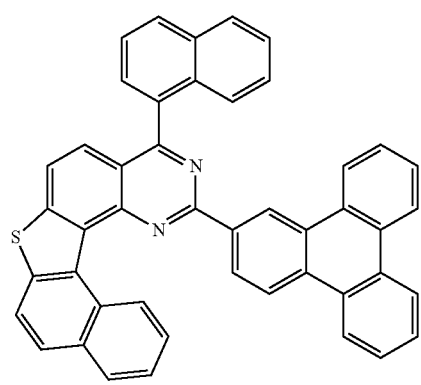
C215
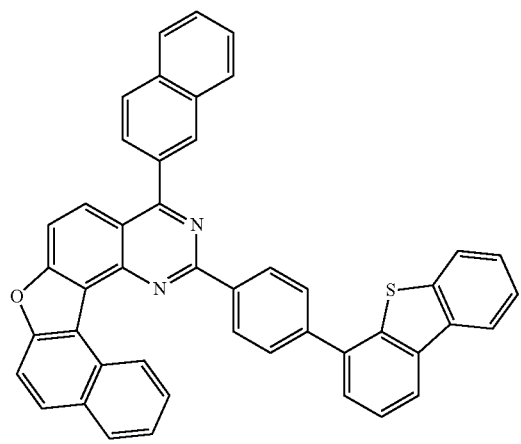
C216
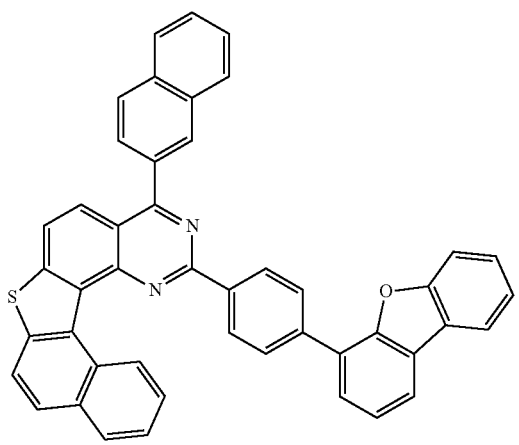
C217
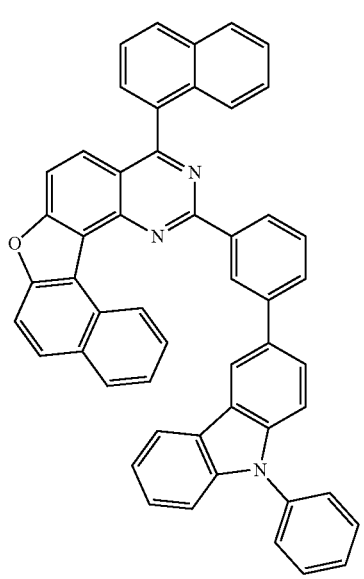
C218
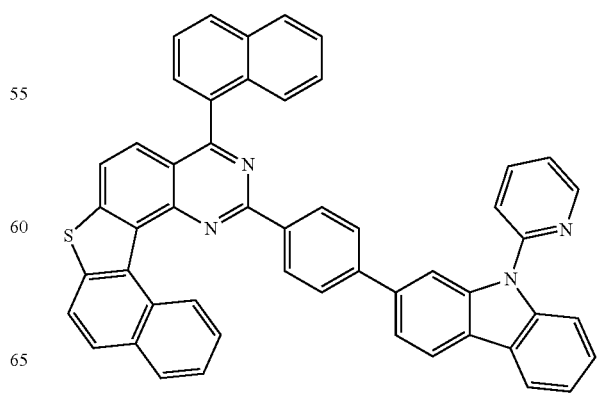

C219
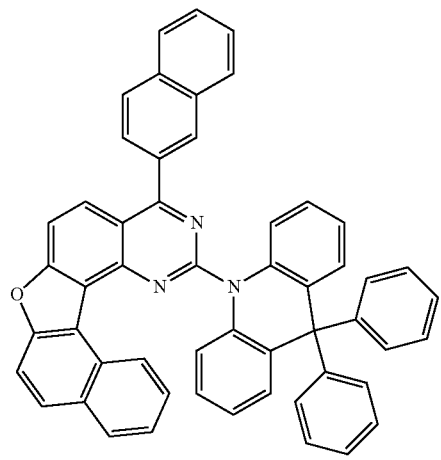
C220
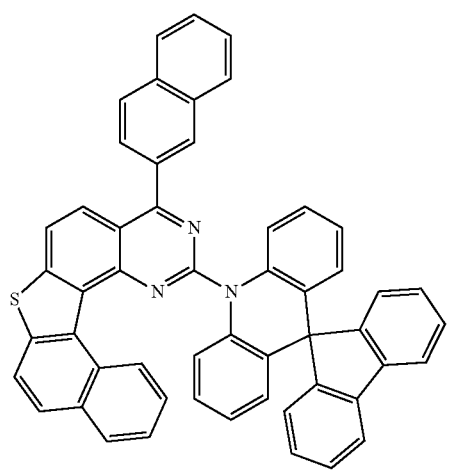
C221
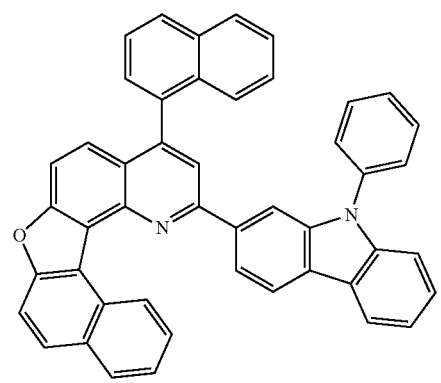
C222
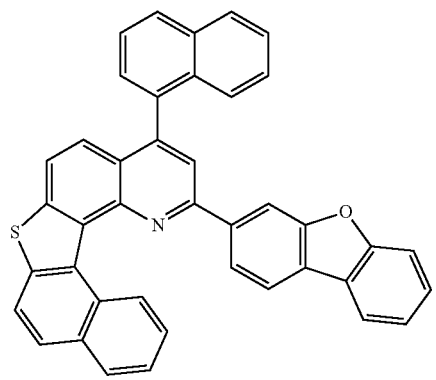
C223
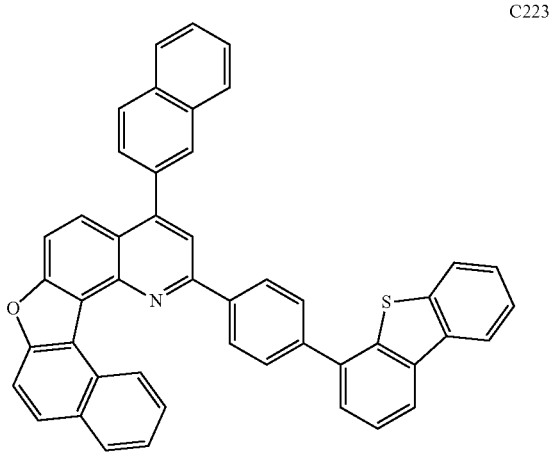
C224
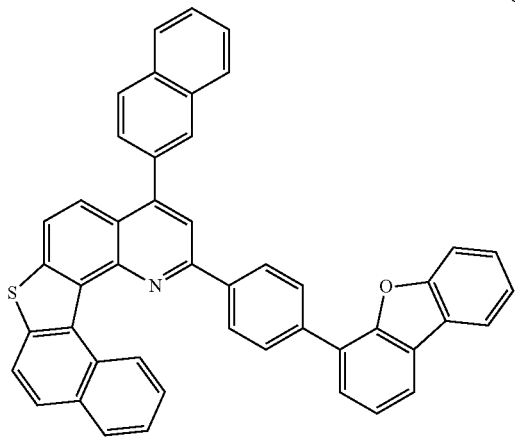
C225
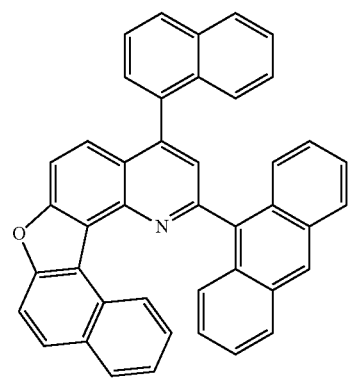

-continued
C226
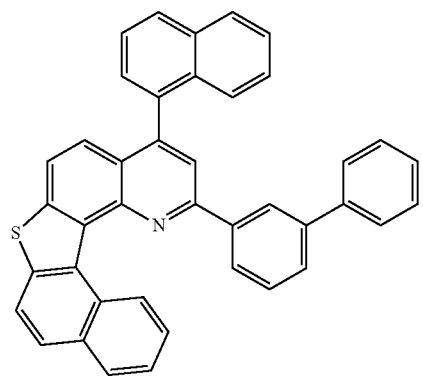
C227
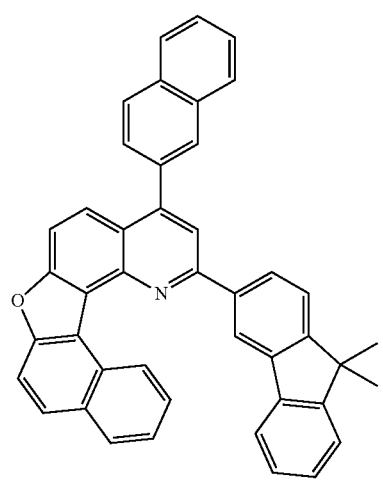
C228
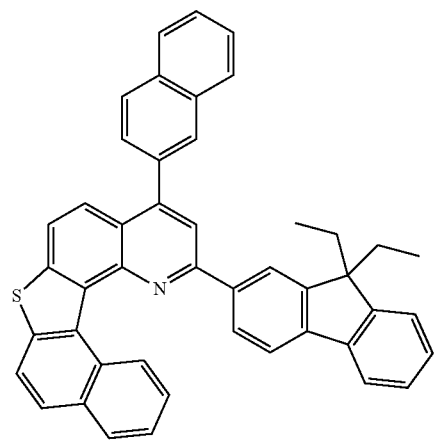
-continued
C229
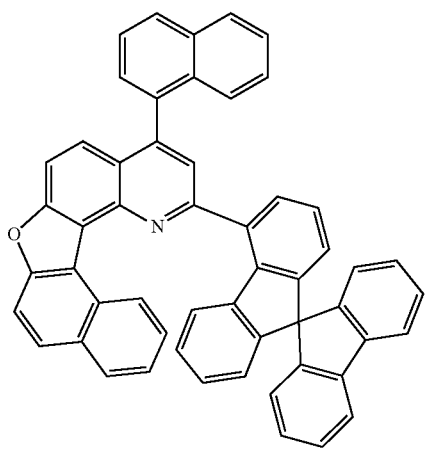
C230
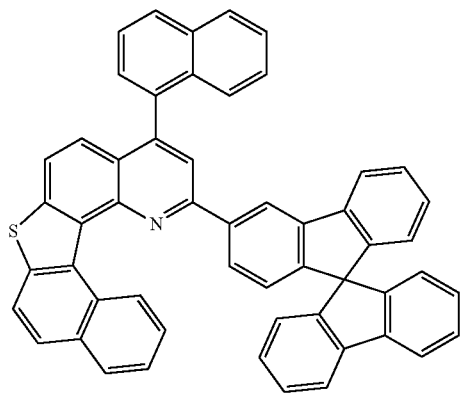
C231
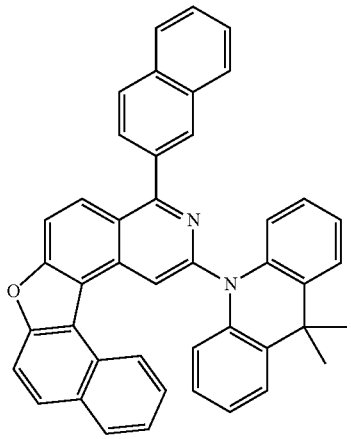

C232
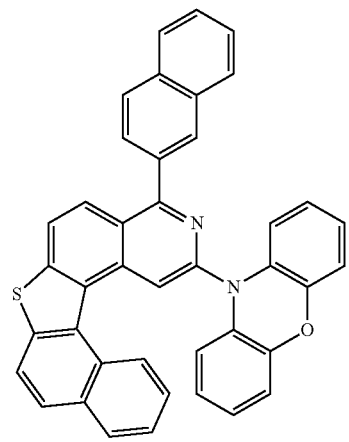
C235
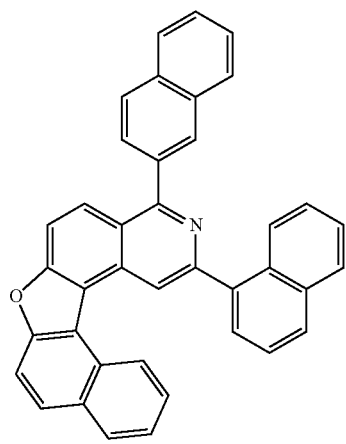
C233
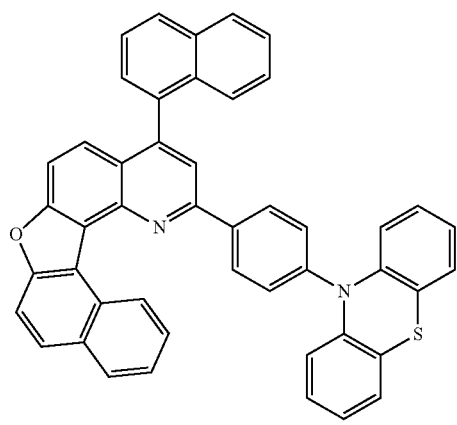
C236
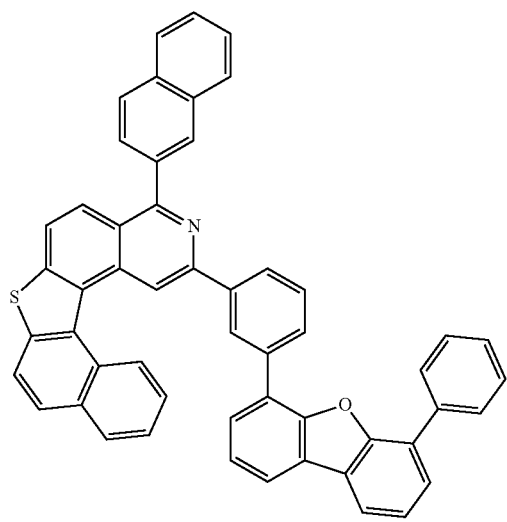
C234
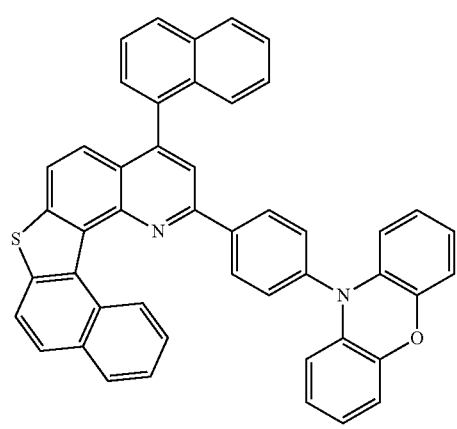
C237

-continued

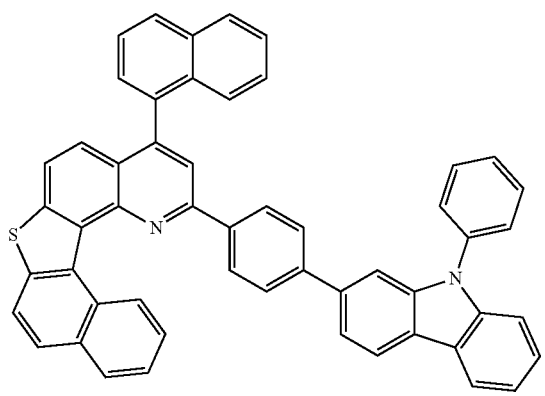

C238

C239

C240 and

In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. In particular, at least one of the light emitting layer and the organic thin film layer comprises the compound of formula (A).

In some embodiments, the light emitting layer comprising the compound of formula (A) is a host material.

In a further embodiment of the present invention, the organic electroluminescence device is a lighting panel. In other embodiment of the present invention, the organic electroluminescence device is a backlight panel.

Detailed preparation of the organic compounds of the present invention will be clarified by exemplary embodiments below, but the present invention is not limited thereto. EXAMPLES 1 to 18 show the preparation of the organic compounds of the present invention, and EXAMPLE 19 shows the fabrication and test reports of the organic EL devices.

Example 1

Synthesis of C1

Synthesis of Intermediate A

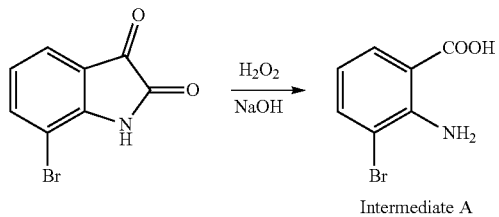

Intermediate A 4-bromoindoline-2,3-dione (25 g, 110.6 mmol) and 1.0M sodium hydroxide an aqueous solution (220 mL) were put in 1 L flask and then, stirred at 80° C. Under a nitrogen flow. Hydrogen peroxide (20%, 16.7 mL) was added thereto through a dropping funnel for 15 mins and the mixture was stirred at 80° C. for 1 hr. Subsequently, the reactant was cooled down to −10° C. and then, concentrated. HCl was slowly added thereto to adjust pH to 4~5, the reactant was concentrated again, methanol (400 mL) was added thereto, and the mixture was stirred for 15 mins and filtered. A filtrate therefrom was dried to give Intermediate A (23.9 g, 99%).

Synthesis of Intermediate B

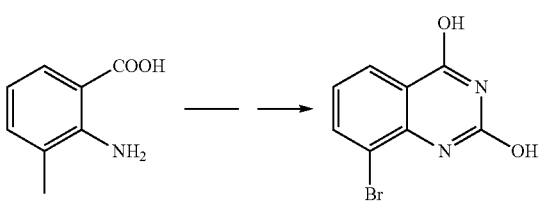

Intermediate B

Intermediate A (23.9 g, 110.6 mmol) and urea (66.3 g, 1106 mmol) were in 250 ml flask and then, heated at 180° C. for 16 hrs. when Intermediate A all disappeared, the temperature was a little lowered, o-dichlorobenzene (100 mL) was added to water (300 mL) and then, stirred therewith. A solid therefrom was filtered and dried to give Intermediate B (16 g, 60%).

Synthesis of Intermediate C

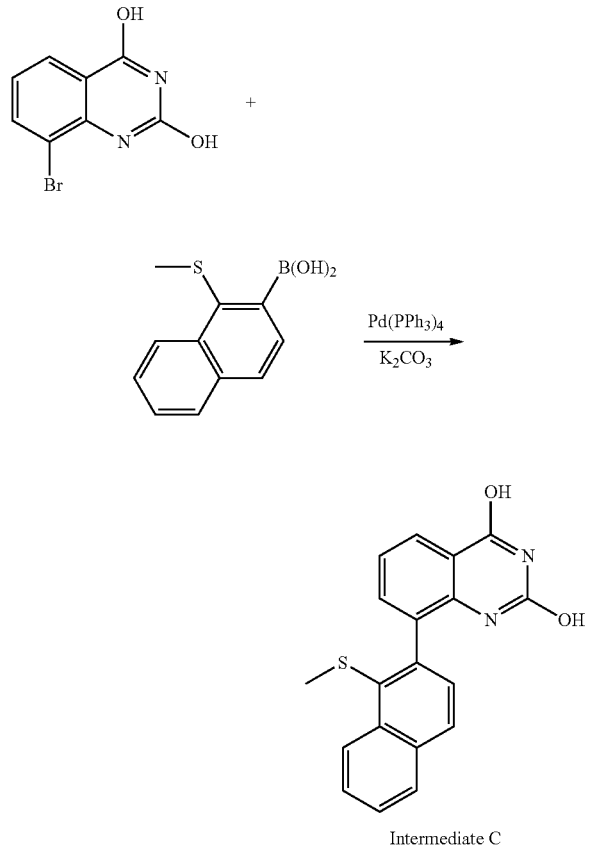

Intermediate C

Intermediate B (16 g, 66.4 mmol), (1-(methylthio)naphthalene-2-yl)boronic acid (15.9 g, 73 mmol), potassium carbonate (22.9 g, 166 mmol), Pd(PPh$_3$)$_4$ (3.8 g, 3.3 mmol) were added to THF (450 mL) and water (200 mL) in 1 L flask, and the mixture was heated at 70° C. stirred 16 hrs. After removing an aqueous layer, an organic layer remaining there was concentrated, extracted with DCM (300 mL), dried with MgSO$_4$, after removing the solvent, methanol was used for recrystallization obtain Intermediate C (14.4 g, 65%).

Synthesis of Intermediate D

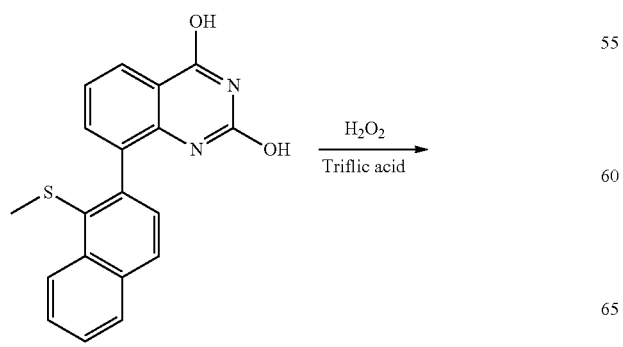

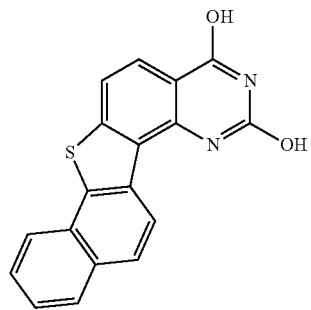

Intermediate D

Intermediate C (14.4 g, 43 mmol) was dissolved in glacial acetic acid (300 mL) in 1 L flask, and H$_2$O$_2$ (20%, 1 eq.) dissolved in lacial acetic acid was slowly added. The reactant was stirred at room temperature for 12 hrs, and after removing acetic acid. Subsequently, trifluorosulfonic acid was added thereto without additional purification, the obtained mixture was stirred at room temperature for 24 hrs. A K$_2$CO$_3$ aqueous solution was added to pH-4, methanol was used for recrystallization obtain Intermediate D (9.6 g, 70%).

Synthesis of Intermediate E

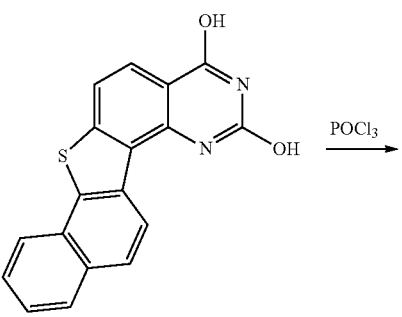

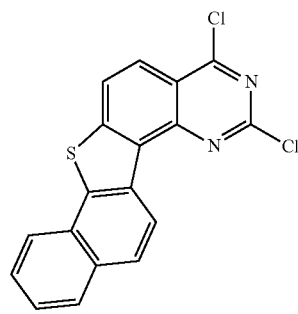

Intermediate E

Intermediate D (9.6 g, 30 mmol) was added to POCl$_3$ (34 mL, 360 mmol) in a 250 mL flask, and mixture was heated at 120° C. for 4 hrs. After cooled to room temperature, and was slowly poured into ice bath. Then a solid filtered therefrom was washed water and methanol, dried to obtain Intermediate E (9.6 g, 90%)

Synthesis of Intermediate F

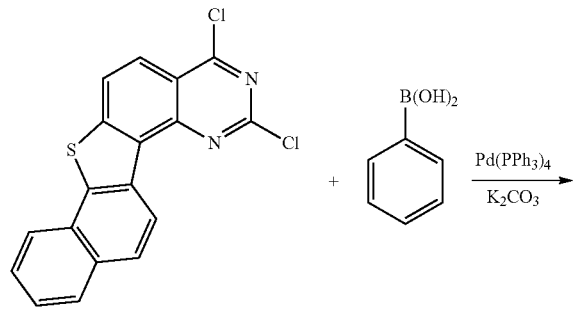

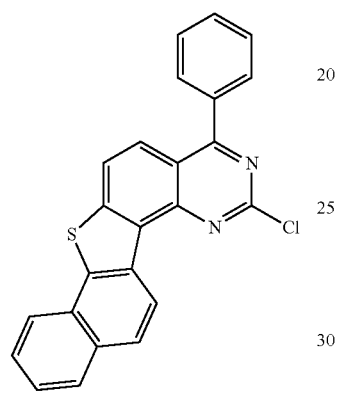

Intermediate F

Intermediate E (9.6 g, 27 mmol), phenylboronic acid (3.6 g, 29.7 mmol), potassium carbonate (9.4 g, 67.5 mmol), Pd(PPh$_3$)$_4$ (1 g, 0.9 mmol) were add to THF (100 mL) and water (50 mL) in 250 mL flask, and the mixture was heated at 70° C. stirred 16 hrs. After removing an aqueous layer, an organic layer remaining there was concentrated, extracted with DCM (300 mL), dried with MgSO$_4$, after removing the solvent, methanol was used for recrystallization obtain Intermediate F (7.3 g, 68%).

Synthesis of C1

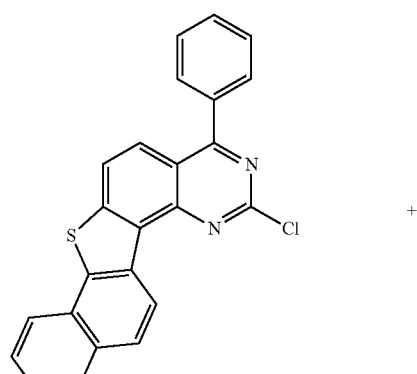

Intermediate F

Intermediate F (3 g, 7.55 mmol), 9-phenyl-3-(4,4,5,5-tetramethyl-1,3,2-dioxaborolan-2-yl)-9H-carbazole (3.07 g, 8.3 mmol), potassium carbonate (2.6 g, 18.87 mmol), Pd(PPh$_3$)$_4$ (0.3 g, 0.25 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C1 (3.42 g, 75%) as an off-white solid. MS (m/z, EI$^+$):603.74.

Example 2

Synthesis of C2

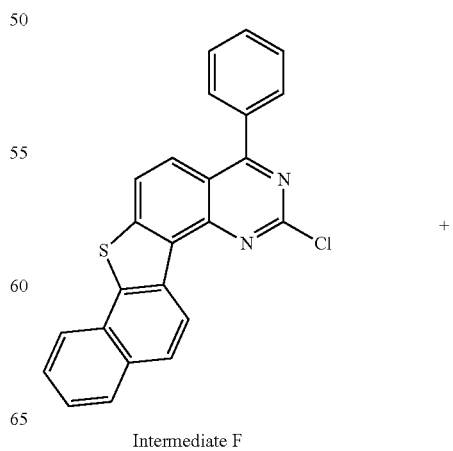

Intermediate F

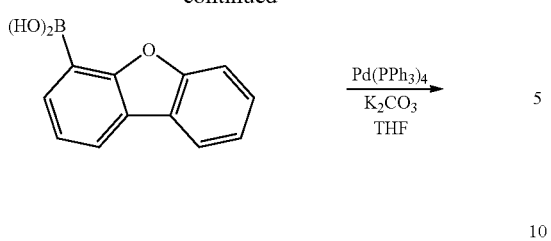

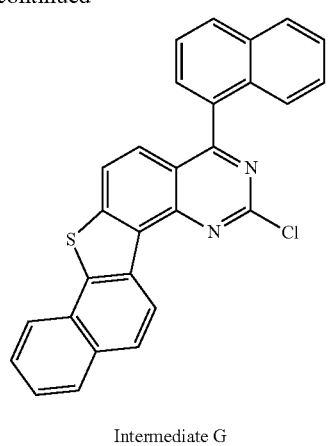

Intermediate G

The same synthesis procedure as in Synthesis of Intermediate F was used, except that 5.11 g of naphthalene-1-ylboronic acid was used instead of phenylboronic acid to obtain Intermediate G (7.85 g, 65%).

Synthesis of C126

The same synthesis procedure as in Synthesis of C1 was used, except that 1.76 g of dibenzofuran-4-ylboronic acid was used instead of 9-phenyl-3-(4,4,5,5-tetramethyl-1,3,2-dioxaborolan-2-yl)-9H-carbazole to obtain the desired compound C2 (3.07 g, 77%/o). MS (m/z, EI$^+$):528.63.

Example 3

Synthesis of C126

Synthesis of Intermediate G

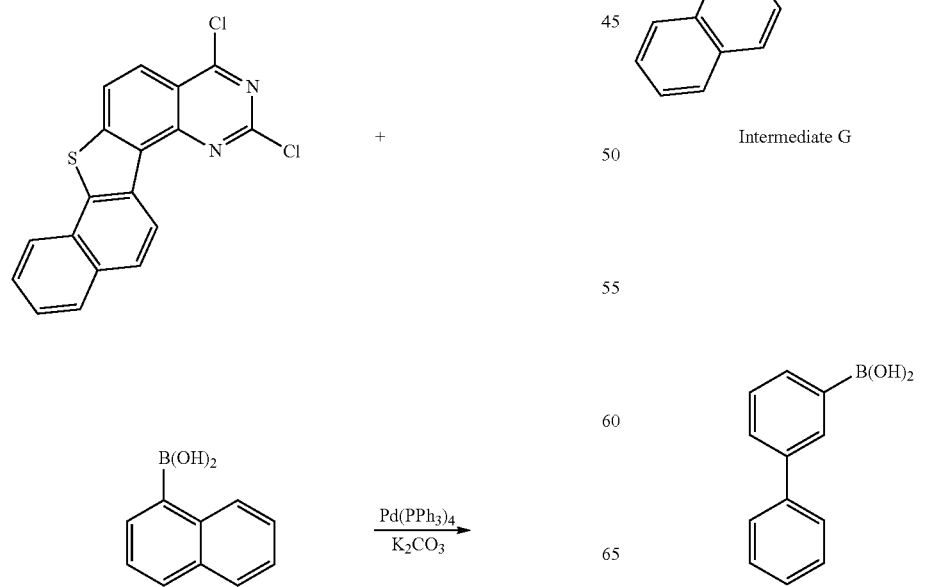

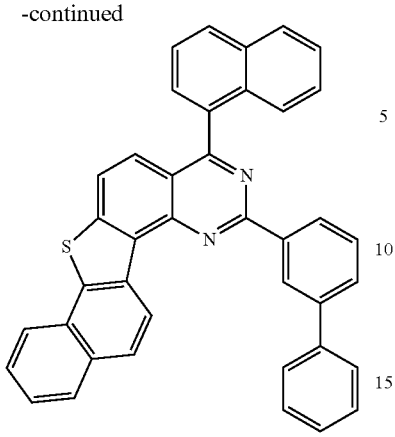

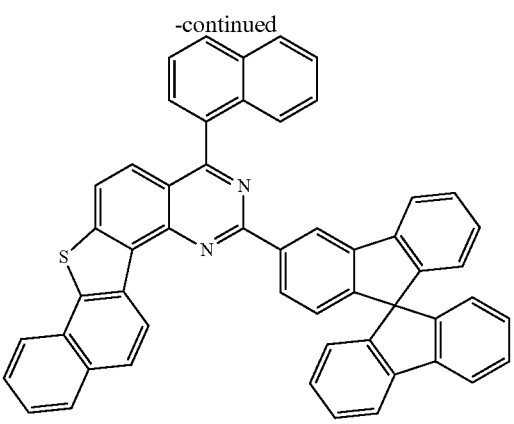

Intermediate G (3 g, 6.71 mmol), [1,1'-biphenyl]-3-ylboronic acid (1.46 g, 7.38 mmol), potassium carbonate (2.32 g, 16.78 mmol), Pd(PPh$_3$)$_4$ (0.23 g, 0.2 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C126 (2.62 g, 69%) as an off-white solid. MS (m/z, EI$^+$):564.71.

The same synthesis procedure as in Synthesis of C126 was used, except that 2.66 g of 9,9'-spirobi[fluoren]-3-ylboronic acid was used instead of naphthalene-1-ylboronic acid to obtain the desired compound C130 (3.66 g, 75%). MS (m/z, EI$^+$):726.9.

Example 5

Synthesis of C128

Synthesis of Intermediate H

Example 4

Synthesis of C130

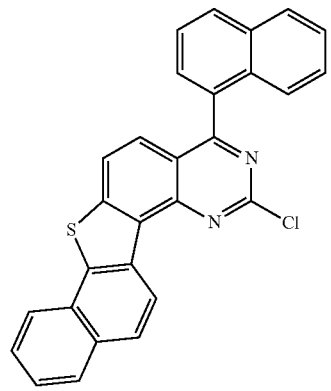

Intermediate G

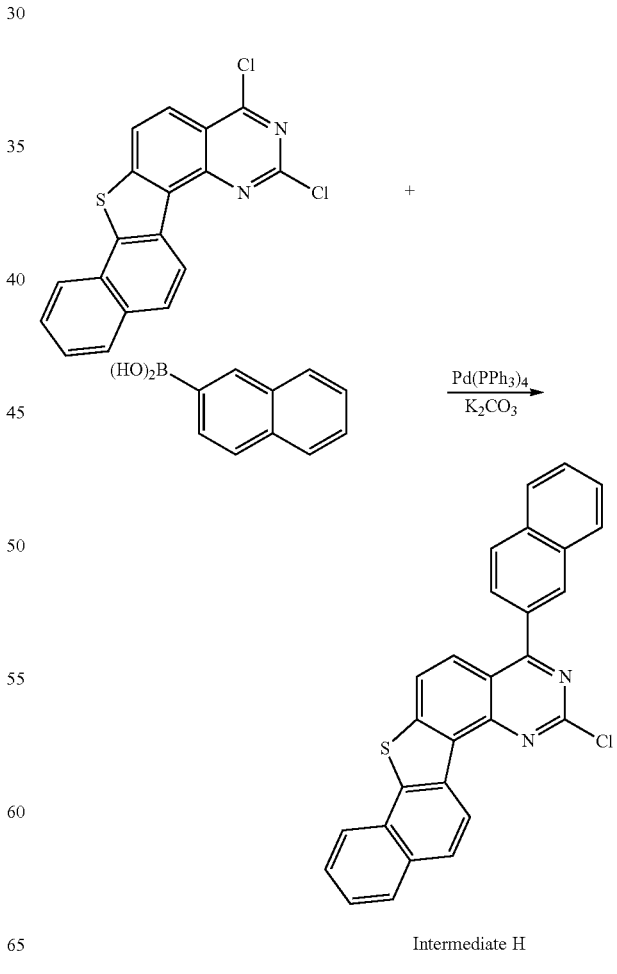

Intermediate H

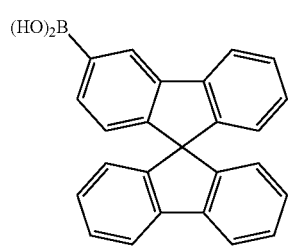

The same synthesis procedure as in Synthesis of Intermediate G was used, except that 5.11 g of naphthalene-2-ylboronic acid was used instead of naphthalene-1-ylboronic acid to obtain Intermediate H (8.21 g 68%).

Synthesis of C128

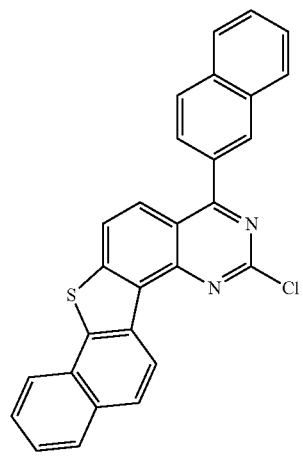

Intermediate H

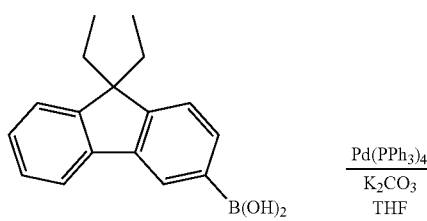

Intermediate H (3 g, 6.71 mmol), (9,9'-diethyl]-9H-fluoren-3-yl) boronic acid (1.97 g, 7.38 mmol), potassium carbonate (2.32 g, 16.78 mmol), Pd(PPh₃)₄ (0.23 g, 0.2 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C128 (3.05 g, 72%) as an off-white solid. MS (m/z, EI⁺):632.83.

Example 6

Synthesis of C132

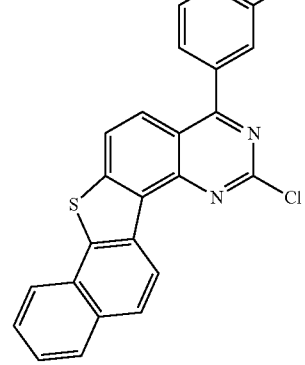

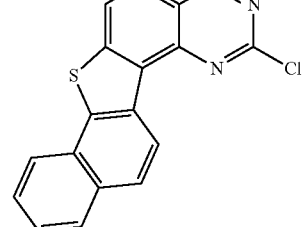

Intermediate H

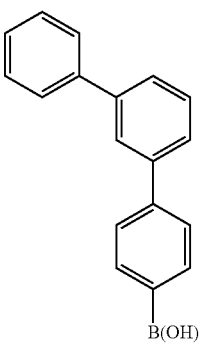

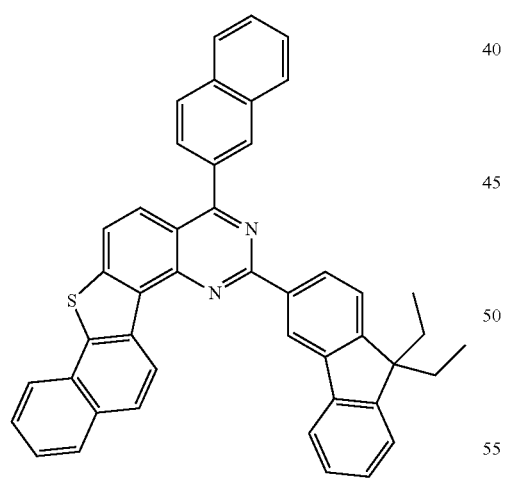

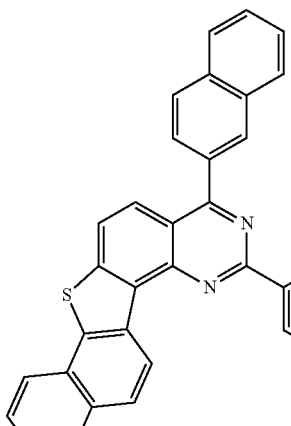

The same synthesis procedure as in Synthesis of C128 was used, except that 2.02 g of [1,1': 3',1''-terphenyl]-4-ylboronic acid was used instead of (9,9'-diethyl]-9H-fluoren-3-yl) boronic acid to obtain the desired compound C130 (3.35 g, 78%). MS (m/z, EI⁺):640.8.

Example 7

Synthesis of C56

Synthesis of Intermediate I

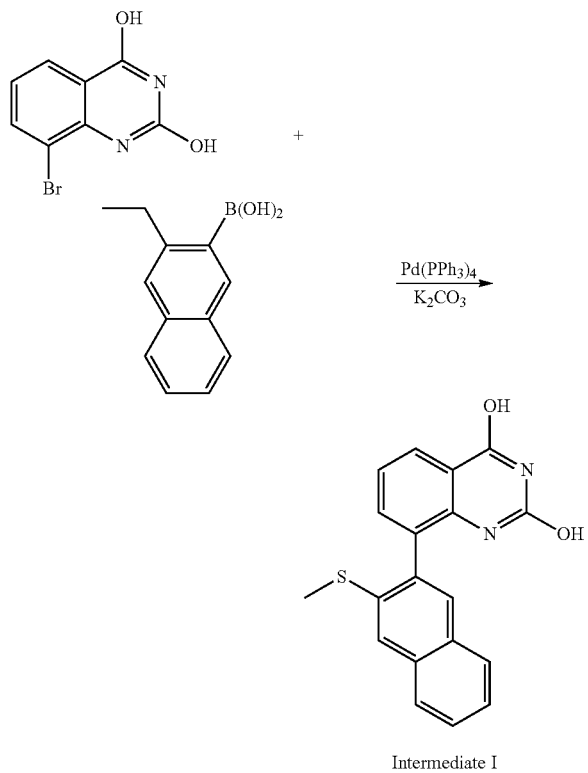

Intermediate I

Intermediate B (16 g, 66.4 mmol), (3-(methylthio)naphthalene-2-yl)boronic acid (15.9 g, 73 mmol), potassium carbonate (22.9 g, 166 mmol), Pd(PPh$_3$)$_4$ (3.8 g, 3.3 mmol) were add to THF (450 mL) and water (200 mL) in 1 L flask, and the mixture was heated at 70° C. stirred 16 hrs. After removing an aqueous layer, an organic layer remaining there was concentrated, extracted with DCM (300 mL), dried with MgSO$_4$, after removing the solvent, methanol was used for recrystallization obtain Intermediate I (15.7 g, 71%).

Synthesis of Intermediate J

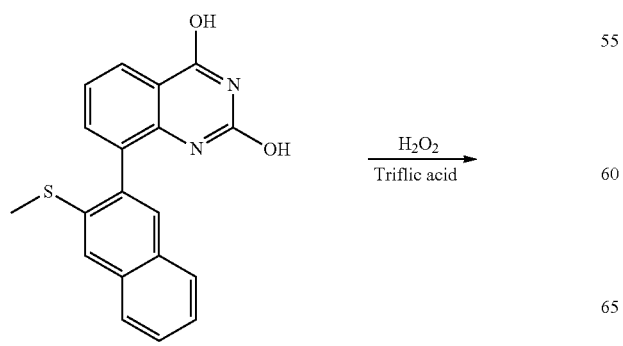

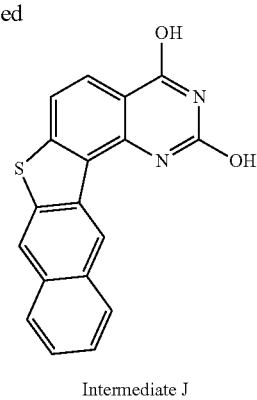

Intermediate J

Intermediate I (15.7 g, 46.95 mmol) was dissolved in glacial acetic acid (300 mL) in 1 L flask, and H$_2$O$_2$ (20%, 1 eq.) dissolved in lacial acetic acid was slowly added. The reactant was stirred at room temperature for 12 hrs, and after removing acetic acid. Subsequently, trifluorosulfonic acid was added thereto without additional purification, the obtained mixture was stirred at room temperature for 24 hrs. A K$_2$CO$_3$ aqueous solution was added to pH-4, methanol was used for recrystallization obtain Intermediate J (10.76 g, 72%).

Synthesis of Intermediate K

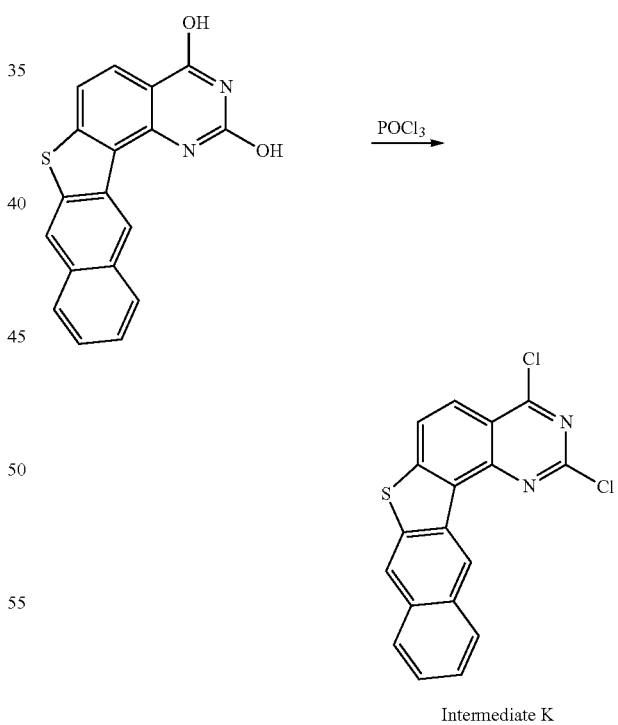

Intermediate K

Intermediate J (10.76 g, 33.8 mmol) was added to POCl$_3$ (38 mL, 405 mmol) in a 250 mL flask, and mixture was heated at 120° C. for 4 hrs. After cooled to room temperature, and was slowly poured into ice bath. Then a solid filtered therefrom was washed water and methanol, dried to obtain Intermediate K (10.92 g, 91%).

Synthesis of Intermediate L

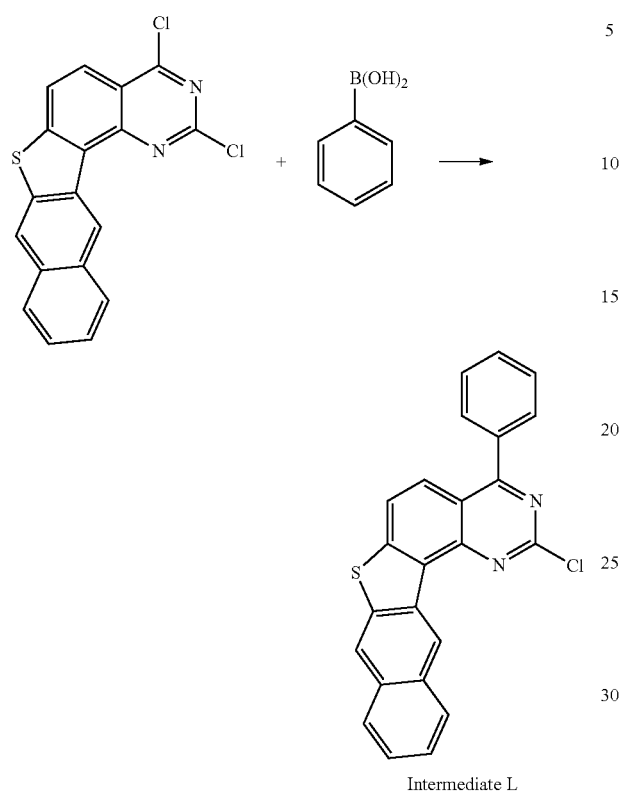

Intermediate L

Intermediate K (10.92 g, 30.7 mmol), phenylboronic acid (4.12 g, 33.8 mmol), potassium carbonate (10.6 g, 76.75 mmol), Pd(PPh$_3$)$_4$ (1.18 g, 1.02 mmol) were add to THF (100 mL) and water (50 mL) in 250 mL flask, and the mixture was heated at 70° C. stirred 16 hrs. After removing an aqueous layer, an organic layer remaining there was concentrated, extracted with DCM (300 mL), dried with MgSO$_4$, after removing the solvent, methanol was used for recrystallization obtain Intermediate F (8.66 g, 71%).

Synthesis of C56

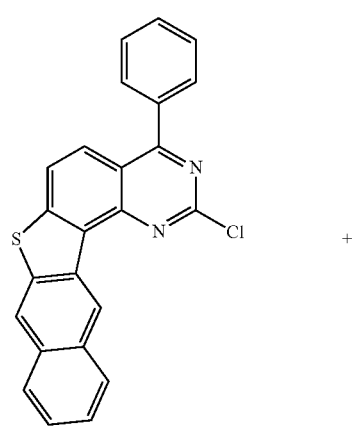

Intermediate L

+

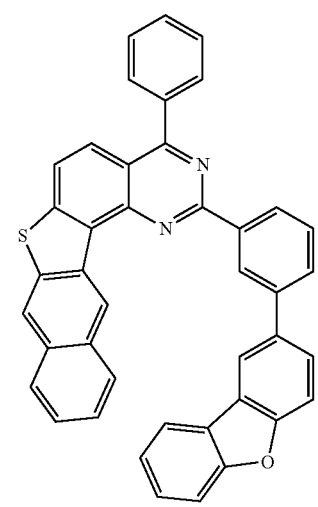

Intermediate L (3 g, 7.56 mmol), (3-(dibenzofuran-2-yl)phenyl) boronic acid (2.4 g, 8.31 mmol), potassium carbonate (2.6 g, 18.9 mmol), Pd(PPh$_3$)$_4$ (0.28 g, 0.25 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C56 (3.42 g, 75%) as an off-white solid. MS (m/z, EI$^+$):604.73.

Example 8

Synthesis of C60

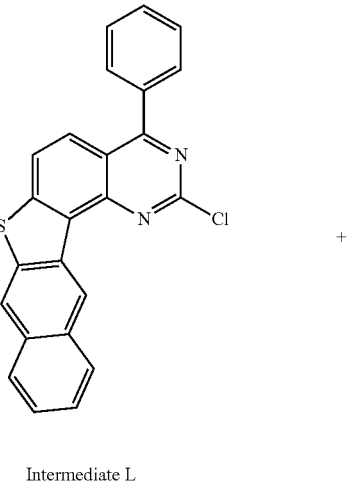

Intermediate L

+

101

-continued

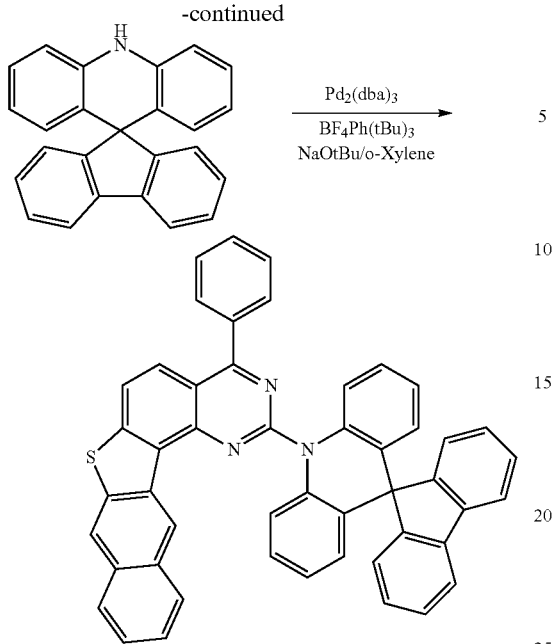

In a 100 ml three-necked flask that had been degassed and filled with nitrogen, 3 g (7.55 mmol) of Intermediate L, 2.75 g (8.3 mmol) of 10H-spiri[acridine-9,9'-fluorene], 0.14 g (0.151 mmol) of Pd$_2$(dba)$_3$, 0.09 g (0.302 mmol) of tri-tert-butylphosphonium tetrafluoroborate, 1.5 g (15.1 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C60 (3.592 g, 75%) as an off-white solid. MS (m/z, EI$^+$):691.85.

Example 9

Synthesis of C178

Synthesis of Intermediate M

102

-continued

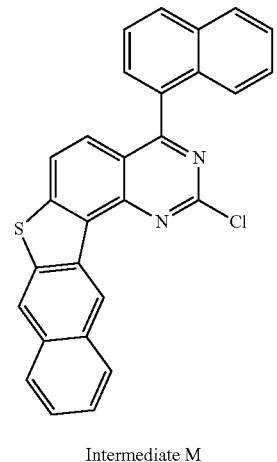

Intermediate M

The same synthesis procedure as in Synthesis of Intermediate L was used, except that 5.11 g of naphthalene-1-ylboronic acid was used instead of phenylboronic acid to obtain Intermediate M (8.21 g, 68%).

Synthesis of C178

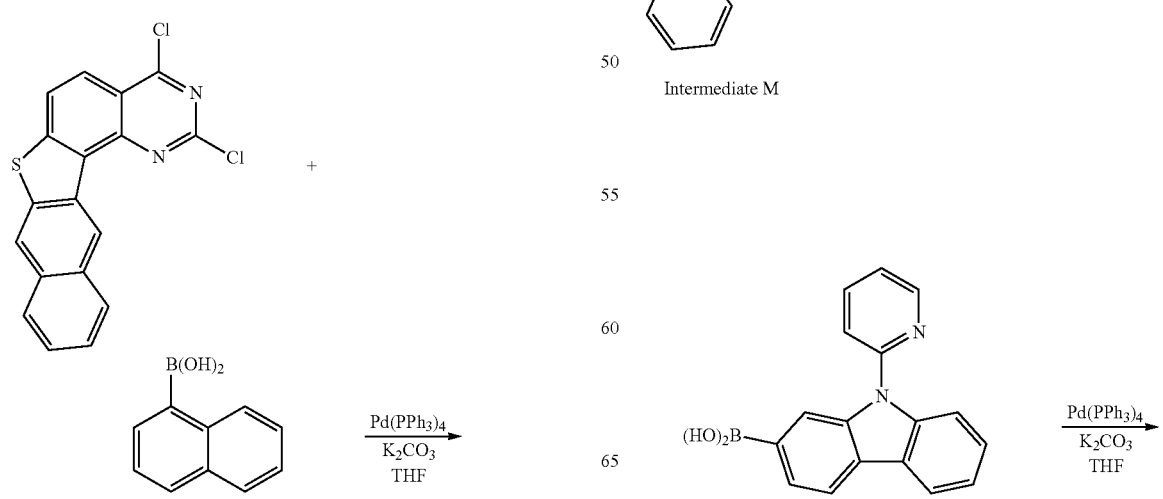

Intermediate M

103
-continued

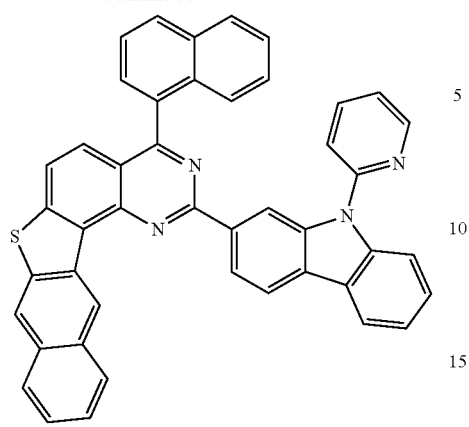

104
-continued

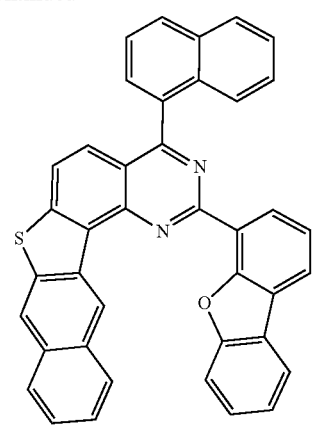

Intermediate L (3 g, 6.71 mmol), (9-(pyridine-2-yl)-9H-carbazol-2-yl) boronic acid (2.12 g, 7.38 mmol), potassium carbonate (2.32 g, 16.7 mmol), Pd(PPh$_3$)$_4$ (0.26 g, 0.22 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C178 (3.25 g, 74%) as an off-white solid. MS (m/z, EI$^+$):654.79.

The same synthesis procedure as in Synthesis of C178 was used, except that 1.56 g of dibenzofuran-4-ylboronic acid was used instead of (9-(pyridine-2-yl)-9H-carbazol-2-yl) boronic acid to obtain the desired compound C182 (3.1 g, 80%). MS (m/z, EI$^+$):578.69.

Example 10

Synthesis of C182

Example 11

Synthesis of C192

Synthesis of Intermediate N

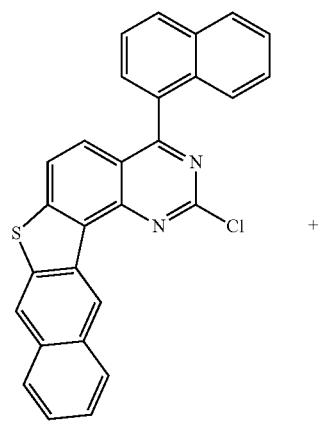

Intermediate M

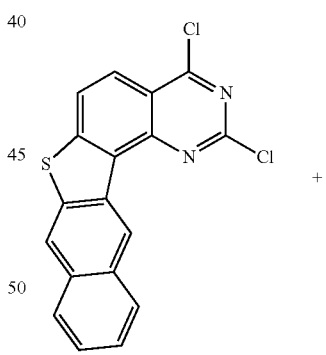

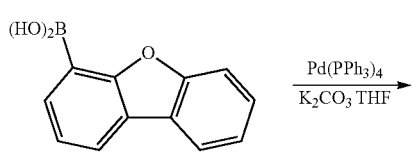

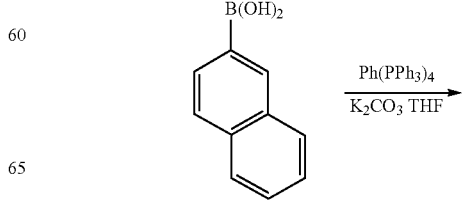

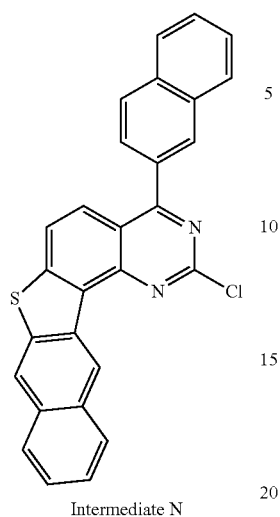

Intermediate N

The same synthesis procedure as in Synthesis of Intermediate M was used, except that 5.11 g of naphthalene-2-ylboronic acid was used instead of naphthalene-1-ylboronic acid to obtain Intermediate N (8.69 g, 72%).

Synthesis of C192

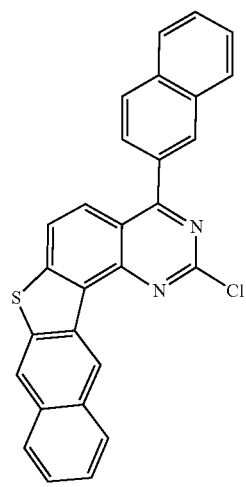

Intermediate N

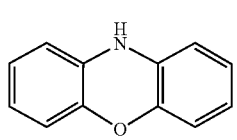

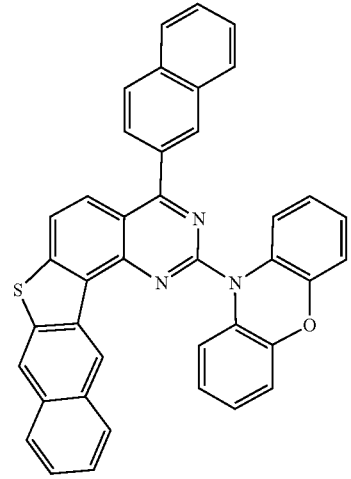

In a 100 ml three-necked flask that had been degassed and filled with nitrogen, 3 g (6.71 mmol) of Intermediate L, 1.35 g (7.38 mmol) of 10H-phenoxazine, 0.16 g (0.134 mmol) of Pd₂(dba)₃, 0.08 g (0.268 mmol) of tri-tert-butylphosphonium tetrafluoroborate, 1.3 g (13.4 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C192 (3.22 g, 81%) as an off-white solid. MS (m/z, EI⁺):593.7.

Example 12

Synthesis of C200

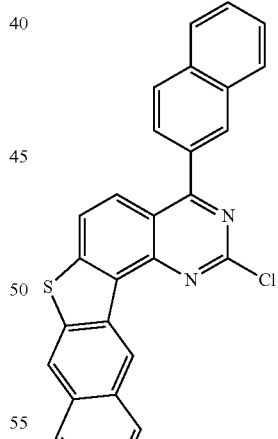

Intermediate N

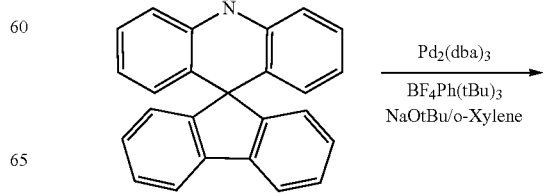

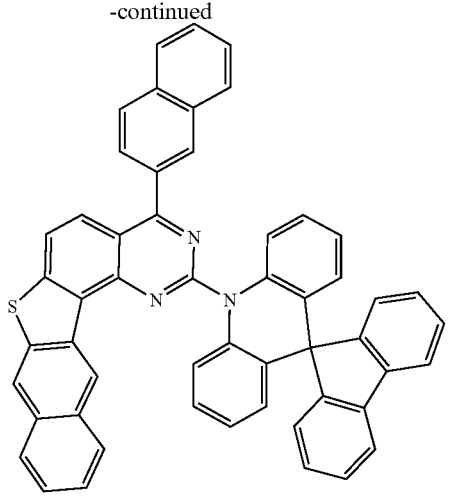

The same synthesis procedure as in Synthesis of C192 was used, except that 2.22 g of 10H-spiri[acridine-9,9'-fluorene] was used instead of 10H-phenoxazine to obtain the desired compound C200 (3.93 g, 79%). MS (m/z, EI$^+$): 741.91.

Example 13

Synthesis of C92

Synthesis of Intermediate O

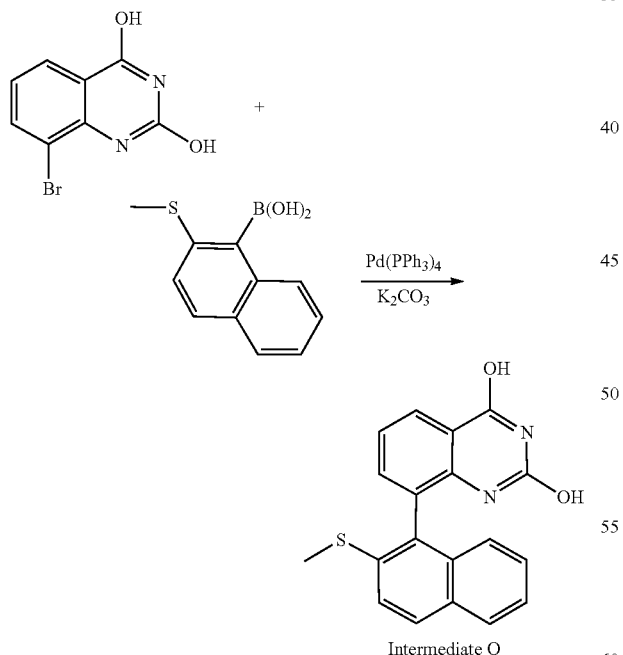

Intermediate O

Intermediate B (16 g, 66.4 mmol), (2-(methylthio)naphthalene-1-yl)boronic acid (15.9 g, 73 mmol), potassium carbonate (22.9 g, 166 mmol), Pd(PPh$_3$)$_4$ (3.8 g, 3.3 mmol) were add to THF (450 mL) and water (200 mL) in 1 L flask, and the mixture was heated at 70° C. stirred 16 hrs. After removing an aqueous layer, an organic layer remaining there was concentrated, extracted with DCM (300 mL), dried with MgSO$_4$, after removing the solvent, methanol was used for recrystallization obtain Intermediate O (16.58 g, 75%).

Synthesis of Intermediate P

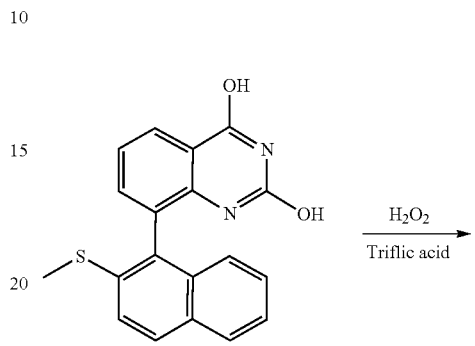

Intermediate P

Intermediate O (16.58 g, 49.58 mmol) was dissolved in glacial acetic acid (300 mL) in 1 L flask, and H$_2$O$_2$ (20%, 1 eq.) dissolved in lacial acetic acid was slowly added. The reactant was stirred at room temperature for 12 hrs, and after removing acetic acid. Subsequently, trifluorosulfonic acid was added thereto without additional purification, the obtained mixture was stirred at room temperature for 24 hrs. A KaCO$_3$ aqueous solution was added to pH-4, methanol was used for recrystallization obtain Intermediate P (11.83 g, 75%).

Synthesis of Intermediate Q

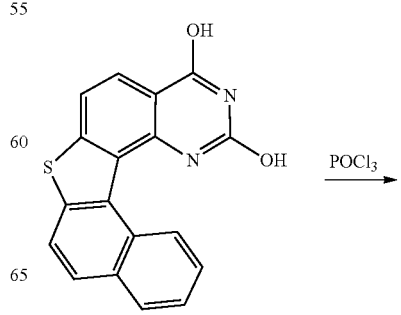

Synthesis of C92

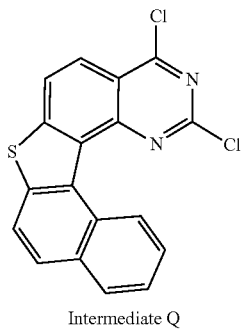

Intermediate Q

Intermediate P (11.83 g, 37.16 mmol) was added to POCl$_3$ (35 mL, 371 mmol) in a 250 mL flask, and mixture was heated at 120° C. for 4 hrs. After cooled to room temperature, and was slowly poured into ice bath. Then a solid filtered therefrom was washed water and methanol, dried to obtain Intermediate Q (12.1 g, 92%).

Synthesis of Intermediate R

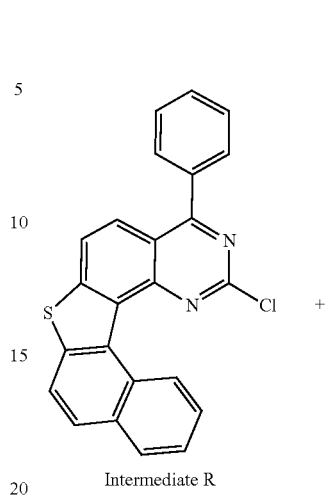

Intermediate R

Intermediate Q (12.1 g, 34.06 mmol), phenylboronic acid (4.57 g, 37.47 mmol), potassium carbonate (11.77 g, 85.15 mmol), Pd(PPh$_3$)$_4$ (1.3 g, 1.12 mmol) were add to THF (100 mL) and water (50 mL) in 250 mL flask, and the mixture was heated at 70° C. stirred 16 hrs. After removing an aqueous layer, an organic layer remaining there was concentrated, extracted with DCM (300 mL), dried with MgSO$_4$, after removing the solvent, methanol was used for recrystallization obtain Intermediate R (10.13 g, 75%).

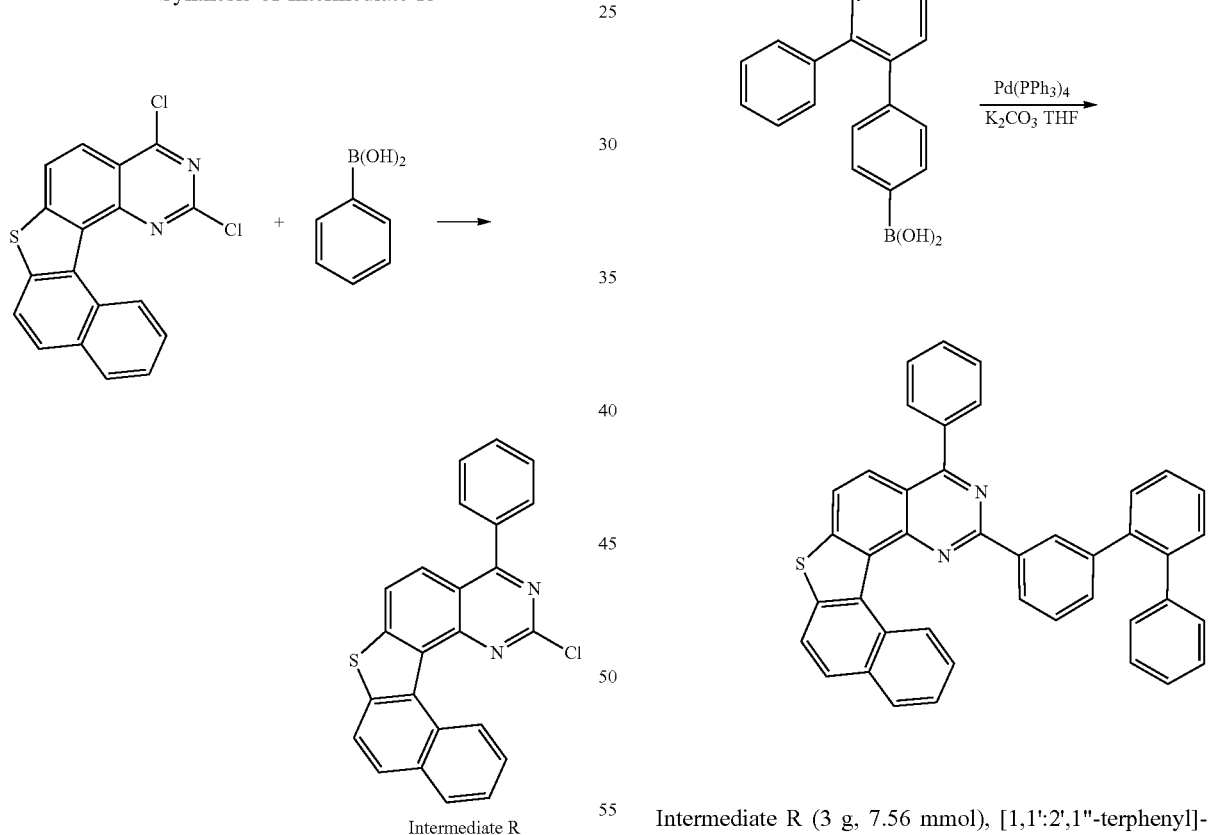

Intermediate R (3 g, 7.56 mmol), [1,1':2',1"-terphenyl]-4-ylboronic acid (2.28 g, 8.31 mmol), potassium carbonate (2.6 g, 18.9 mmol), Pd(PPh$_3$)$_4$ (0.28 g, 0.25 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C92 (3.3 g, 74%) as an off-white solid. MS (m/z, EI$^+$):590.74.

Example 14

Synthesis of C94

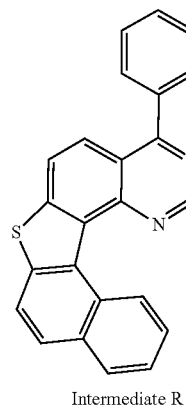

Intermediate R

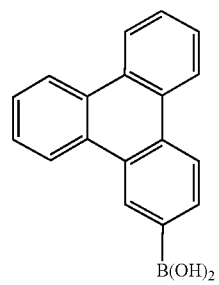

$\xrightarrow{\text{Pd(PPh}_3)_4}{\text{K}_2\text{CO}_3 \text{ THF}}$

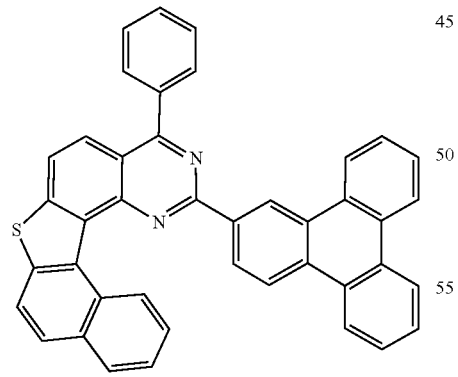

The same synthesis procedure as in Synthesis of C92 was used, except that 2.26 g of triphenylen-2-ylboronic acid was used instead of [1,1': 2',1'-terphenyl]-4-ylboronic acid to obtain the desired compound C94 (3.6 g, 81%). MS (m/z, EI⁺):588.73.

Example 15

Synthesis of C202

Synthesis of Intermediate S

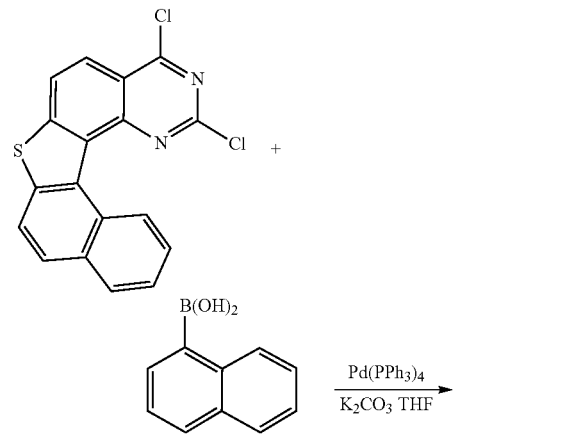

Intermediate S

The same synthesis procedure as in Synthesis of Intermediate R was used, except that 5.86 g of naphthalene-1-ylboronic acid was used instead of phenylboronic acid to obtain Intermediate S (10.8 g, 71%).

Synthesis of C202

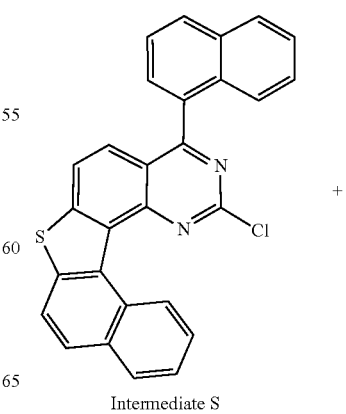

Intermediate S

-continued

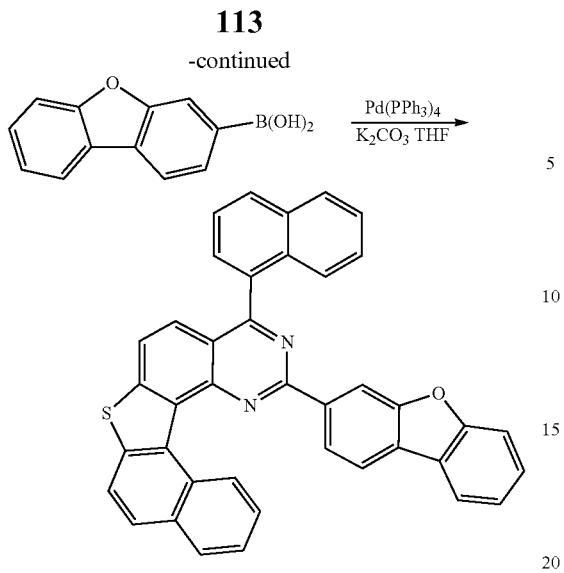

Intermediate S (3 g, 6.71 mmol), dibenzofuran-3-ylboronic acid (2.12 g, 7.38 mmol), potassium carbonate (2.32 g, 16.7 mmol), Pd(PPh₃)₄ (0.26 g, 0.22 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C202 (3.25 g, 74%) as an off-white solid. MS (m/z, EI⁺):654.79.

Example 16

Synthesis of C218

The same synthesis procedure as in Synthesis of C202 was used, except that 2.44 g of (4-(9-phenyl-9H-carbazol-2-yl)phenyl)boronic acid was used instead of dibenzofuran-3-ylboronic acid to obtain the desired compound C218 (3.6 g, 81%). MS (m/z, EI⁺):729.9.

Example 17

Synthesis of C216

Synthesis of Intermediate T

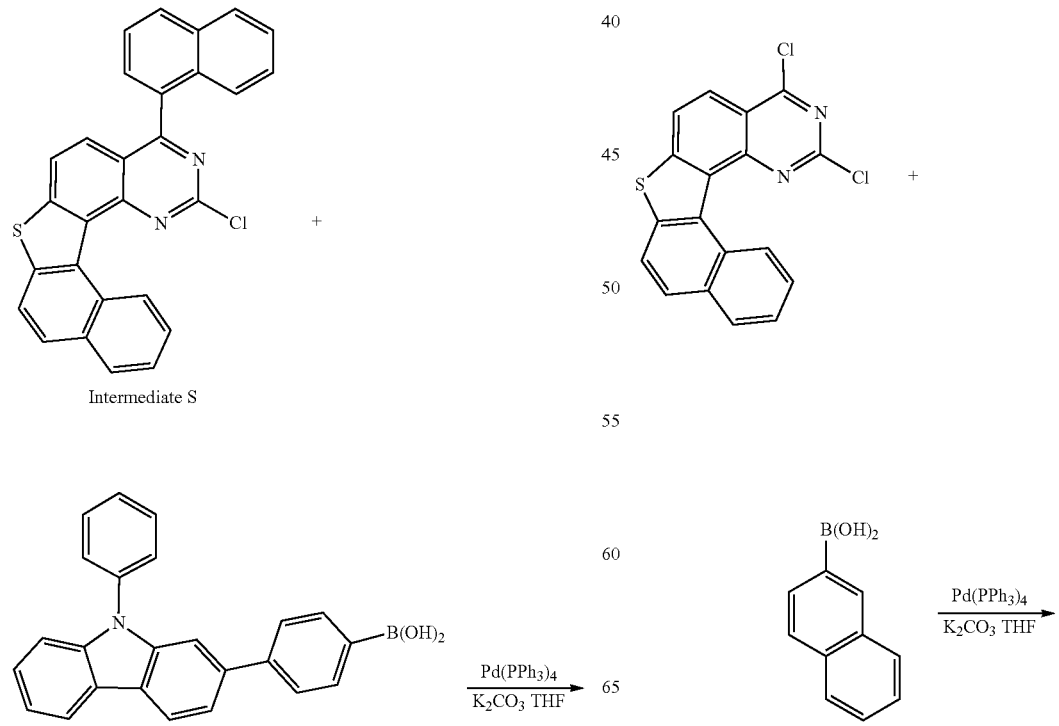

115
-continued

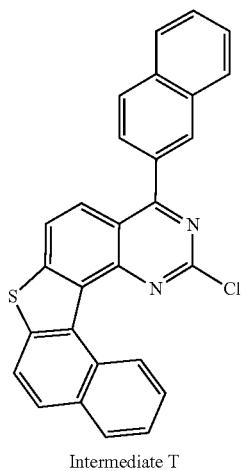

Intermediate T

The same synthesis procedure as in Synthesis of Intermediate R was used, except that 5.86 g of naphthalene-2-ylboronic acid was used instead of phenylboronic acid to obtain Intermediate T (11.4 g, 71%).

Synthesis of C216

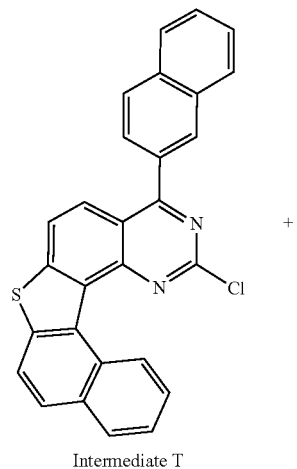

Intermediate T

116
-continued

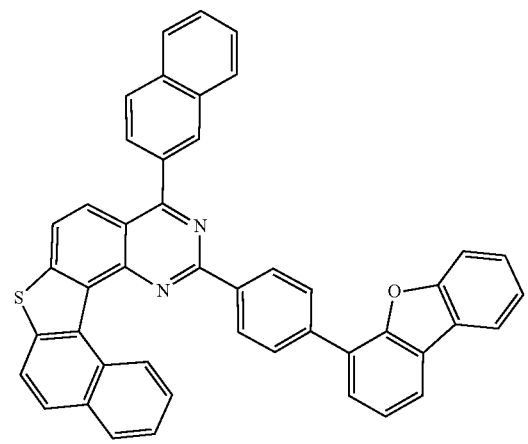

Intermediate T (3 g, 6.71 mmol), dibenzofuran-3-ylboronic acid (2.12 g, 7.38 mmol), potassium carbonate (2.32 g, 16.7 mmol), Pd(PPh₃)₄ (0.26 g, 0.22 mmol) were add to THF (30 mL) and water (15 mL) in 250 mL flask, and the mixture was heated at 70° C. stirred 16 hrs. After cooling to room temperature, the mixture was filtered to give a solid. The solid was washed with water and MeOH, and then filtered to give compound C216 (3.25 g, 74%) as an off-white solid. MS (m/z, EI⁺):654.79.

Example 18

Synthesis of C220

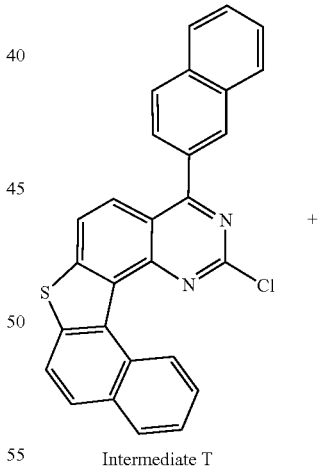

Intermediate T

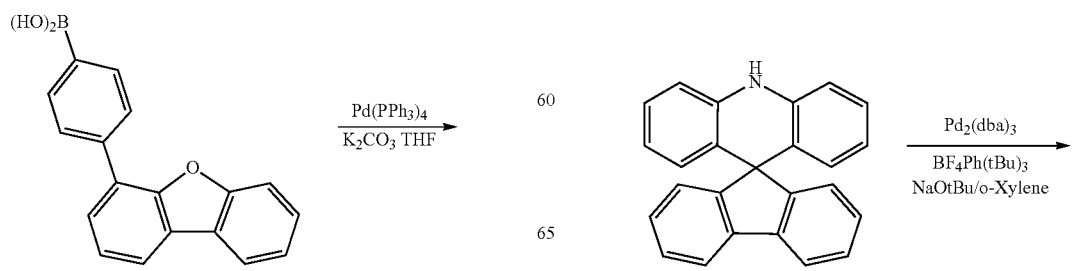

-continued

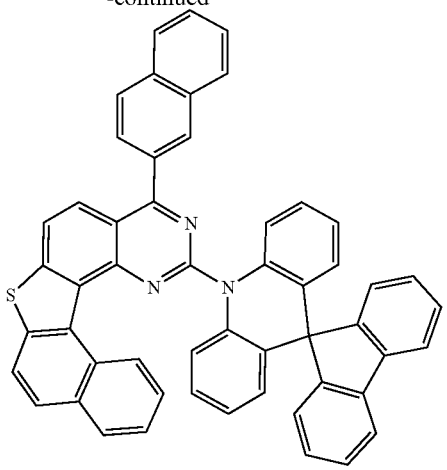

In a 100 ml three-necked flask that had been degassed and filled with nitrogen, 3 g (6.71 mmol) of Intermediate T, 2.44 g (7.38 mmol) of 10H-spiri[acridine-9,9'-fluorene], 0.16 g (0.134 mmol) of Pd$_2$(dba)$_3$, 0.08 g (0.268 mmol) of tri-tert-butylphosphonium tetrafluoroborate, 1.3 g (13.4 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C220 (3.98 g, 80%) as an off-white solid. MS (m/z, EI$^+$):741.91.

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

The organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, e.g. a host material doped with a dopant material in the light emitting layer. This is successfully achieved by co-vaporization from two or more sources, which means the iridium complex of the present invention is thermally stable.

Dipyrazino[2,3-f:2,3-]quinoxaline-2,3,6,7,10,11-hexacarbonitrile (HAT-CN) is used to form the hole injection layer, and N,N-bis(naphthalene-1-yl)-N,N-bis(phenyl)-benzidine (NPB) is used to form the hole transporting layer of the organic EL device. N-(biphenyl-4-yl)-9,9-dimethyl-N-(4'-phenyl-biphenyl-4-yl)-9H-fluoren-2-amine (EB2) is used to form the electron blocking layer. HB3 is used as hole blocking material (HBM), and 2-(10,10-dimethyl-10H-indeno [2,1-b]triphenylen-12-yl)-4,6-diphenyl-1,3,5-triazine (ET2) is used as electron transporting material to co-deposit with 8-hydroxyquinolato-lithium (LiQ) in organic EL devices. For fluorescence emitting device, 4,4'-Bis(carbazol-9-yl)biphenyl (CBP) is used as the host material, and Ir(piq)2acac is used as the phosphorescent dopant. Compounds C1, C2, C126, C130, C56, C60, C178, C182, C192, C200, C92, C94, C202, C218, C216, and C200 are used as the fluorescent host materials to compare with CBP. The chemical structures of conventional OLED materials and the exemplary organic compounds of the present invention for producing control and exemplary organic EL devices in this invention are shown as follows:

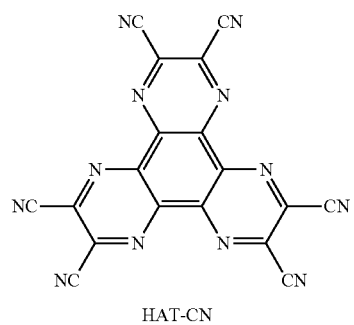

HAT-CN

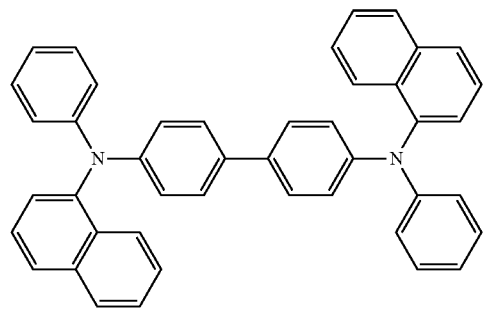

NPB

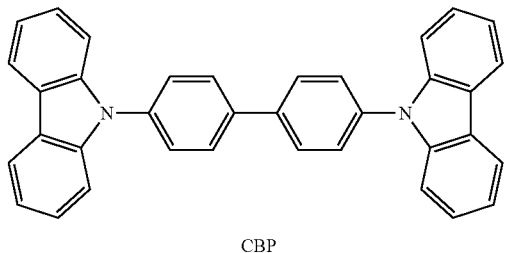

CBP

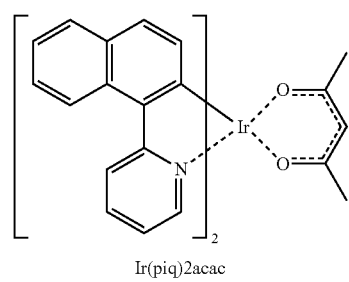

Ir(piq)2acac

HB3
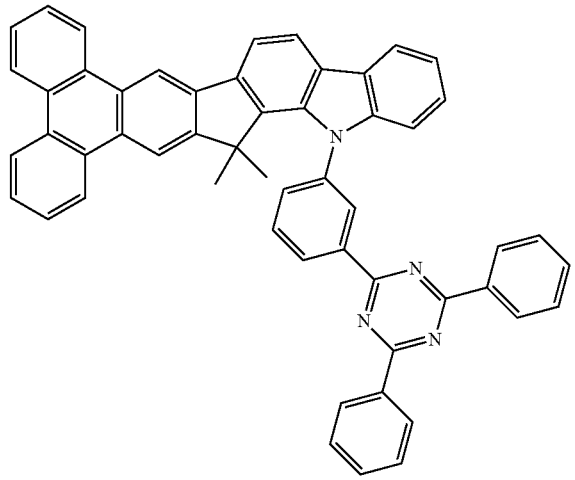
C2
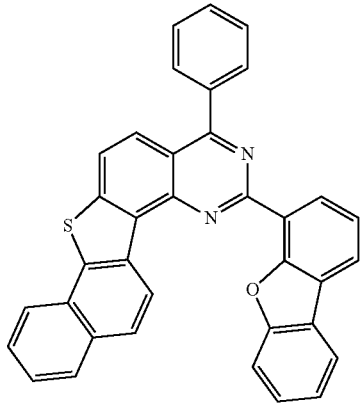
EB2
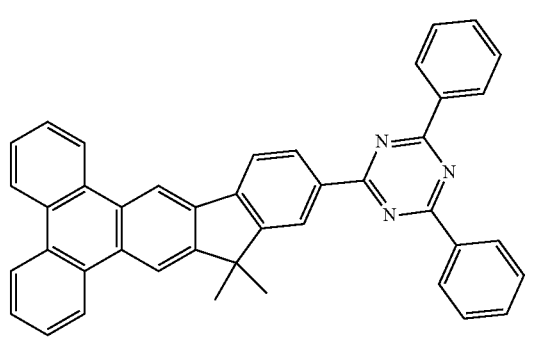
C126
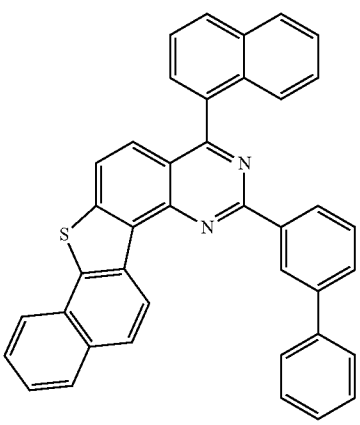
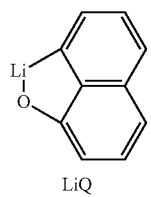
LiQ
C1
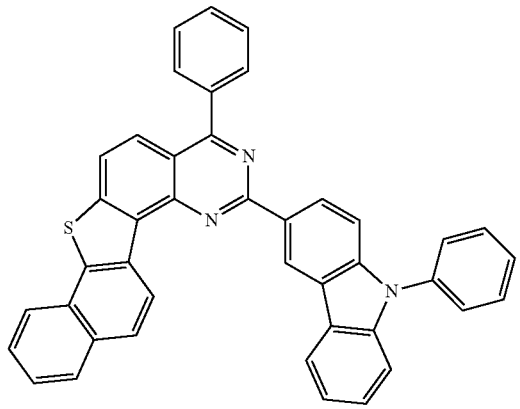
C130
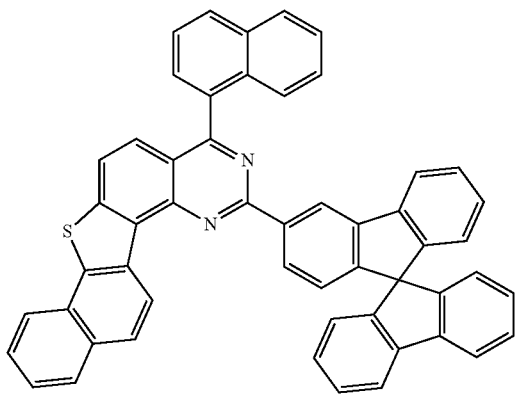

-continued
C128
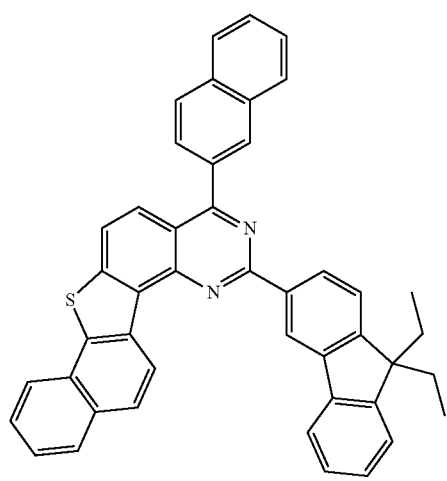
C60
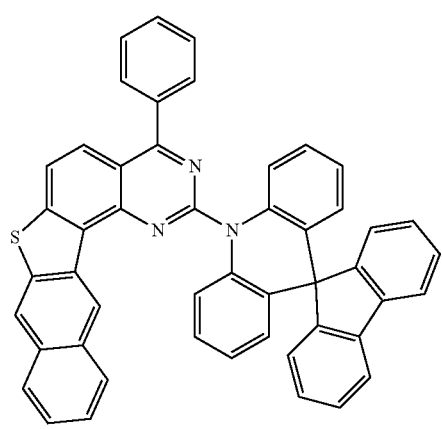
C132
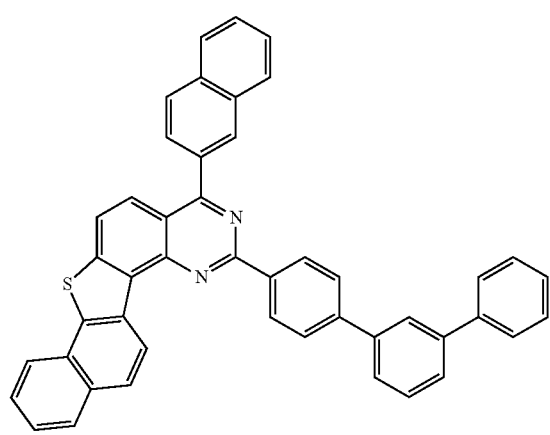
C178
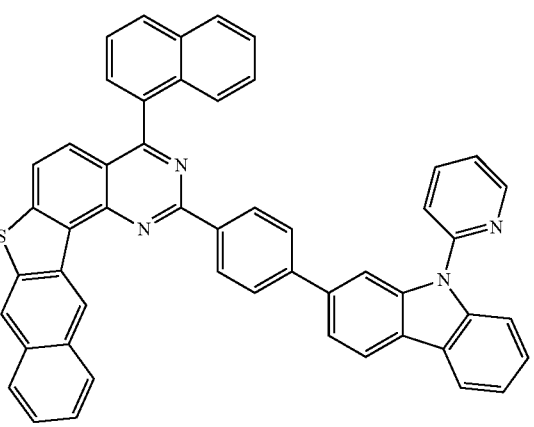
C56
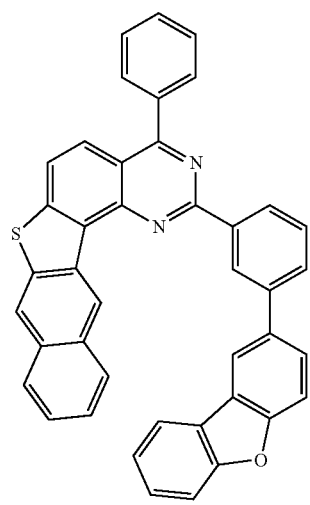
C182
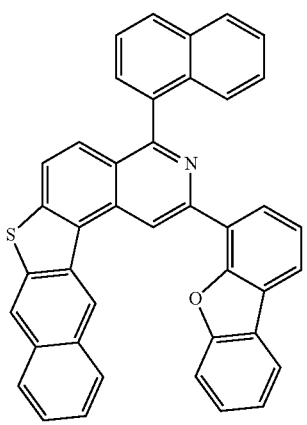

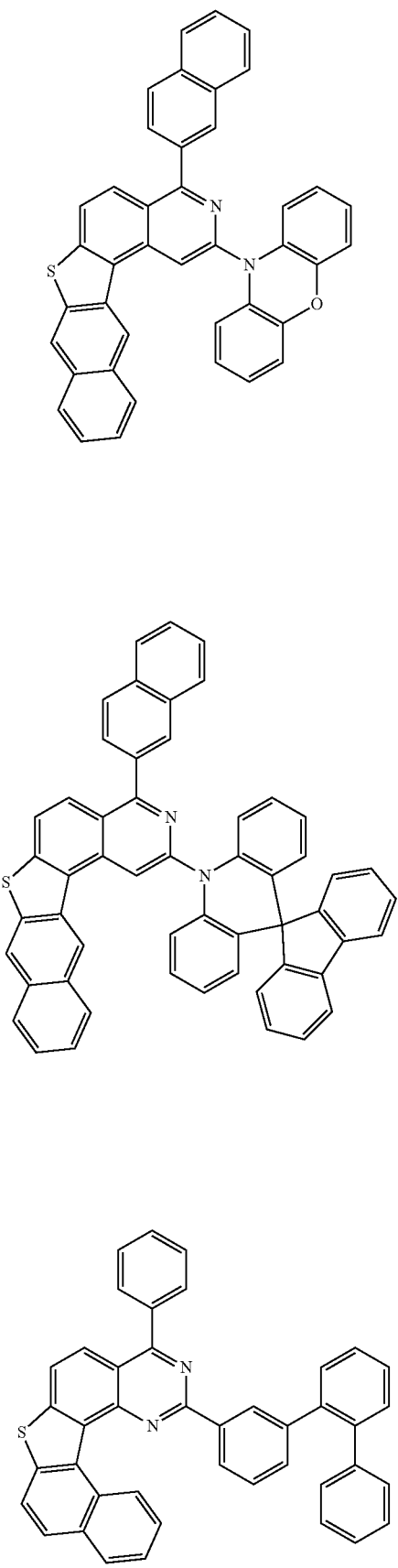

-continued

C220

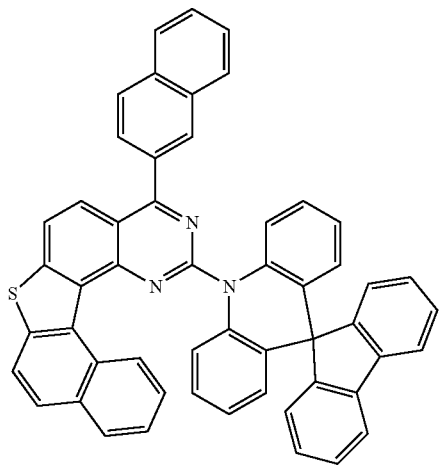

A typical organic EL device consists of low work function metals, such as Al, Mg, Ca, Li and K, as the cathode, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 19

Using a procedure analogous to the above mentioned general method, organic EL devices emitting phosphorescence and having the following device structure as shown in the FIGURE. From the bottom layer 10 to the top lay 80, the following components were produced: ITO/HAT-CN (20 nm)/NPB (110 nm)/EB2 (5 nm)/CBP doped with 15% phosphorescent dopant (30 nm)/HB3 (10 nm)/ET2 doped with 40% LiQ (35 nm)/LiQ (nm)/Al (160 nm). In the device illustrated in the FIGURE, the hole injection layer 20 (HAT-CN) is deposited onto the transparent electrode 10 (ITO), the hole transport layer 30 (NPB) is deposited onto the hole injection layer 20, the emitting layer 40 is deposited onto the hole transport layer 30. The emitting layer 40 may comprise an emitting host material and an emitting guest (dopant) material, as shown in, for example, Table 1. The emitting host material may be doped with about 15% emitting guest material. The emitting layer 40 may have a thickness of about 30 nm. The hole blocking layer 50 (HB3) is deposited onto the emitting layer 40. The electron transport layer 60 (ET2 doped with 50% LiQ) is deposited onto the hole blocking layer 50. The electron transport layer 70 (LiQ) is deposited onto the electron transport layer 60. The metal electrode 80 (Al) is deposited onto the electron injection layer 70. The I-V-B (at 1000 nits) and 90% life time test reports of these organic EL devices are summarized in Table 1 below. The 90% life time is defined as the time the initial luminance of 5000 $cd/m^2$ has dropped to 10% of the initial luminance.

TABLE 1

| Host | Dopant Material | Driving Voltage (V) | Current Efficiency (cd/A) | Color (EL color) | 90% life time (hrs) at 5000 $cd/m^2$ |
|---|---|---|---|---|---|
| CBP | — | 6 | 5.8 | red | 20 |
| CBP | C1 | 4.3 | 16.8 | red | 90 |
| CBP | C2 | 4.4 | 17.1 | red | 110 |
| CBP | C126 | 4.6 | 17.5 | red | 130 |
| CBP | C130 | 4.6 | 17.4 | red | 125 |
| CBP | C128 | 4.5 | 17.2 | red | 125 |
| CBP | C132 | 4.4 | 16.9 | red | 120 |
| CBP | C56 | 4.5 | 17.2 | red | 135 |
| CBP | C60 | 4.6 | 17.6 | red | 150 |
| CBP | C178 | 4.3 | 16.7 | red | 110 |
| CBP | C182 | 4.3 | 16.6 | red | 100 |
| CBP | C192 | 4.2 | 16.4 | red | 95 |
| CBP | C200 | 4.5 | 17.3 | red | 140 |
| CBP | C92 | 4.4 | 17.1 | red | 125 |
| CBP | C94 | 4.6 | 17.8 | red | 145 |
| CBP | C202 | 4.5 | 17.4 | red | 130 |
| CBP | C218 | 4.6 | 17.9 | red | 140 |
| CBP | C216 | 4.5 | 17.8 | red | 150 |
| CBP | C220 | 4.4 | 17.6 | red | 120 |

In the above test report of organic EL devices (see Table 1), the organic material with formula (A) used as a host material for organic EL devices in the present invention displays better performance than the prior art organic EL materials. More specifically, the organic EL devices of the present invention use an organic material with formula (A) as emitting quest material to collocate with emitting host material, such as CBP, showing lower power consumption, higher efficiency, or longer 90% life time.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic compound represented by the following formula (A):

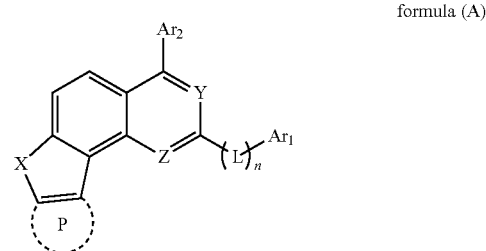

formula (A)

wherein X is a divalent bridge selected from the group consisting of O and S; Y and Z are independently C(Rs) or N, Rs is a hydrogen atom or an alkyl group; P represents a substituted or unsubstituted naphthyl group; at least one of Y and Z is N; L represents a single bonded, a substituted or unsubstituted arylene group having 6 to 30 ring carbon atoms or a substituted or unsubstituted heteroaryl group having 5 to 30 ring atoms; n represents an integer of 0 to 1; Ar$_1$ is selected from the group consisting of a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; Ar$_2$ represents a phenyl group or a naphthyl group.

2. The organic compound according to claim 1, wherein the organic compound is represented by one of the following formula (B) to formula (J):

formula (B)

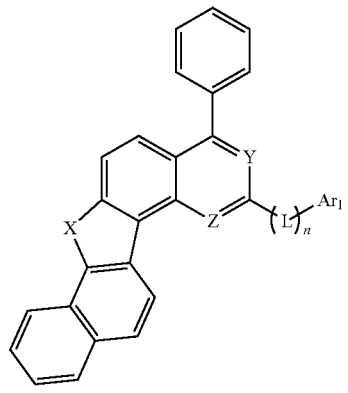

formula (C)

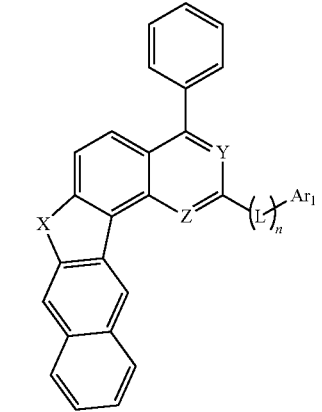

formula (D)

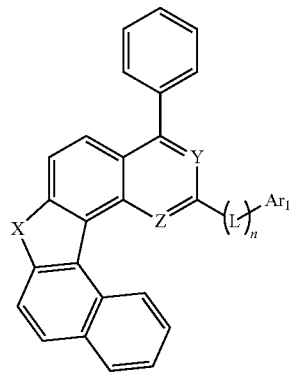

formula (E)

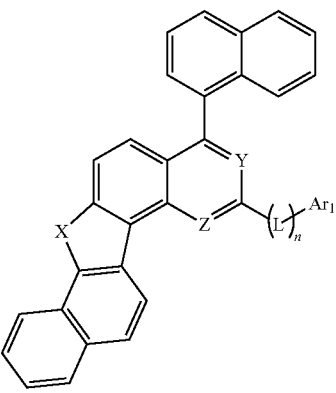

formula (F)

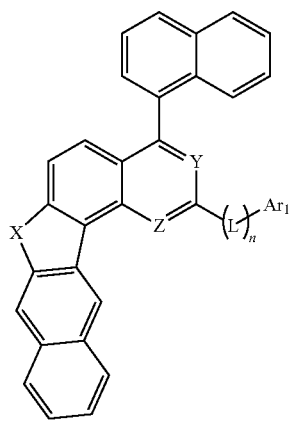

formula (G)

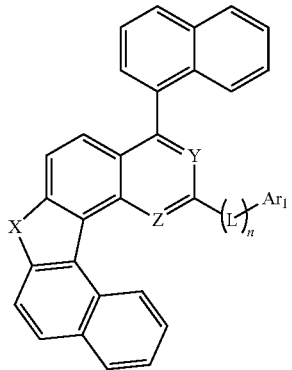

formula (H)

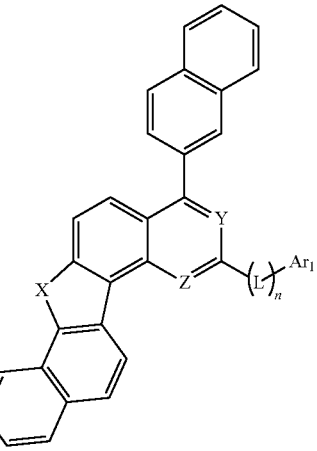

formula (I)

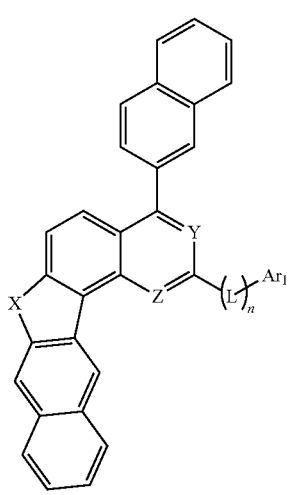

and formula (J)

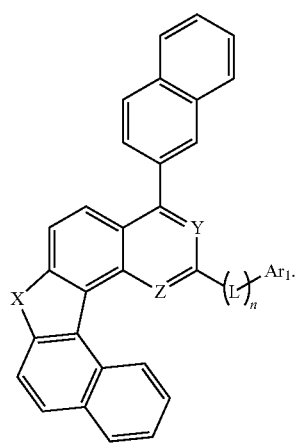

3. The organic compound according to claim 1, wherein Ar₁ is a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, or a substituted or unsubstituted pyridinyl group.

4. The organic compound according to claim 1, wherein Ar₁ represents one of the following substituents:

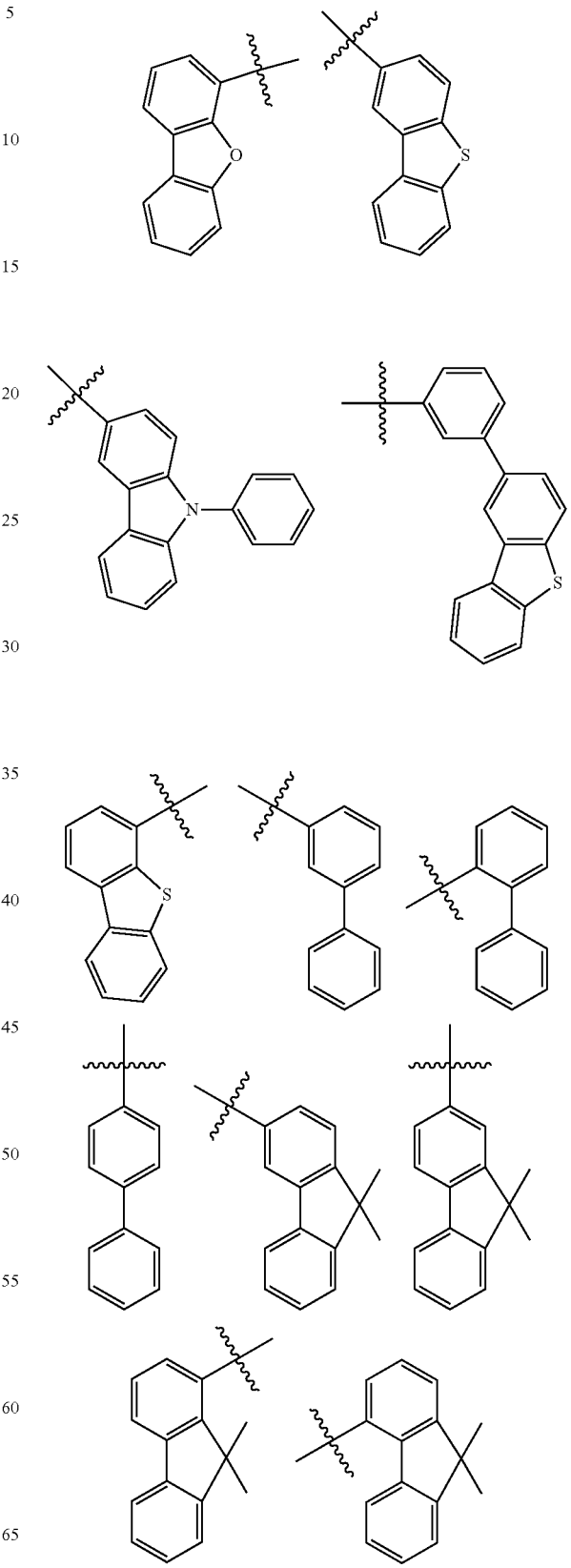

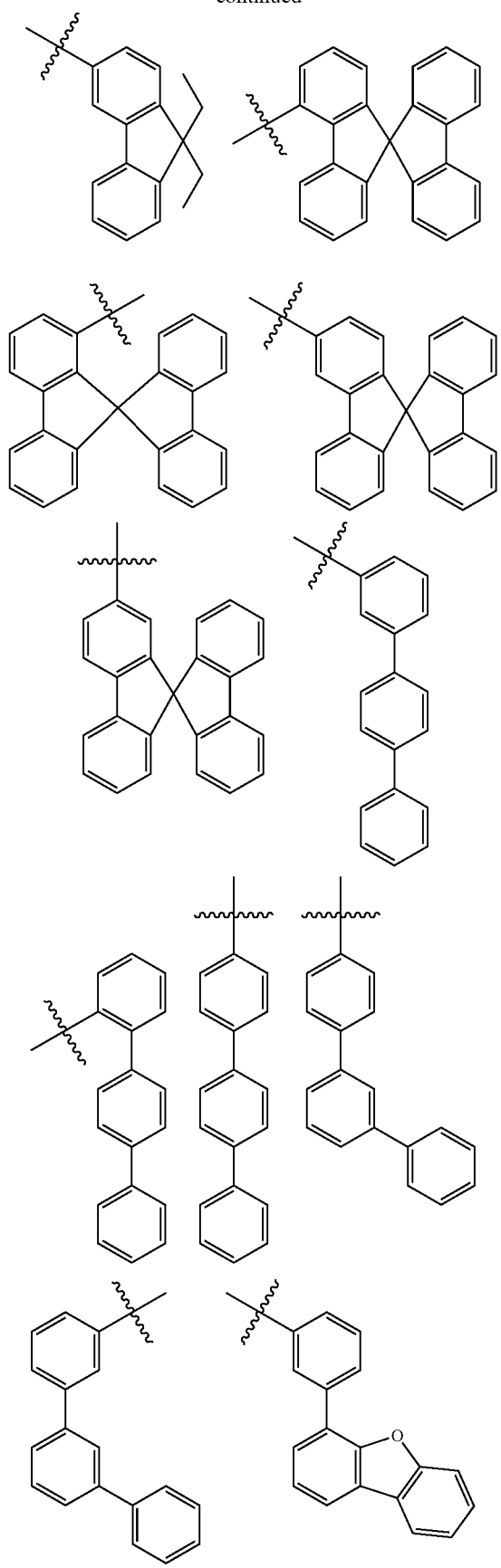
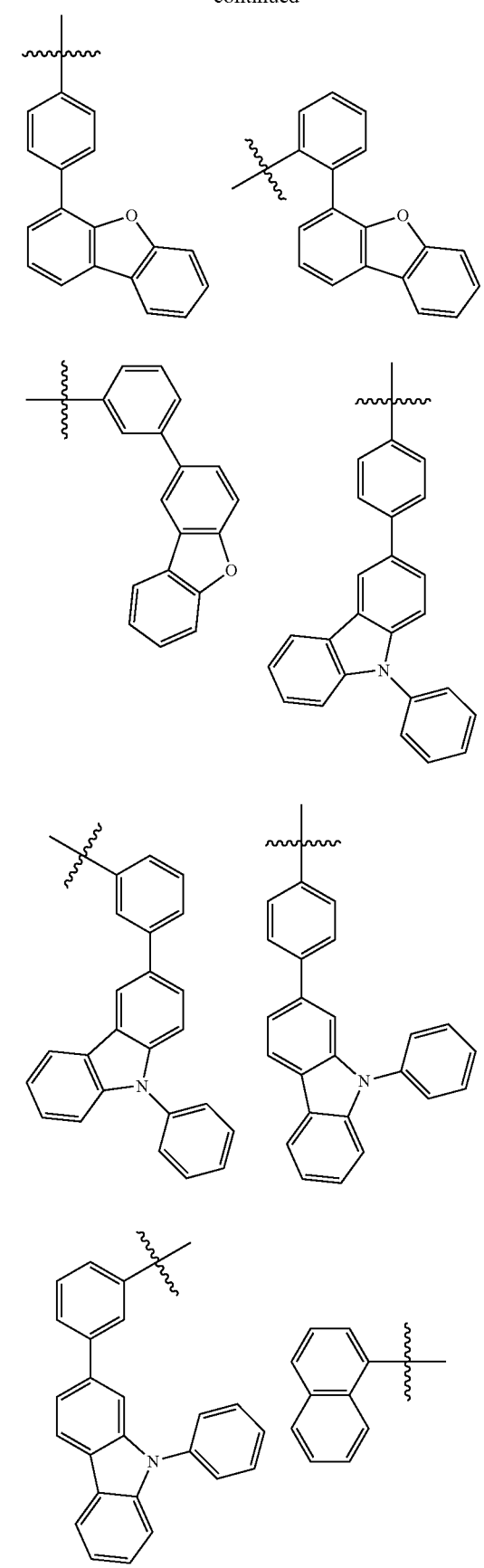

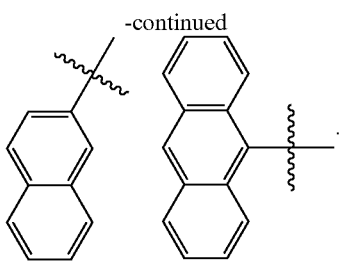
5. The organic compound according to claim 1, wherein the organic compound is one of the following compounds:
C1
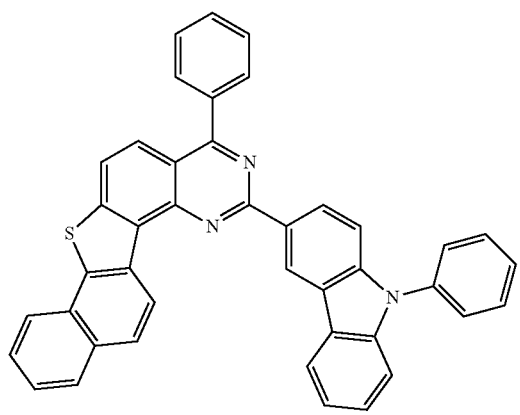
C2
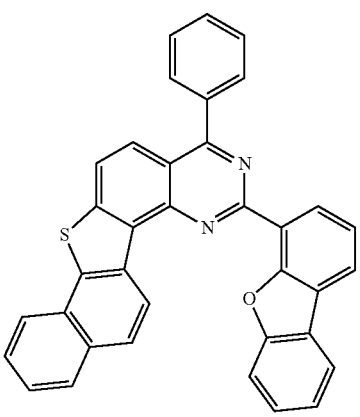
C3
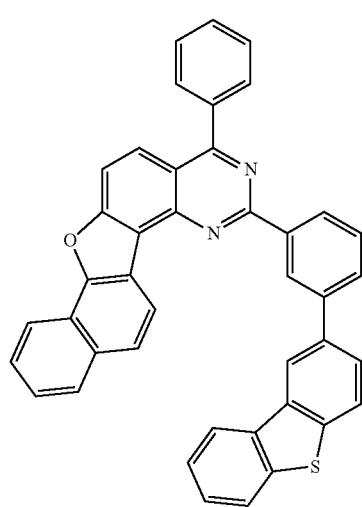
C4
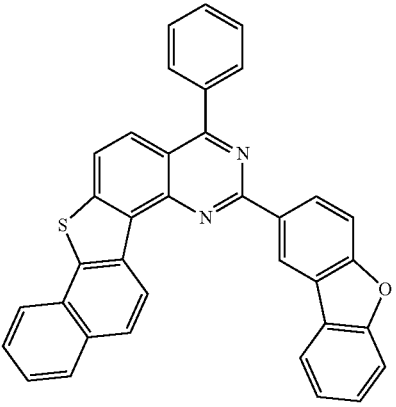
C5
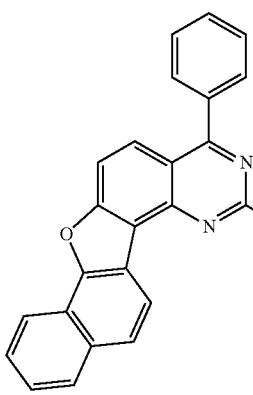
C6
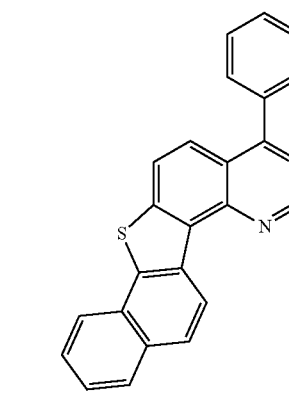
C7
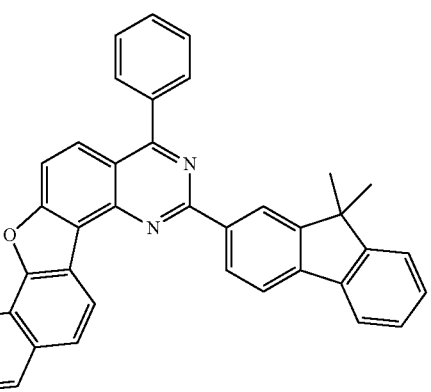

C8
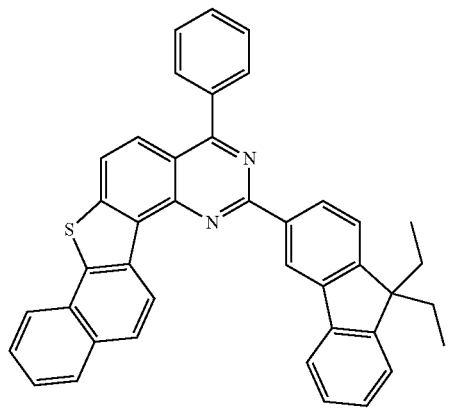
C11
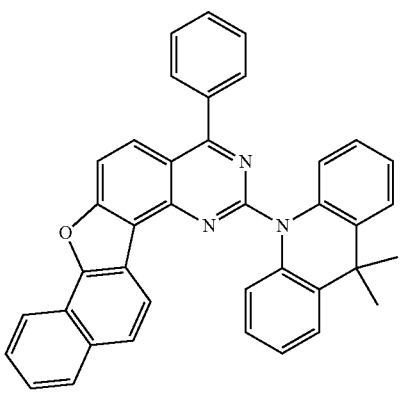
C9
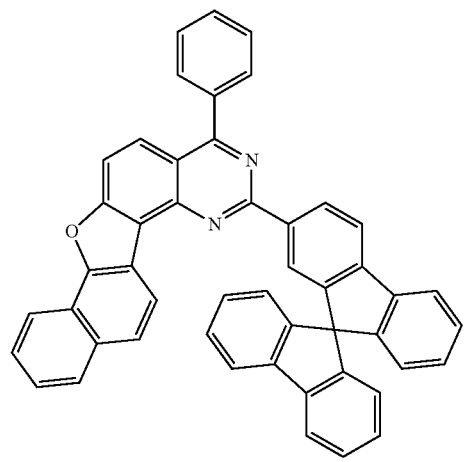
C12
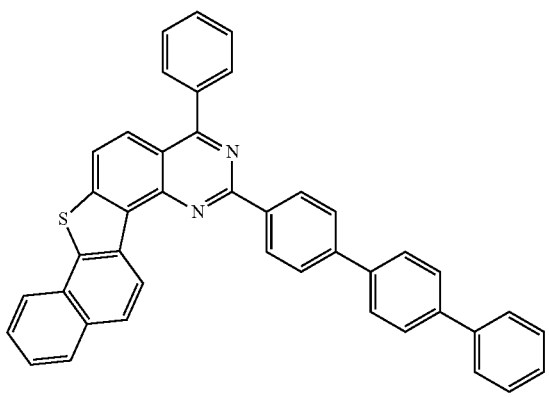
C10
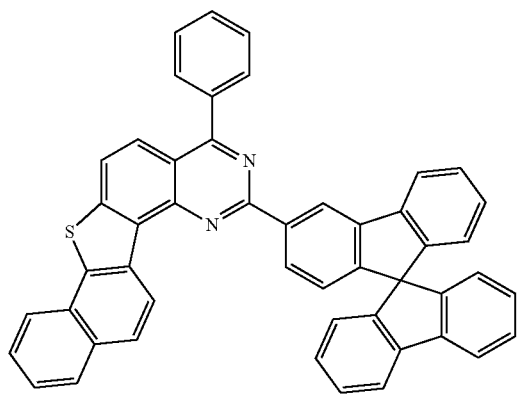
C13
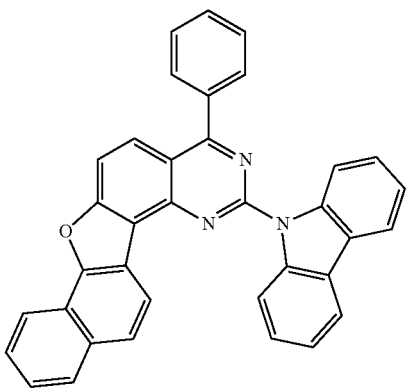

C14
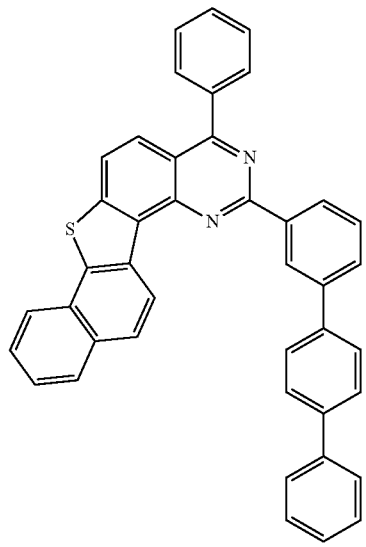
C15
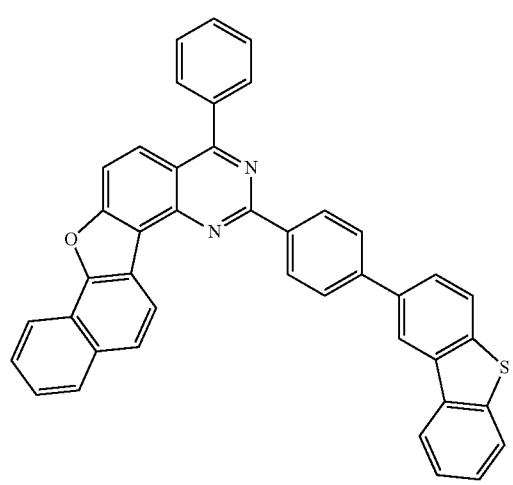
C16
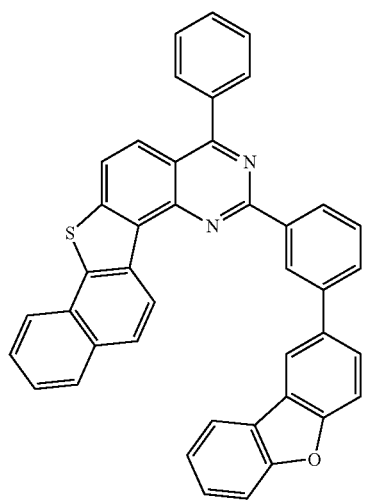
C17
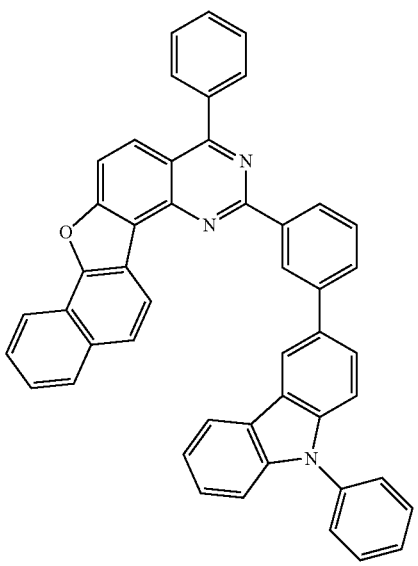
C18
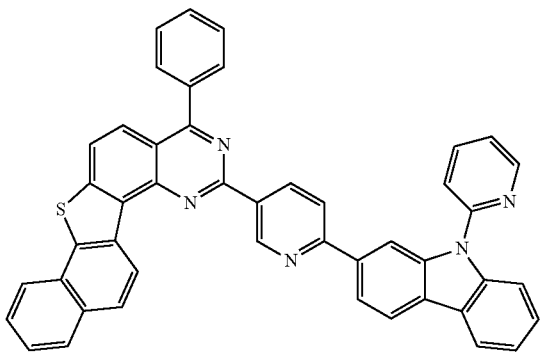
C19
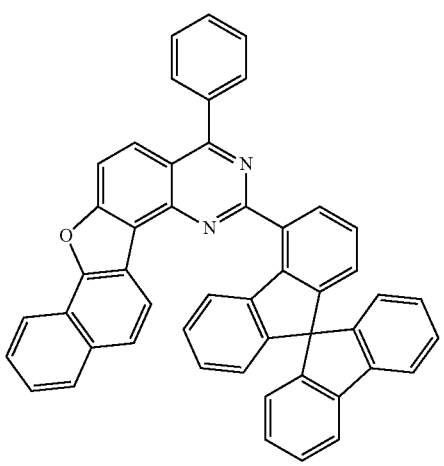

-continued
C20
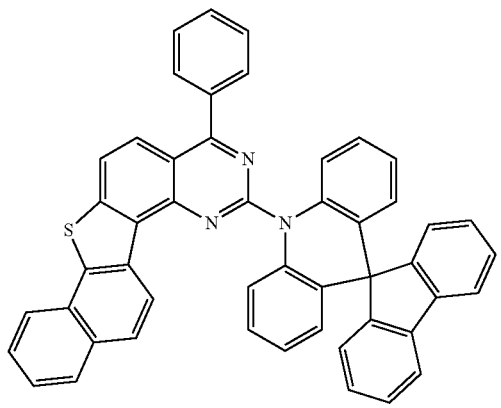
C21
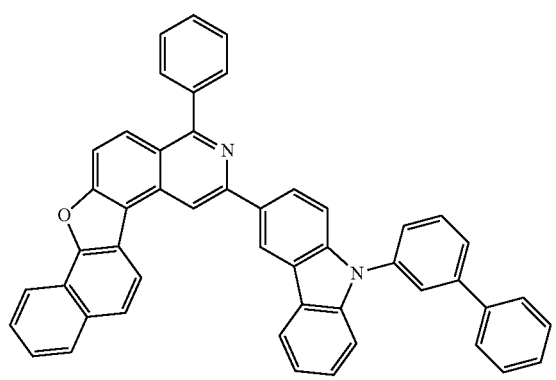
C22
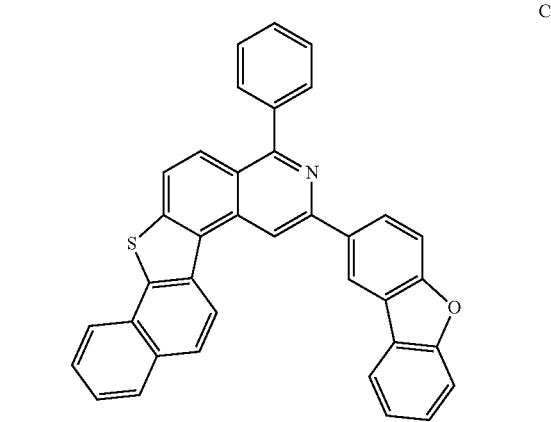
-continued
C23
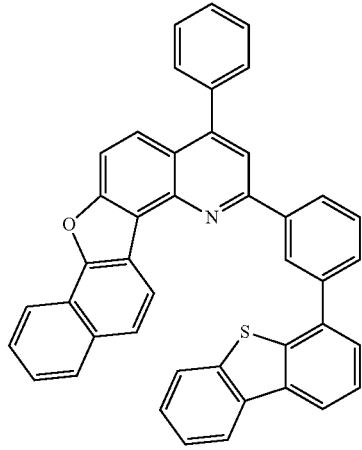
C24
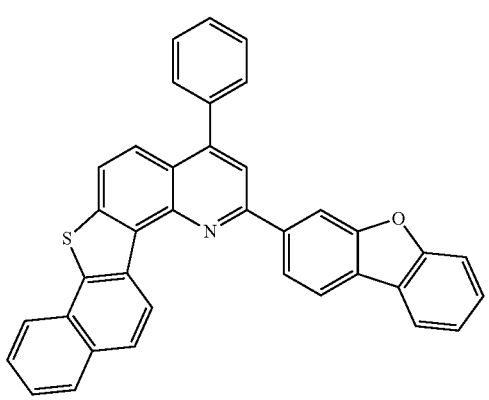
C25
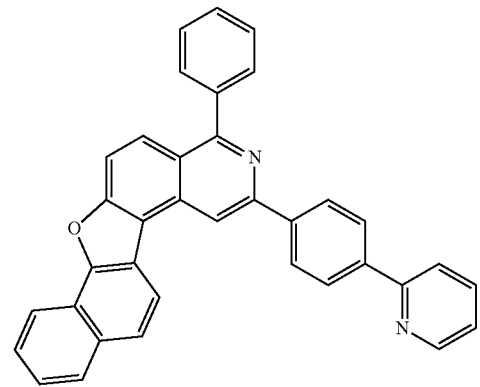
C26
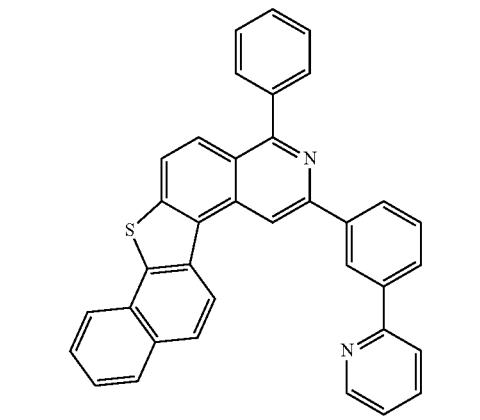

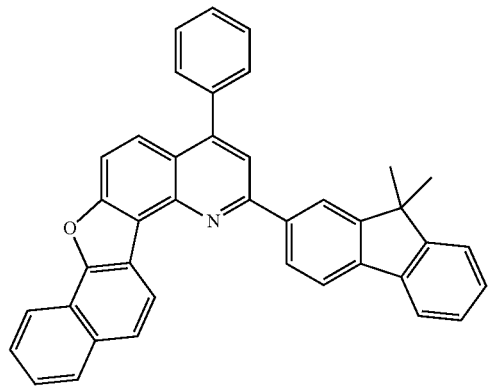 C27
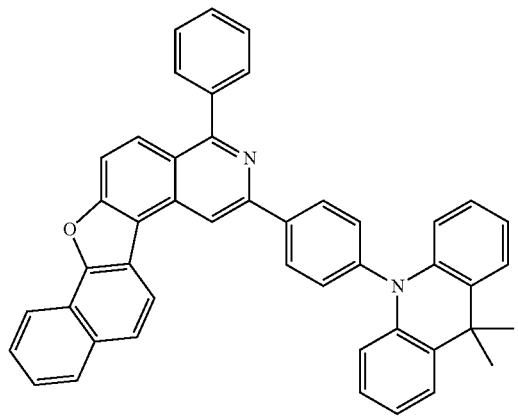 C31
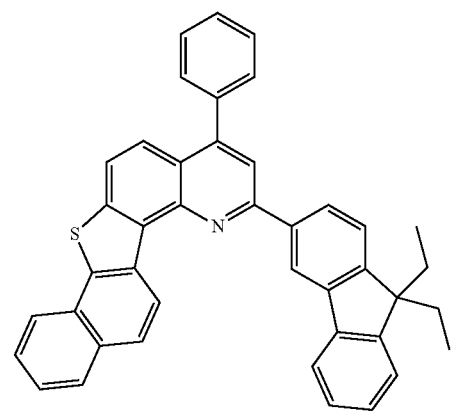 C28
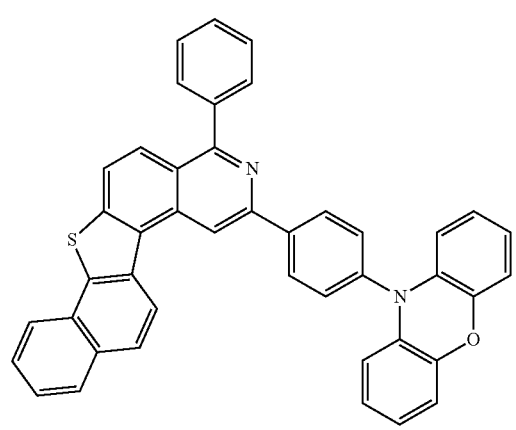 C32
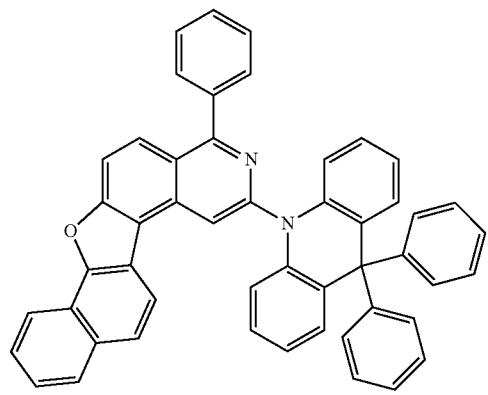 C29
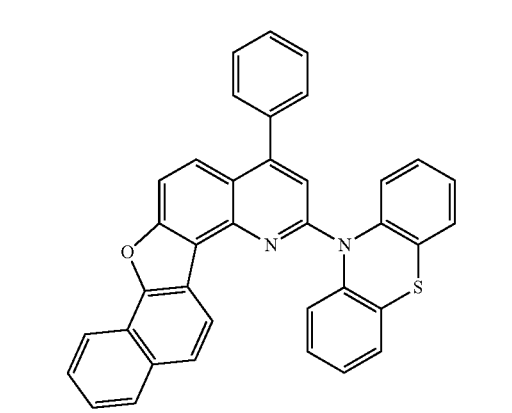 C33
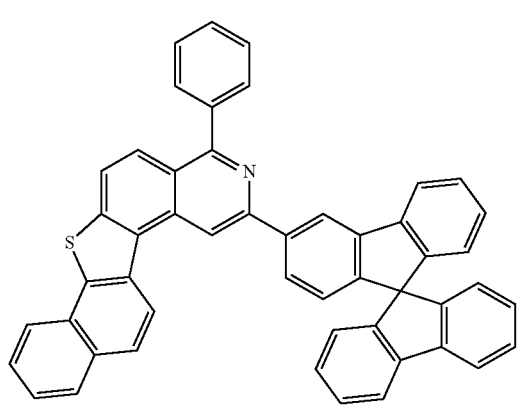 C30
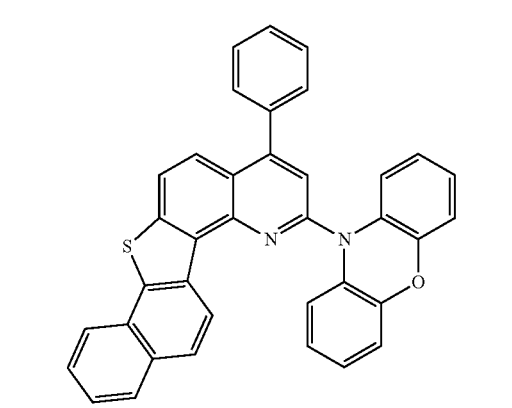 C34

C35
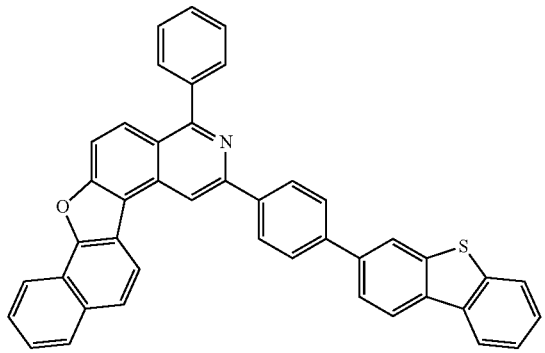
C36
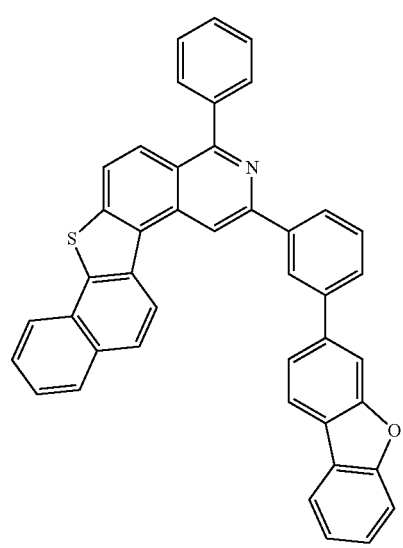
C37
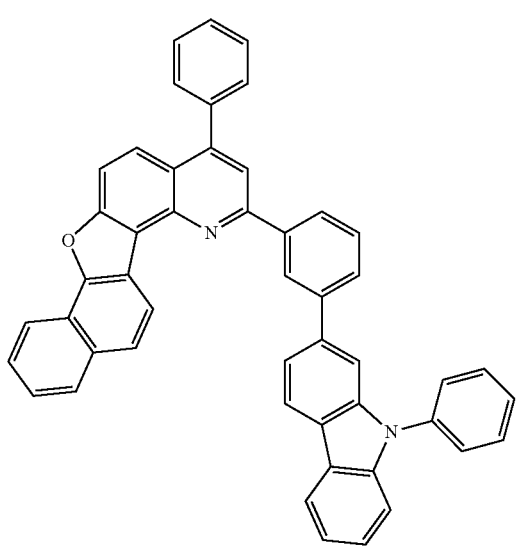
C38
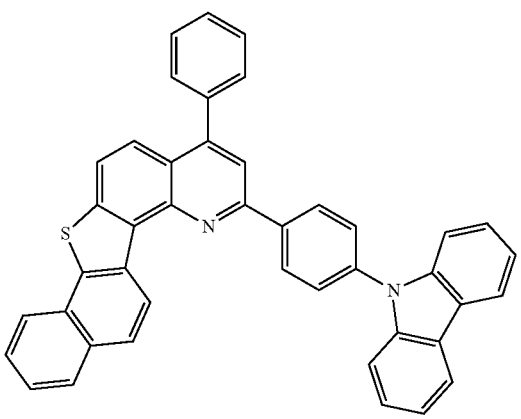
C39
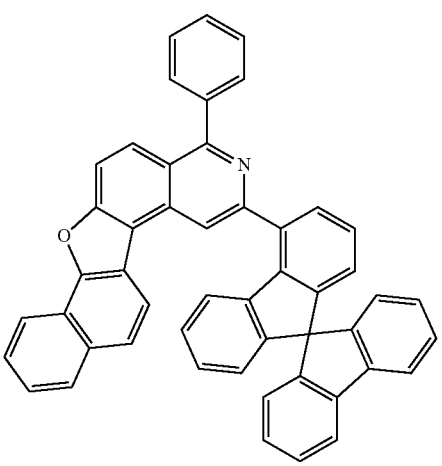
C40
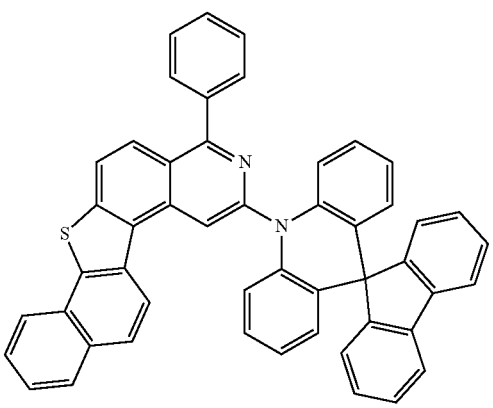

145
-continued
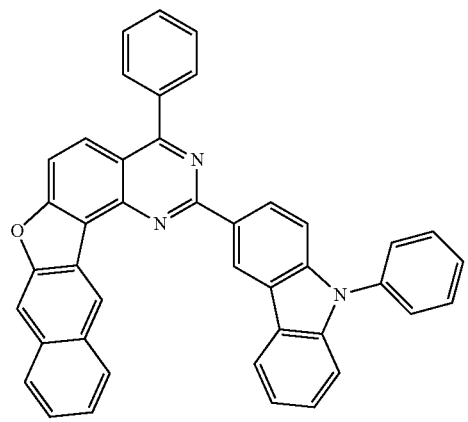
C41
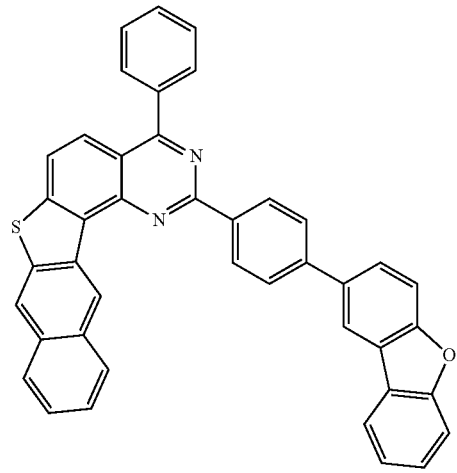
C42
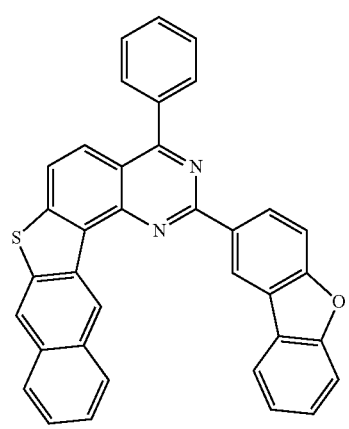
146
-continued
C44
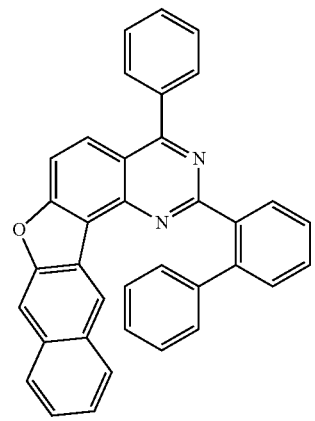
C45
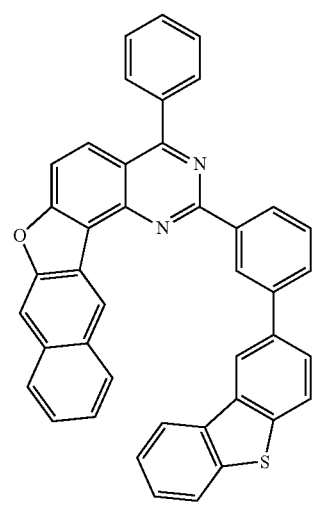
C43
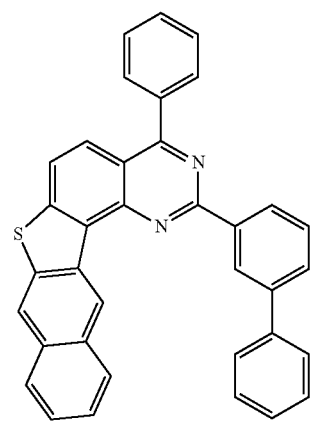
C46

C47
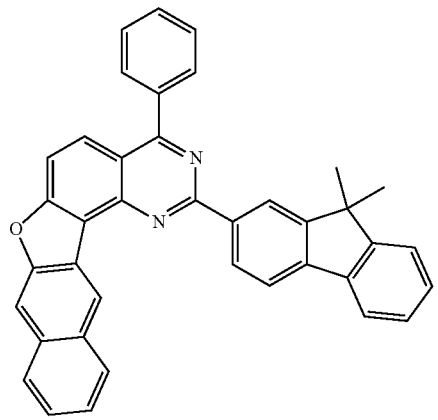
C50
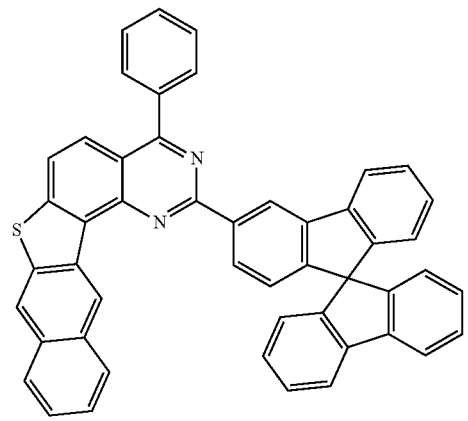
C48
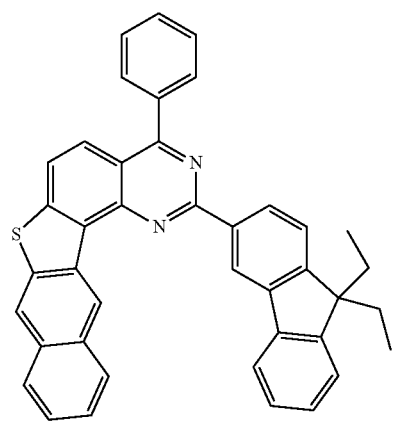
C51
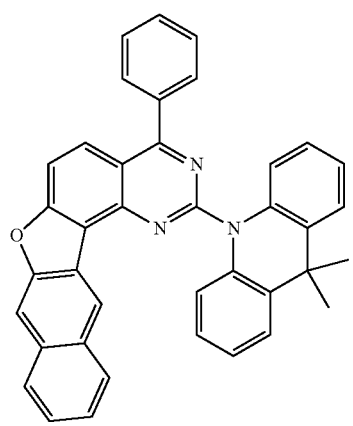
C49
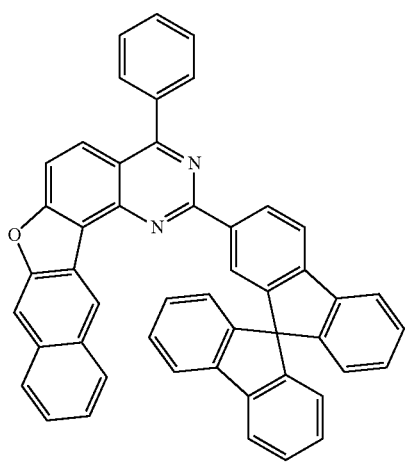
C52
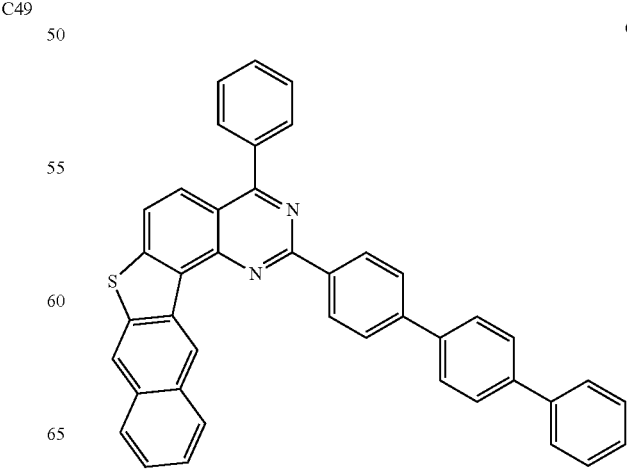

-continued
C53
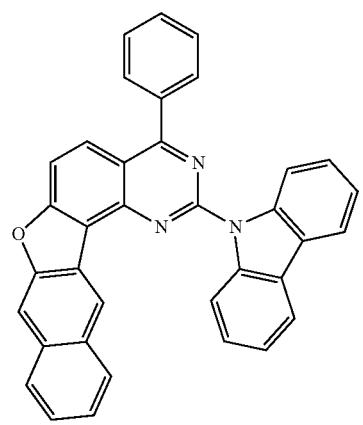
C54
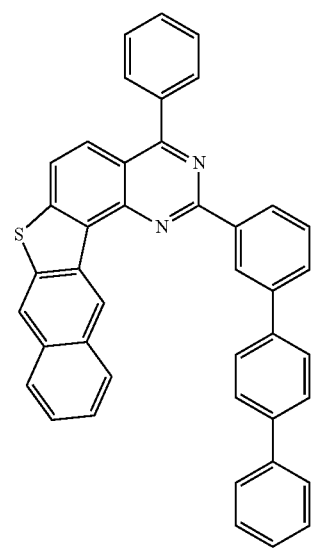
C55
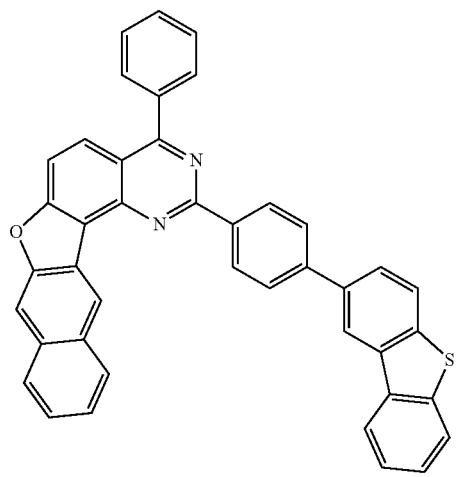
-continued
C56
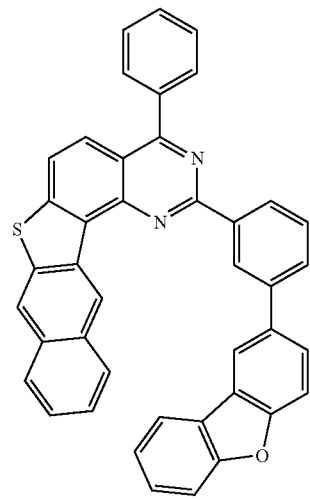
C57
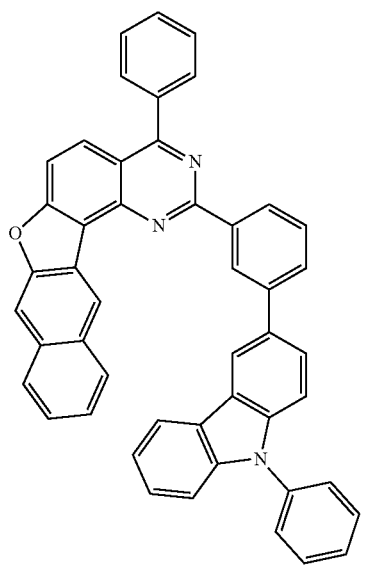
C58
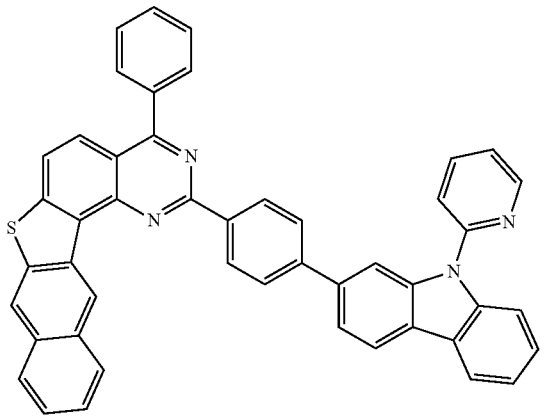

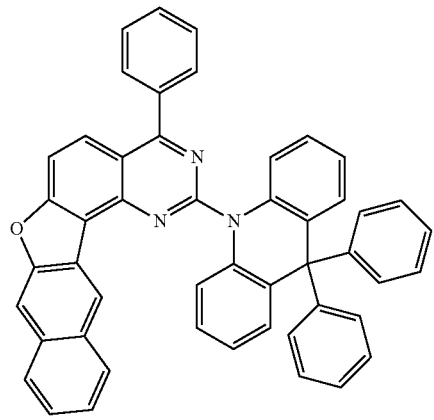
C59
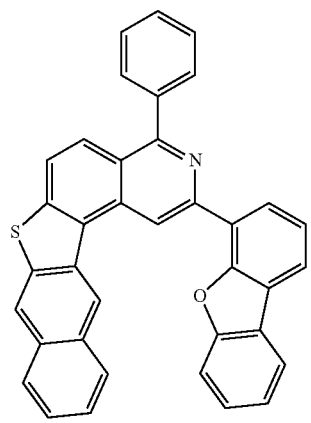
C62
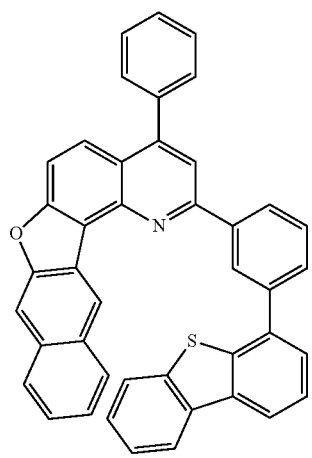
C63
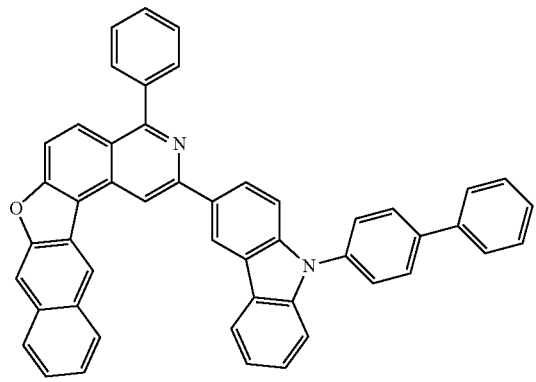
C60
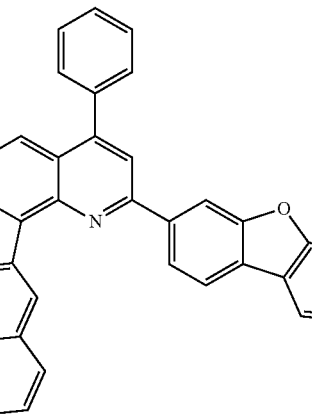
C64
C61

C65
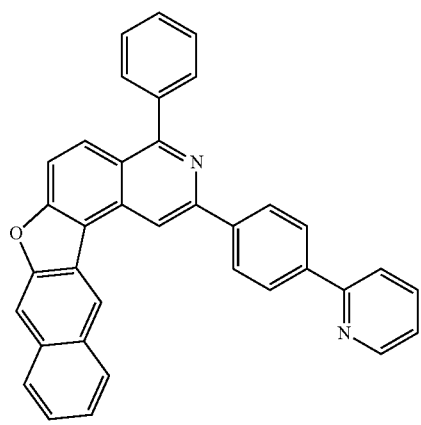
C66
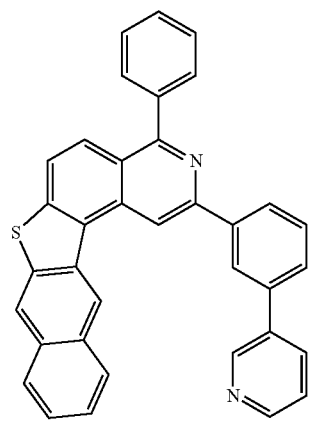
C67
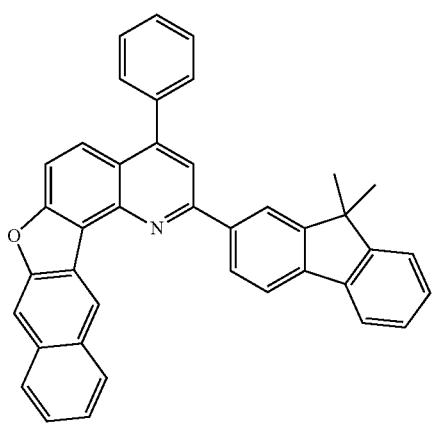
C68
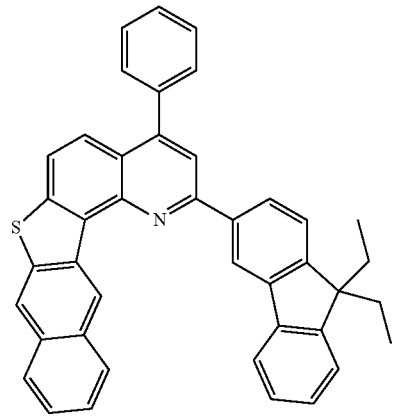
C69
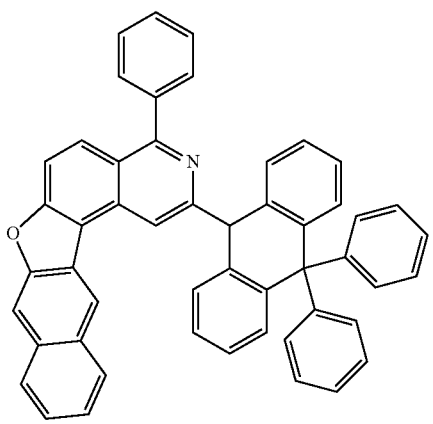
C70
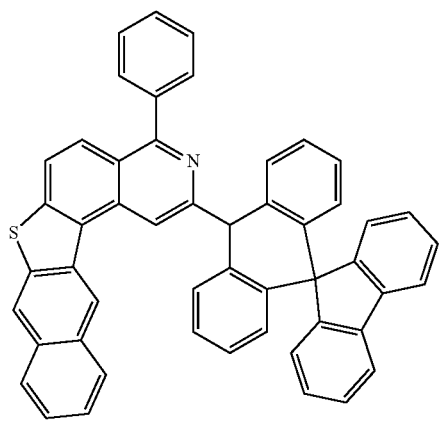

-continued
C71
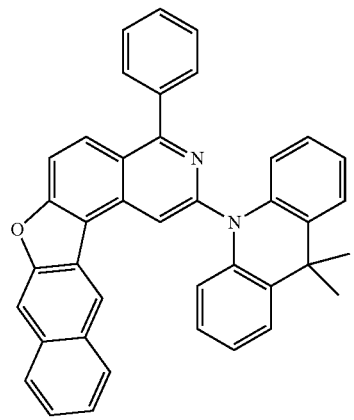
C72
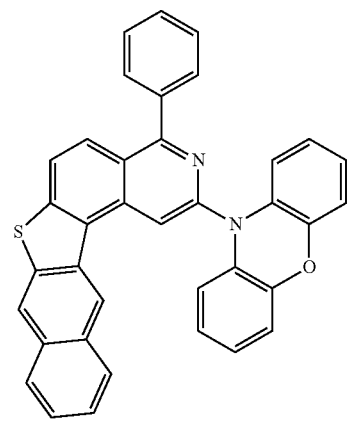
C73
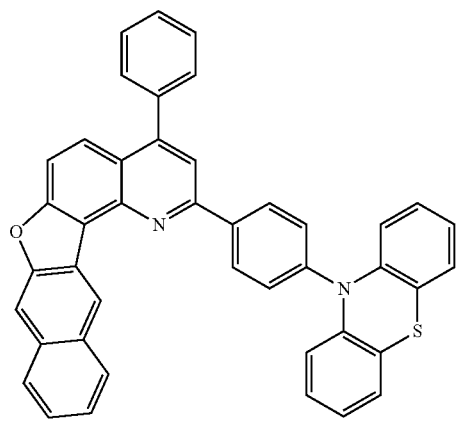
-continued
C74
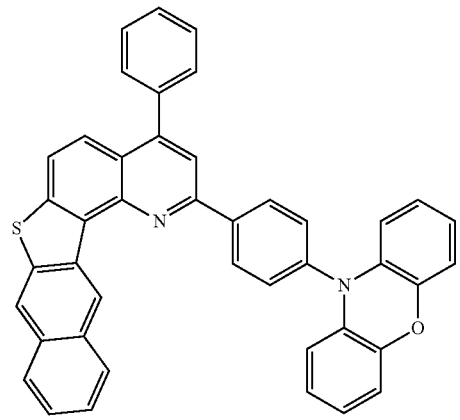
C75
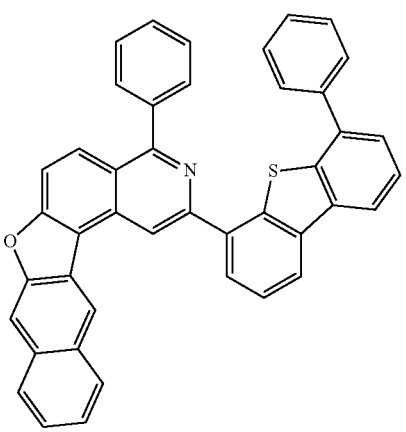
C76
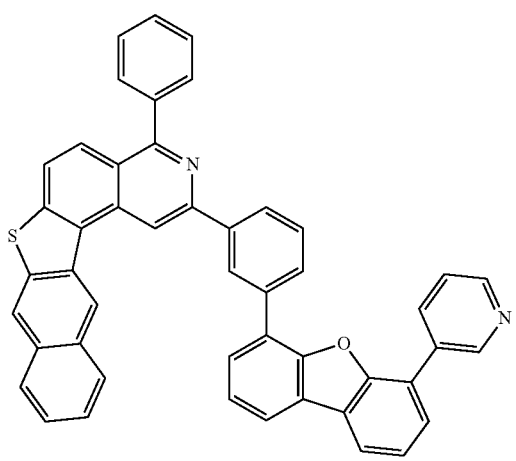

-continued
C77
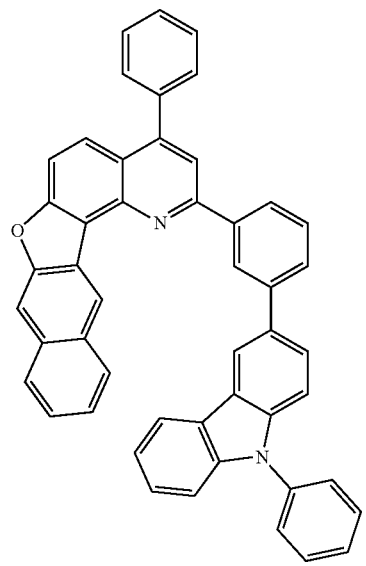
C78
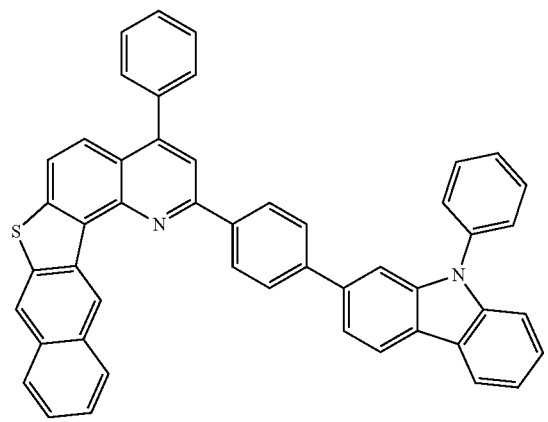
C79
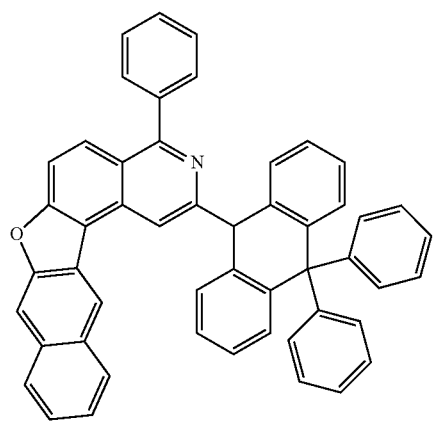
-continued
C80
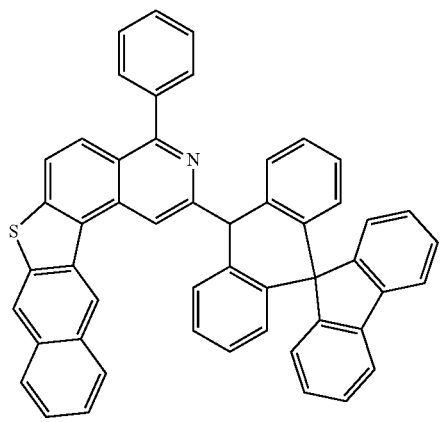
C81
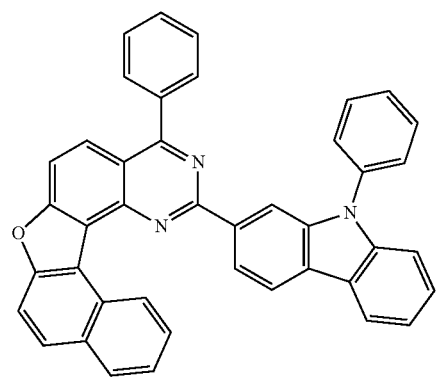
C82
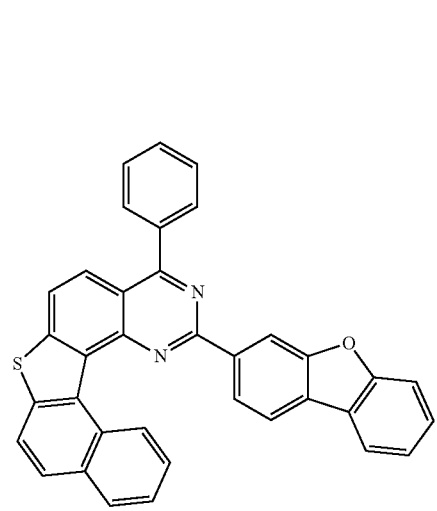

-continued
C83
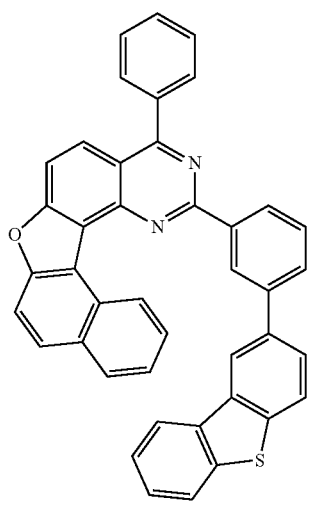
C84
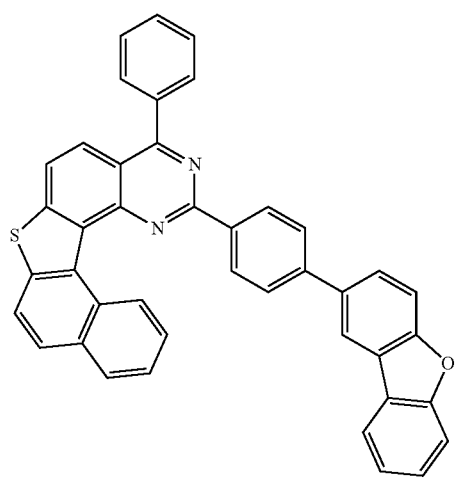
C85
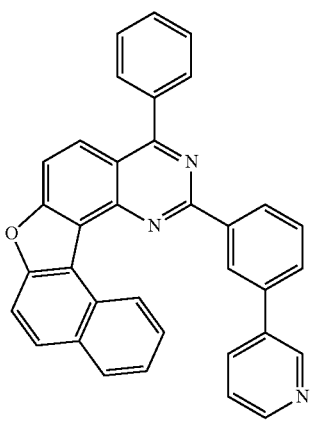
-continued
C86
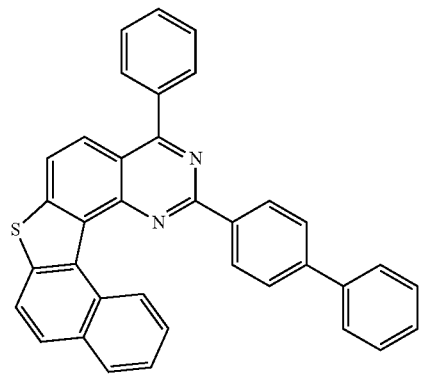
C87
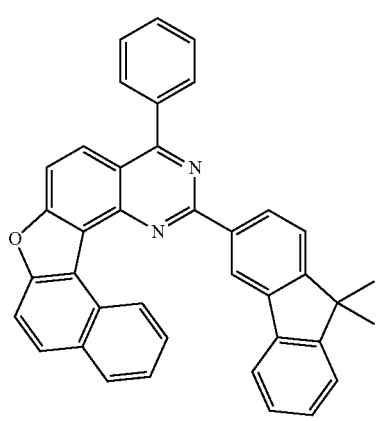
C88
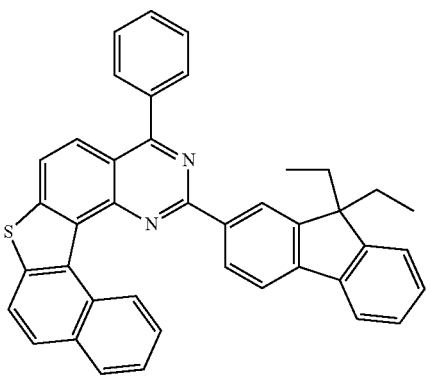
C89

C90
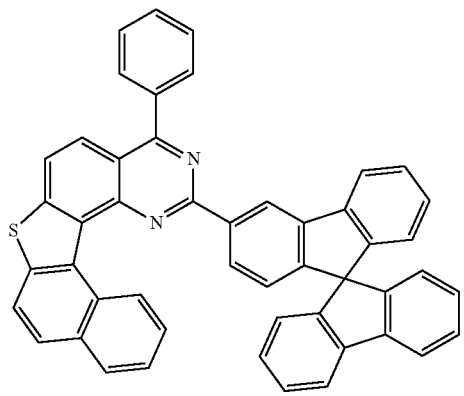
C91
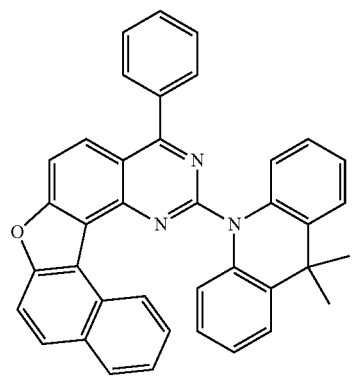
C92
C93
C94
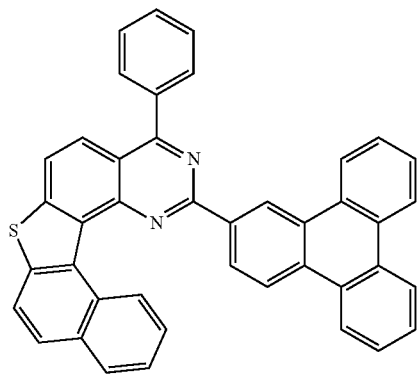
C95
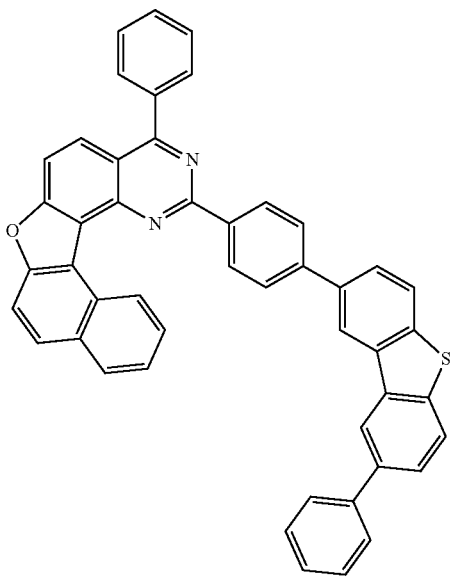
C96
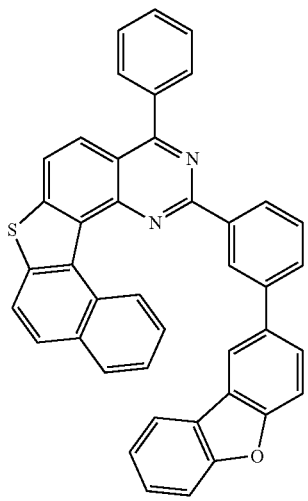

C97
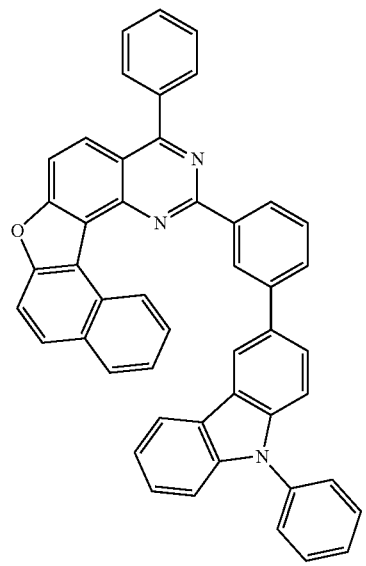
C98
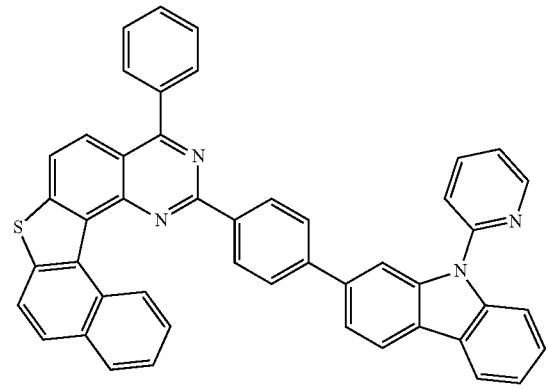
C99
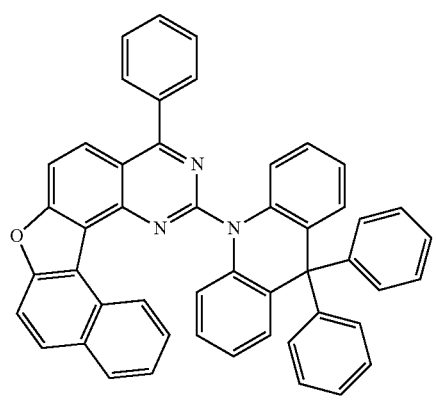
C100
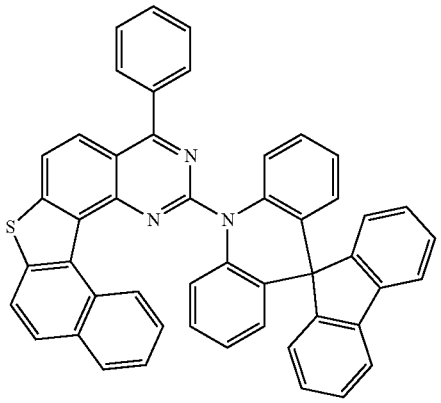
C101
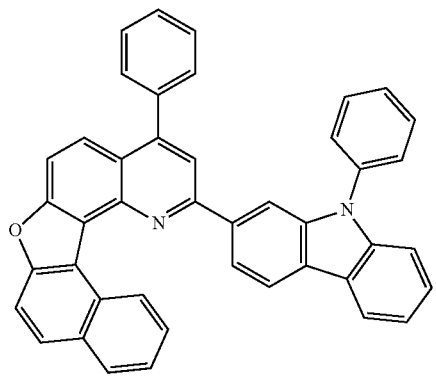
C102
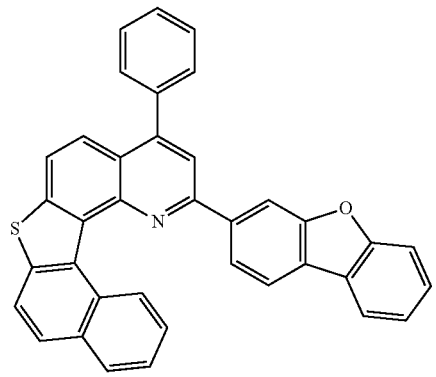
C103
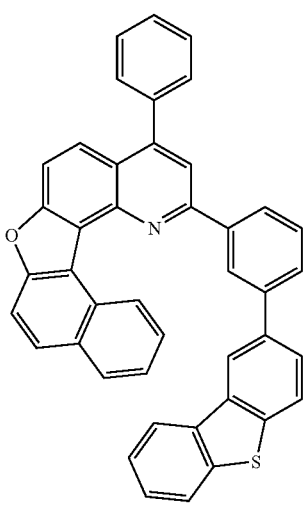

C104
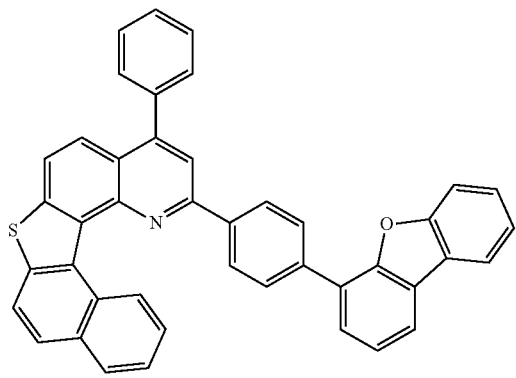
C108
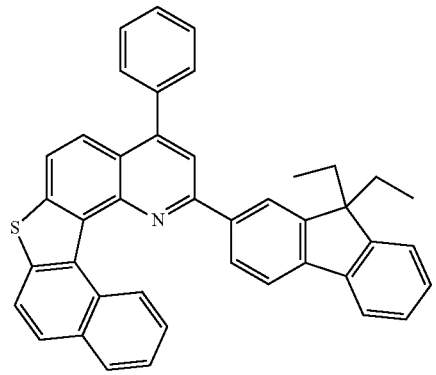
C105
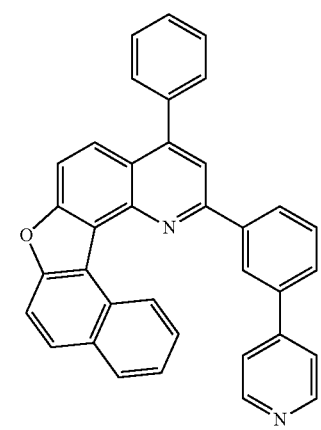
C109
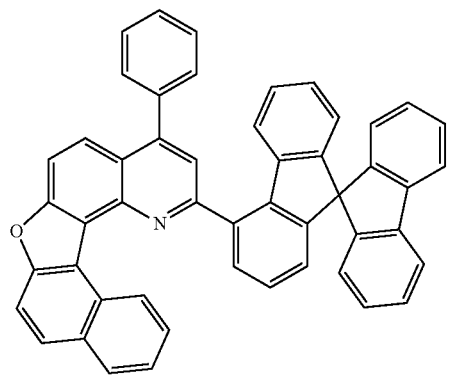
C106
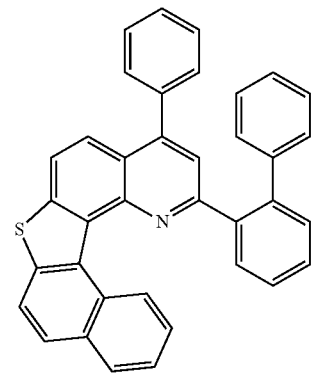
C110
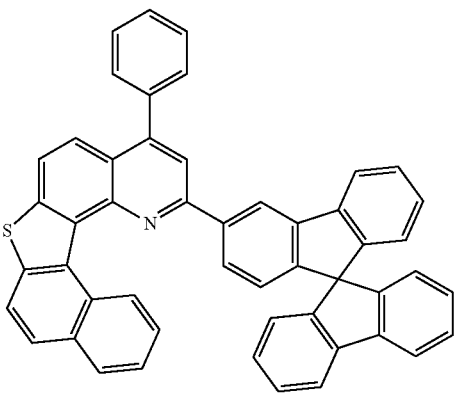
C107
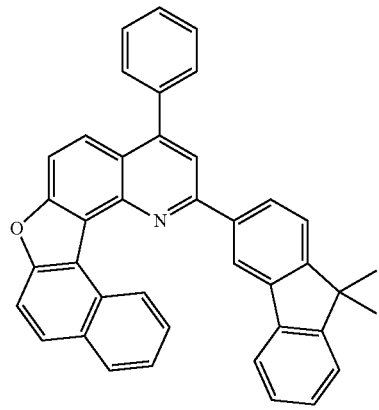
C111
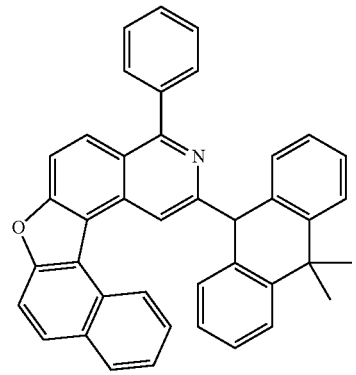

167
-continued
C112
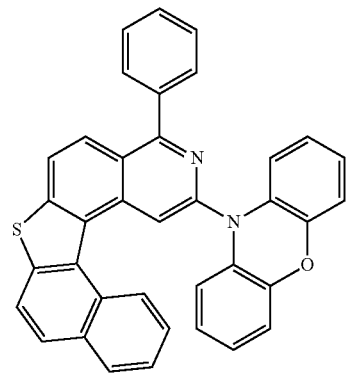
C113
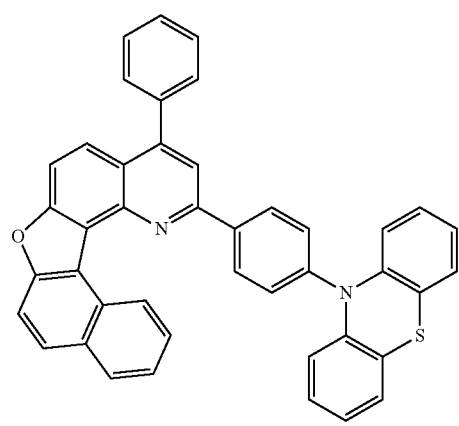
C114
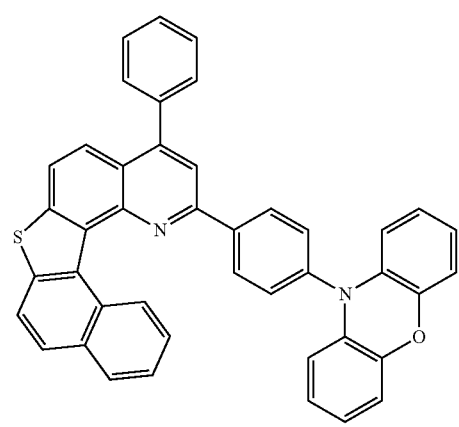
168
-continued
C115
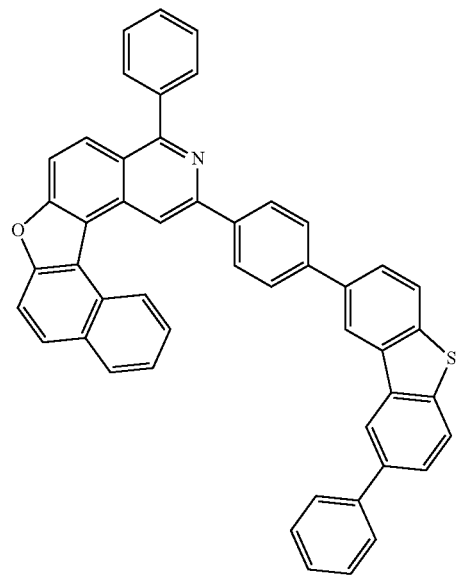
C116
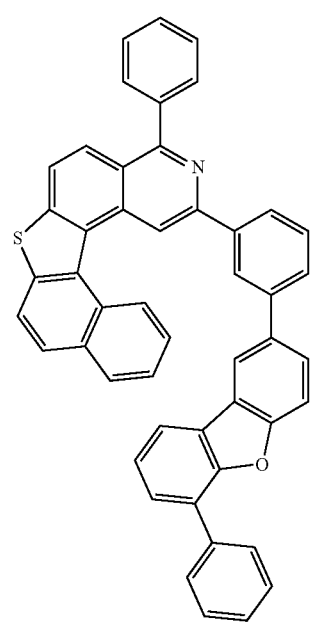
C117
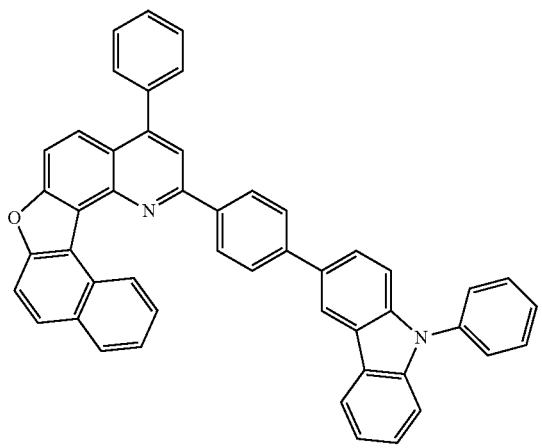

C118
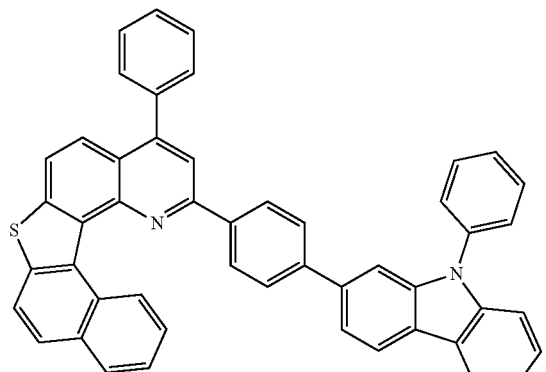
C119
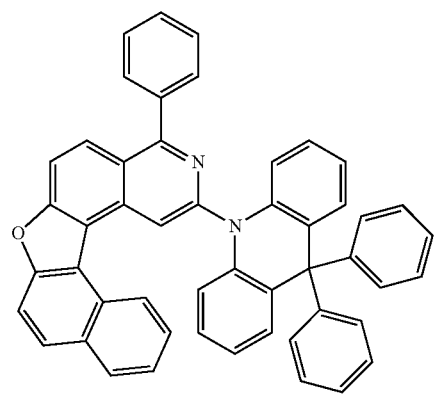
C120
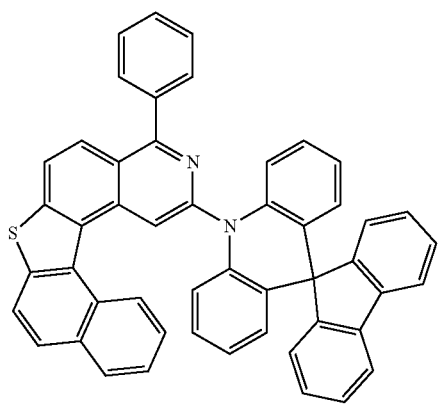
C121
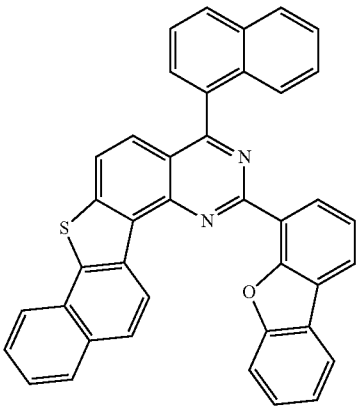
C122
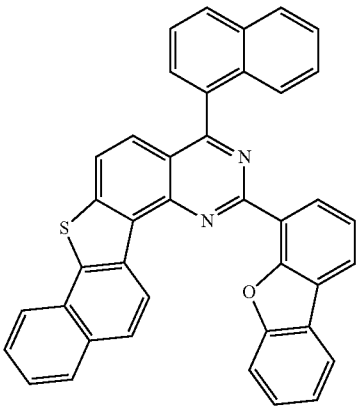
C123
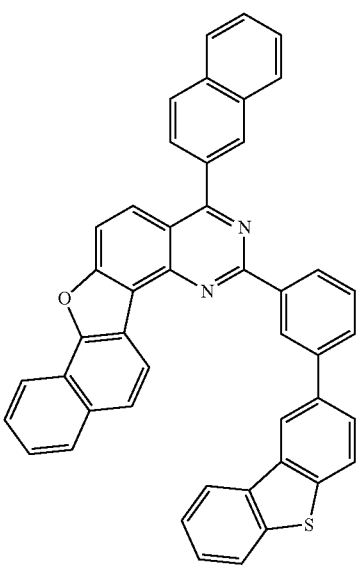
C124
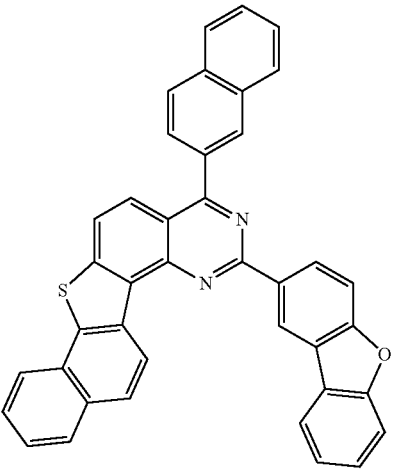

-continued
C125
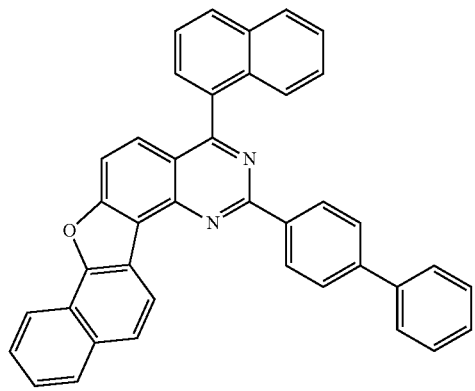
C126
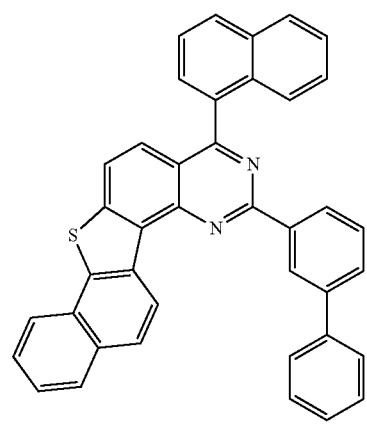
C127
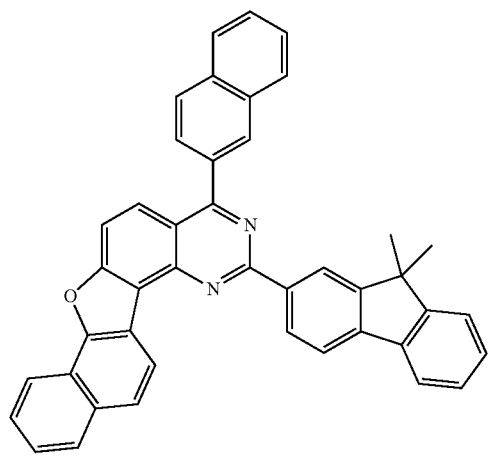
-continued
C128
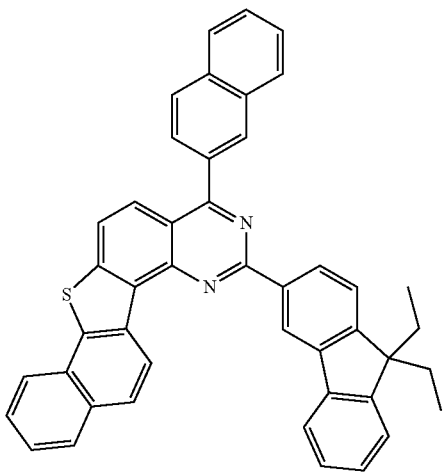
C129
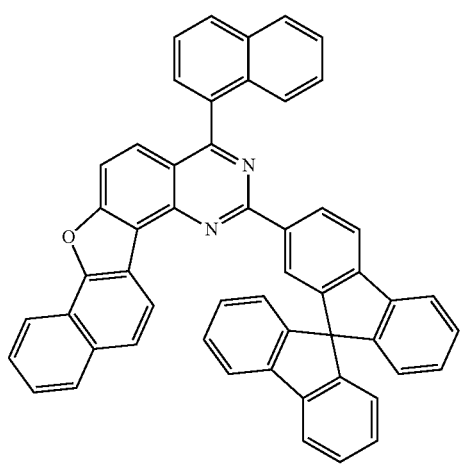
C130
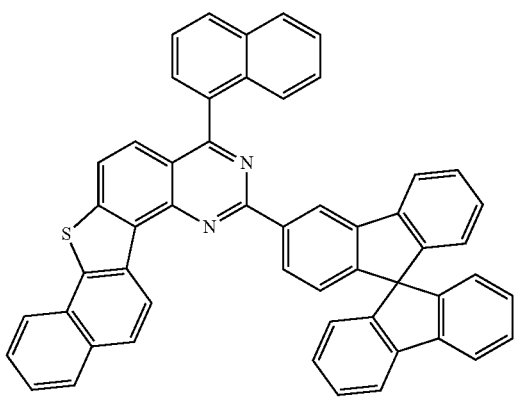

C131
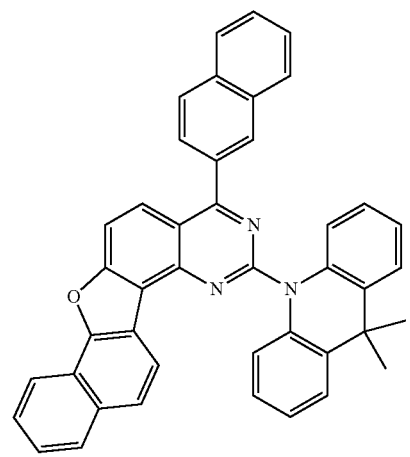
C132
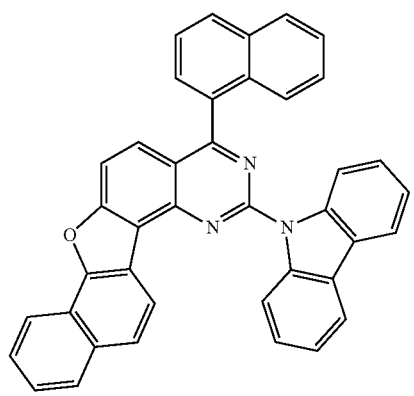
C134
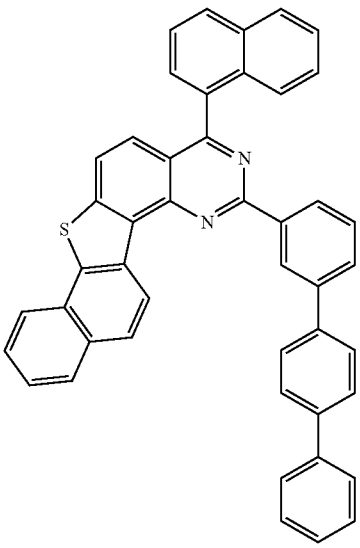
C135
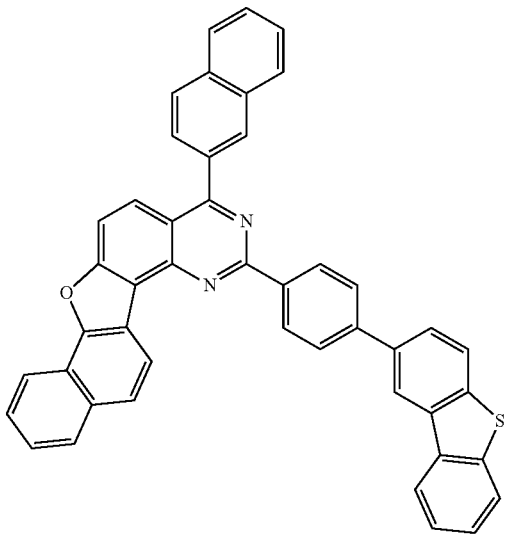
C133
C136
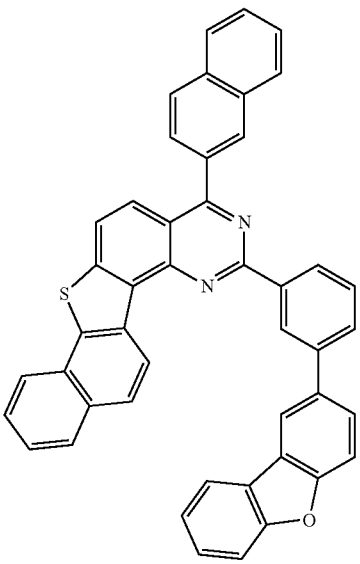

C137
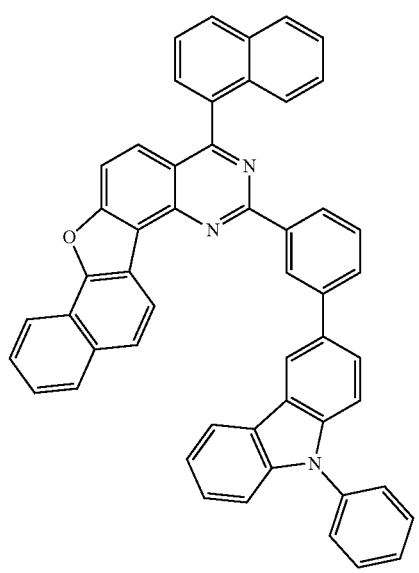
C140
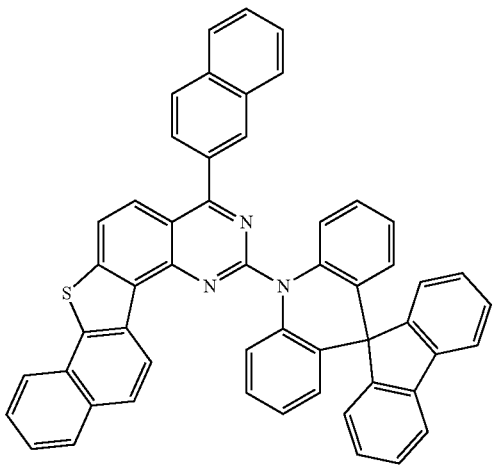
C138
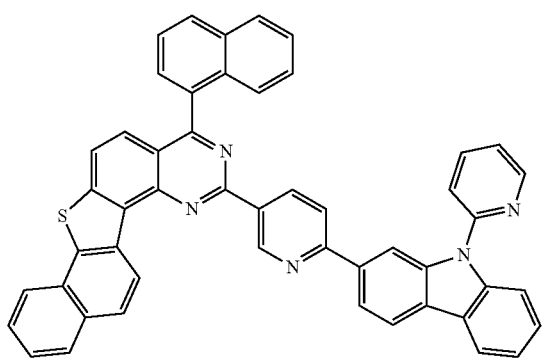
C141
C139
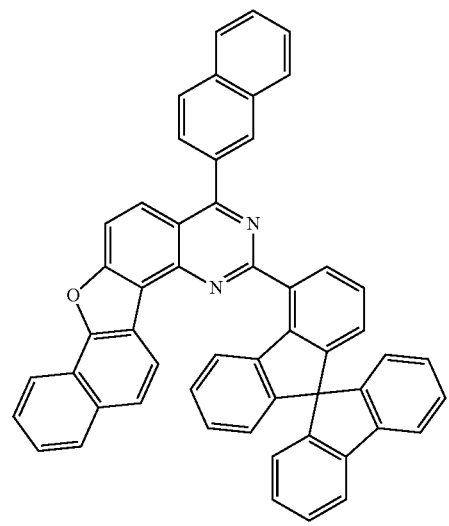
C142
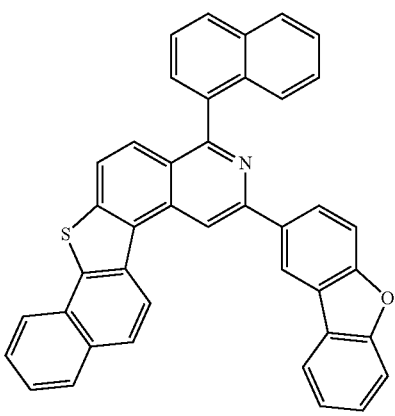

C143
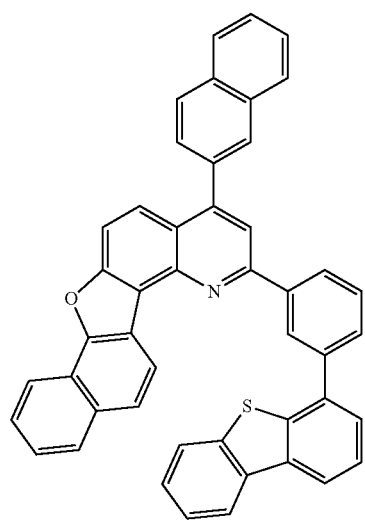
C144
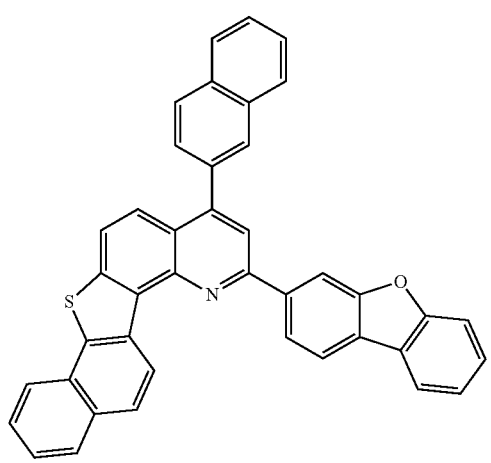
C145
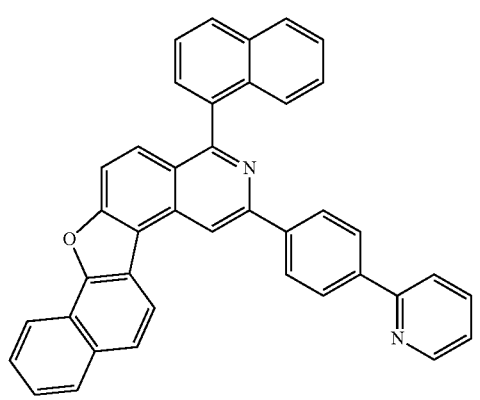
C146
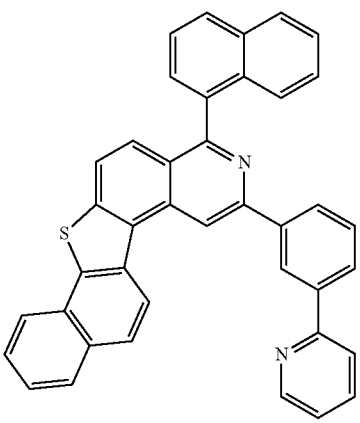
C147
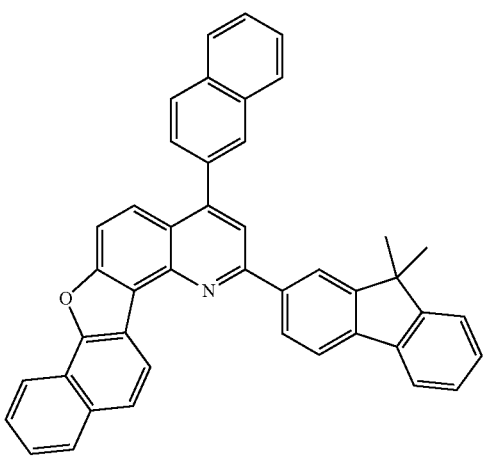
C148
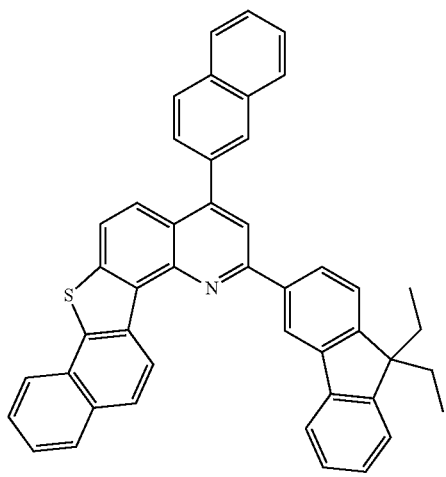

C149
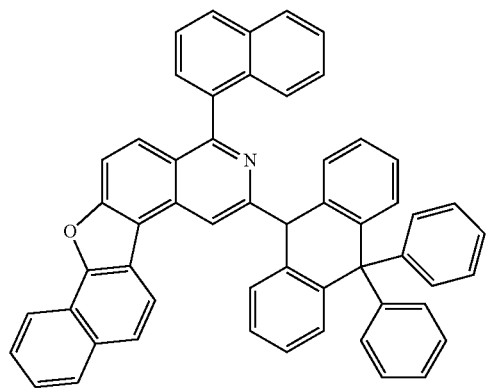
C150
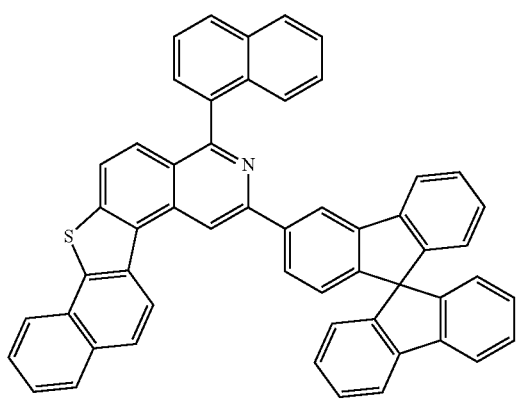
C151
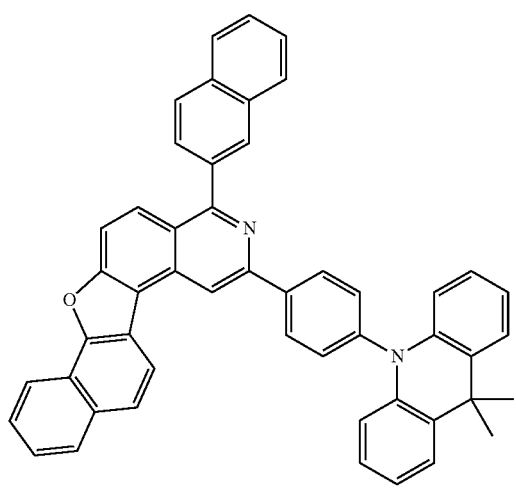
C152
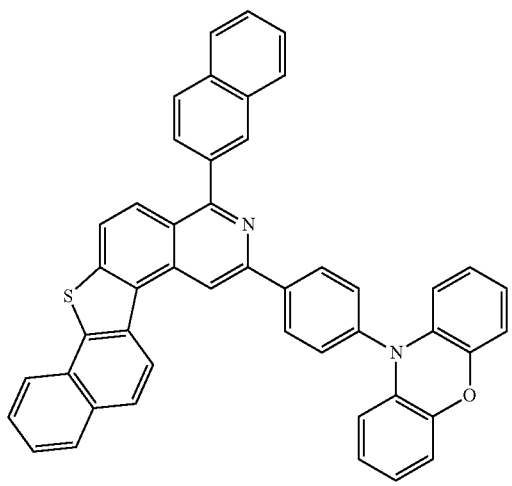
C153
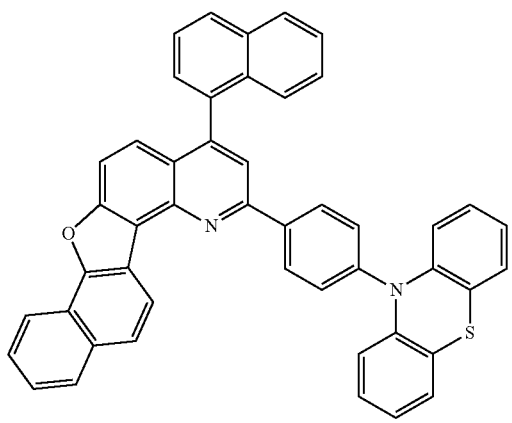
C154
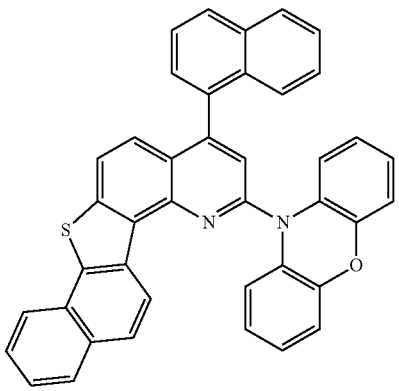

C155
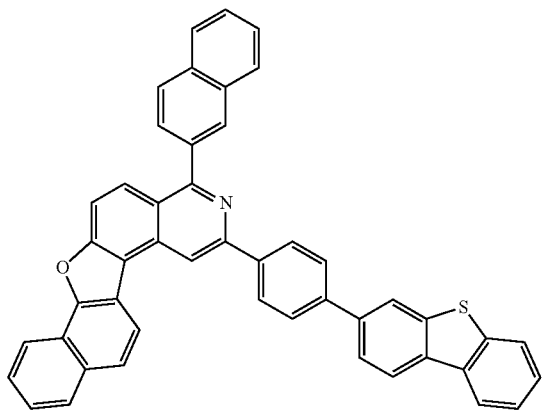
C156
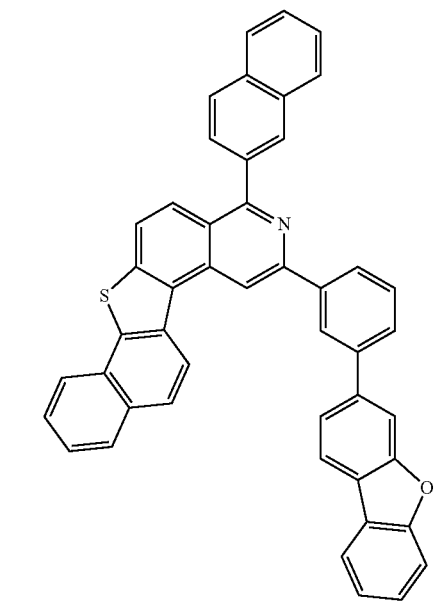
C157
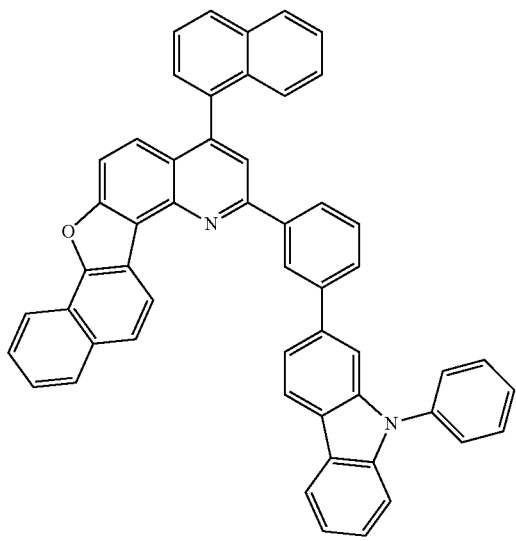
C158
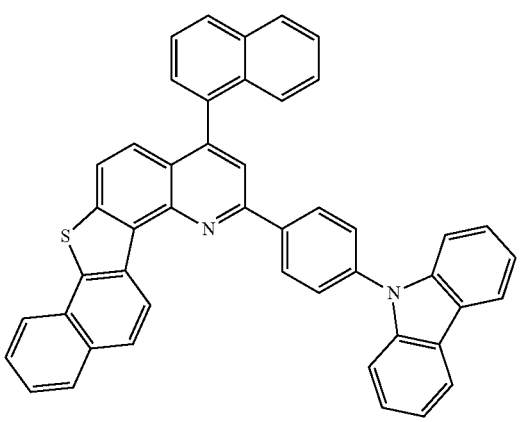
C159
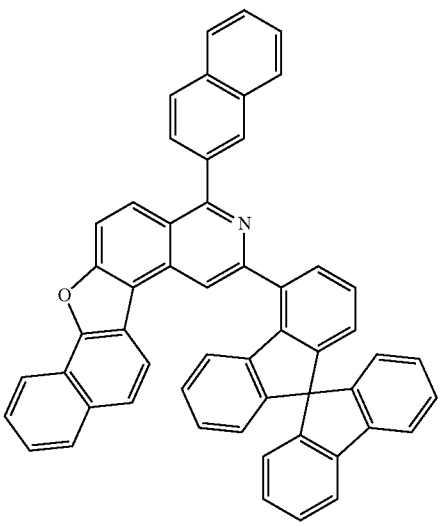
C160
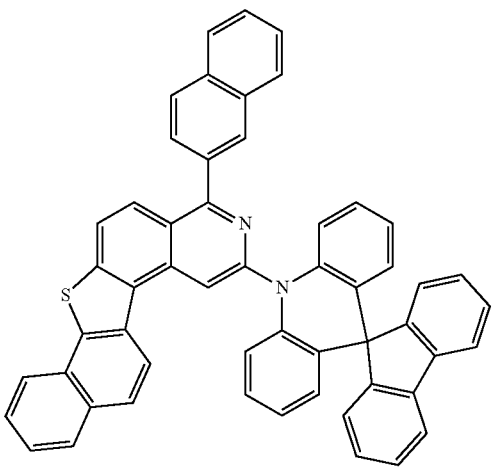

-continued
C161
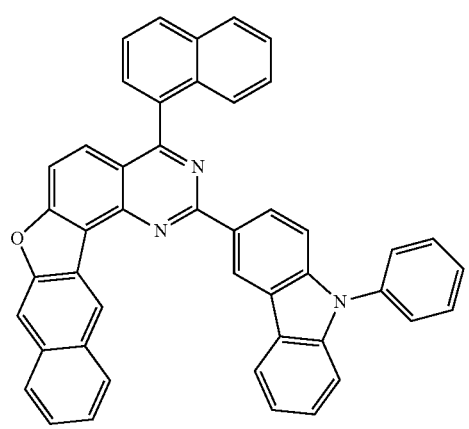
C162
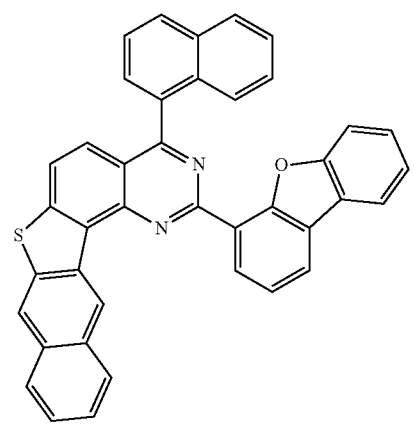
C163
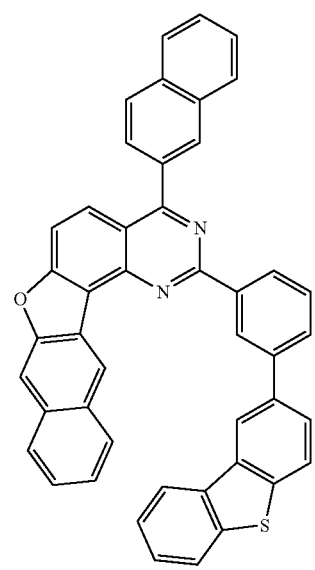
-continued
C164
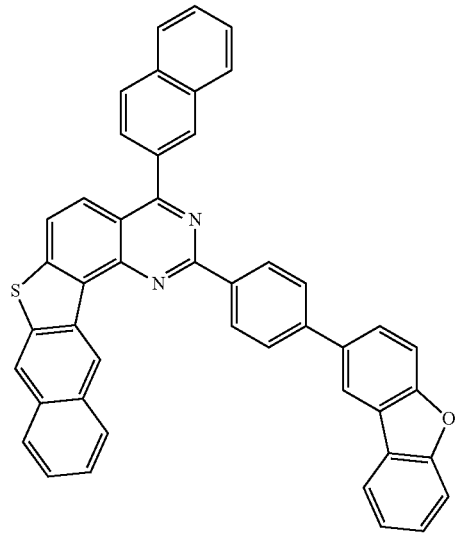
C165
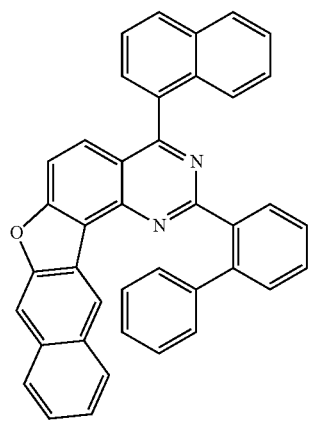
C166
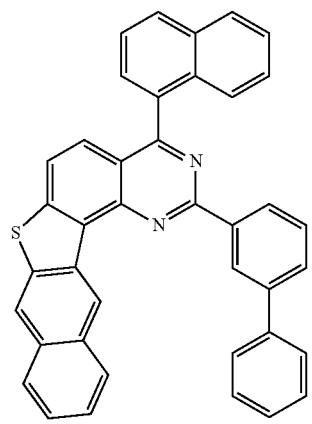

C167
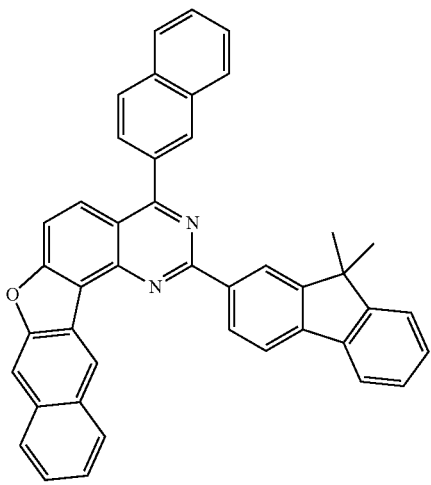
C168
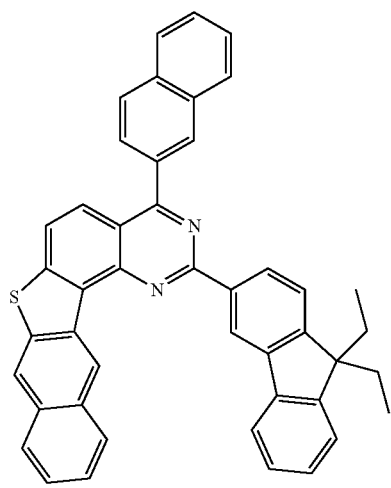
C169
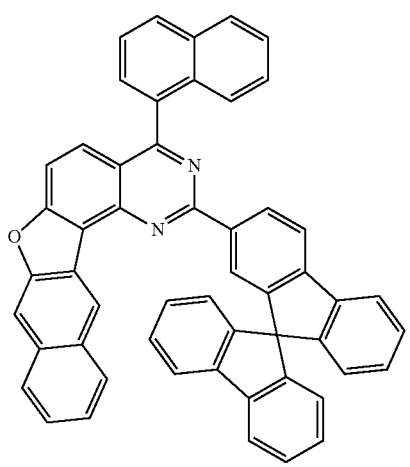
C170
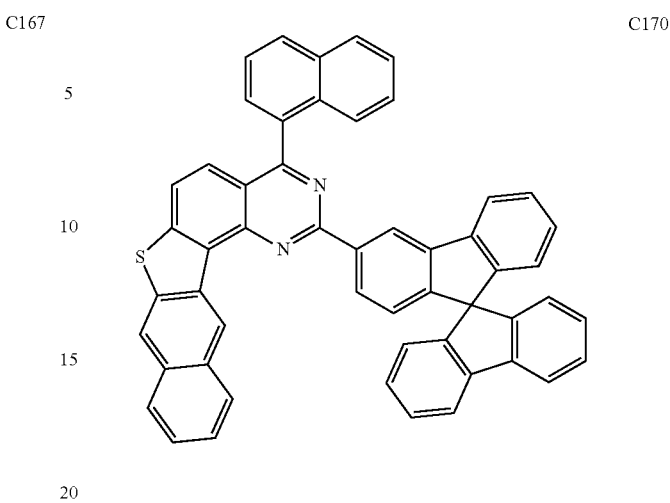
C171
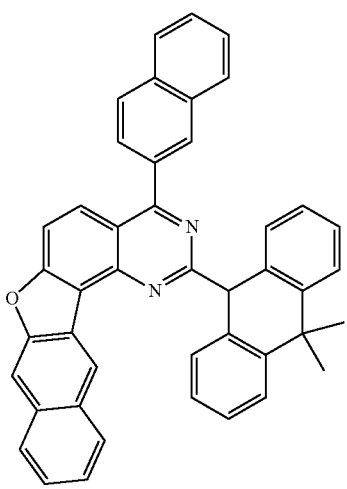
C172
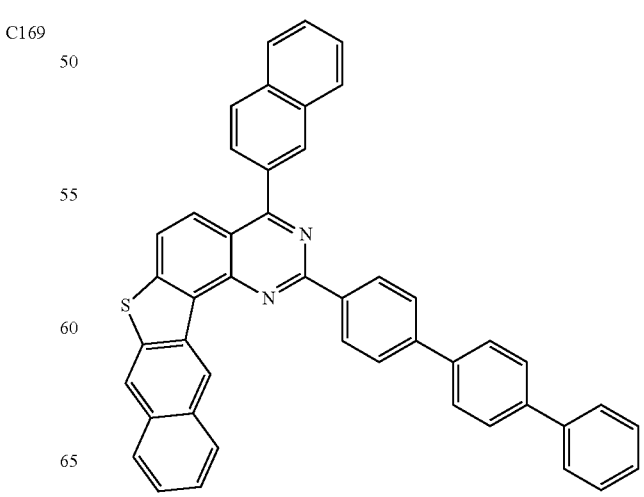

C173
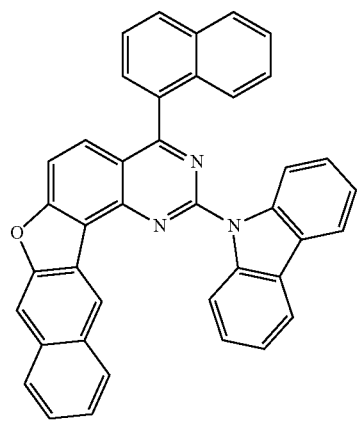
C174
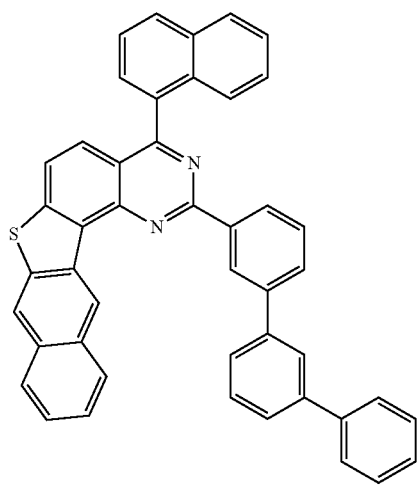
C175
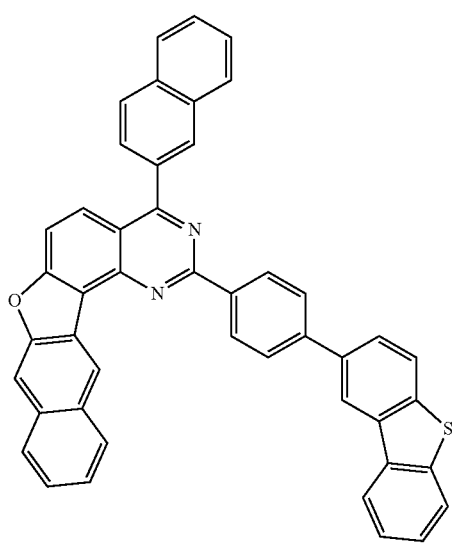
C176
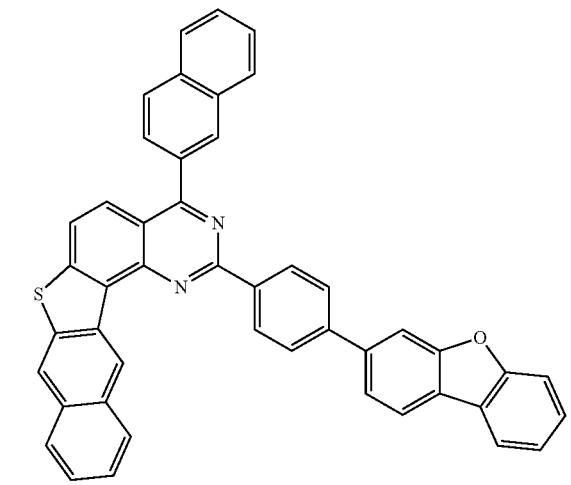
C177
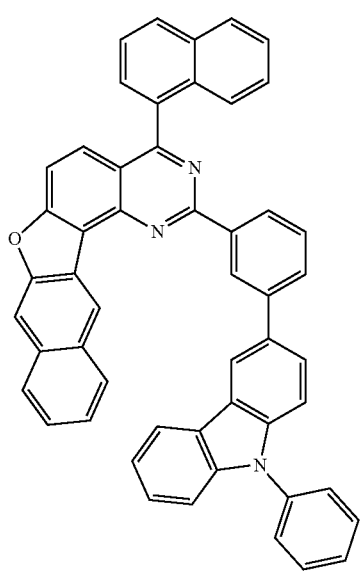
C178
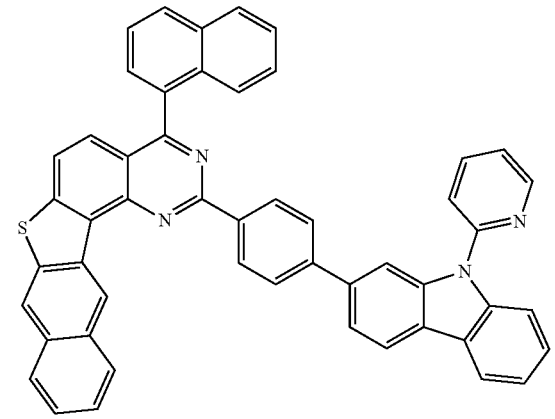

C179
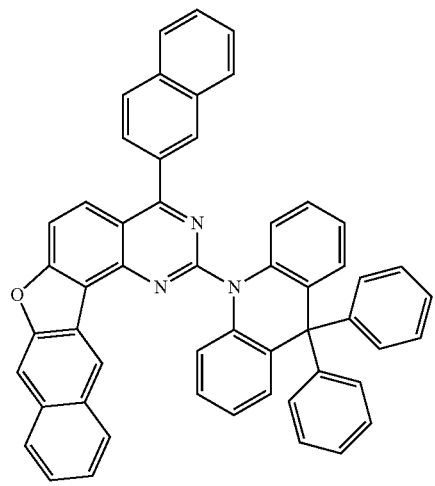
C180
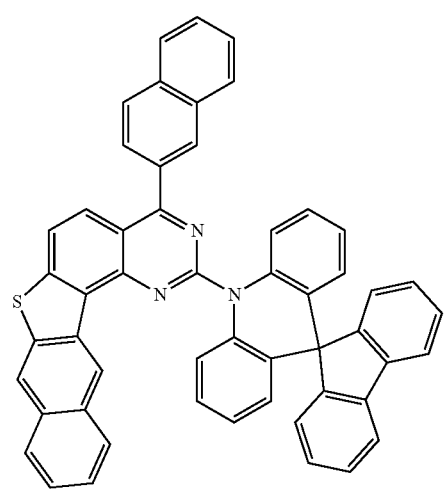
C181
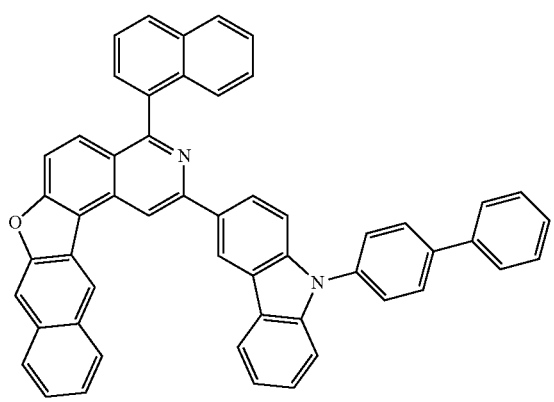
C182
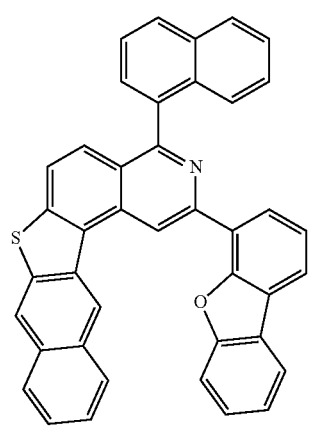
C183
C184
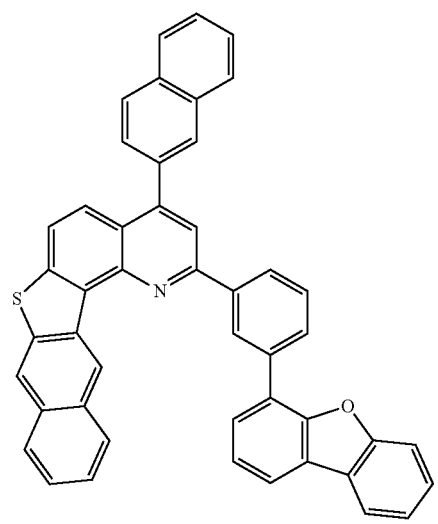

C185
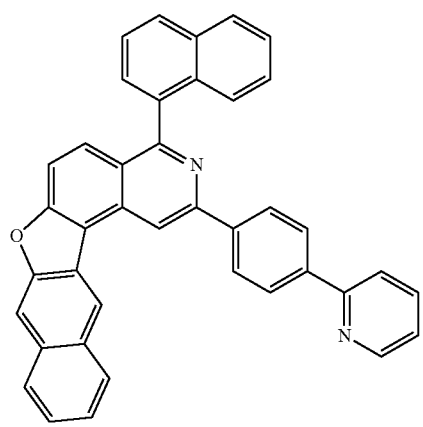
C186
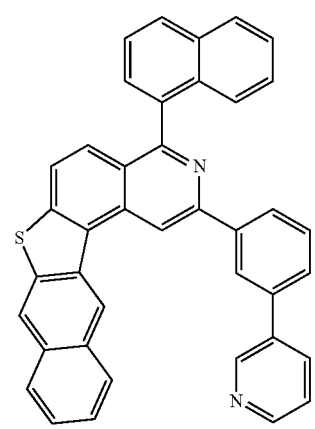
C187
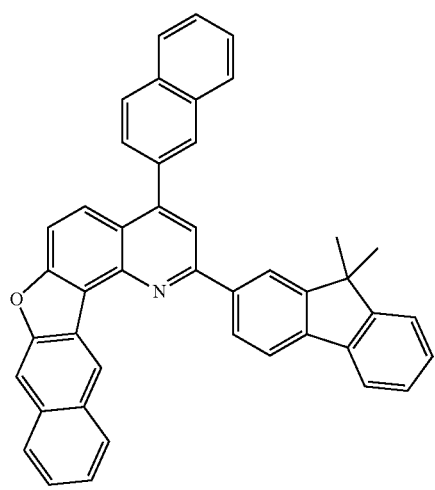
C188
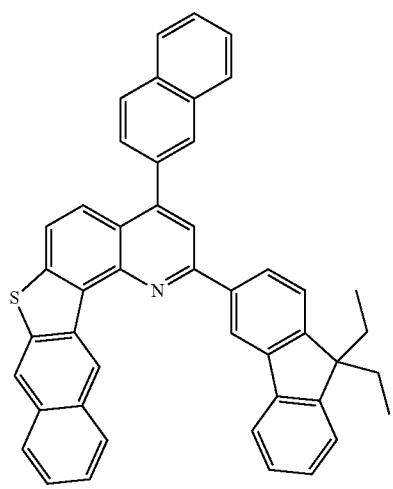
C189
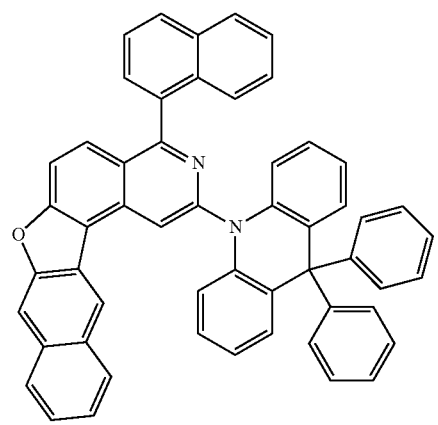
C190
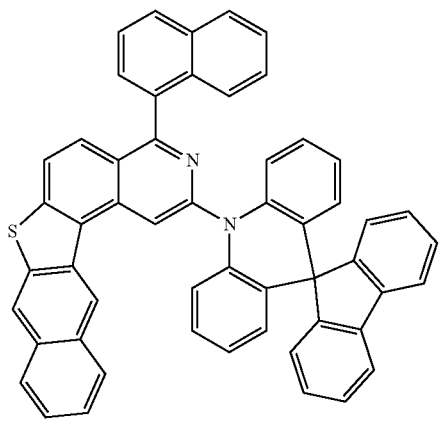

-continued
C191
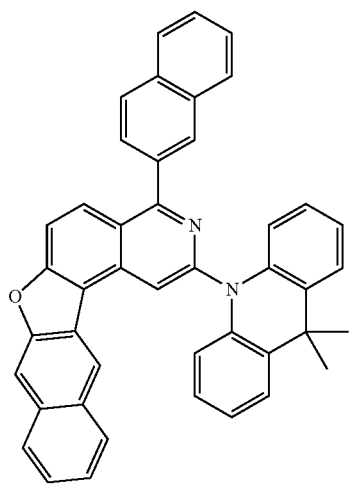
C192
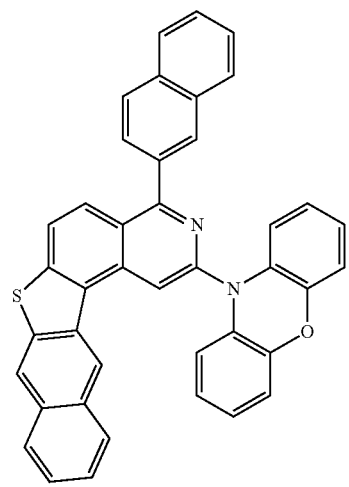
C193
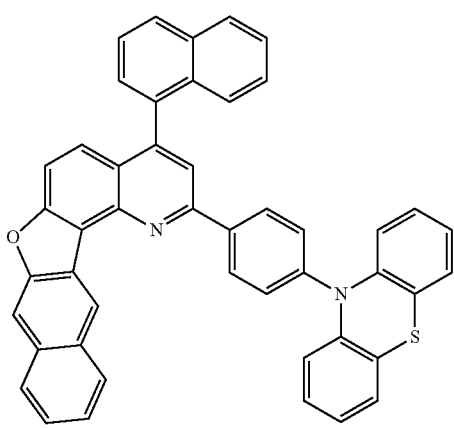
-continued
C194
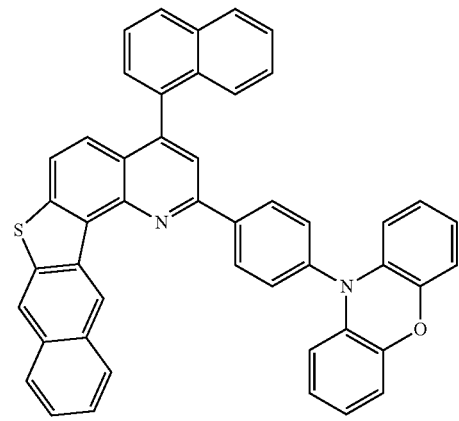
C195
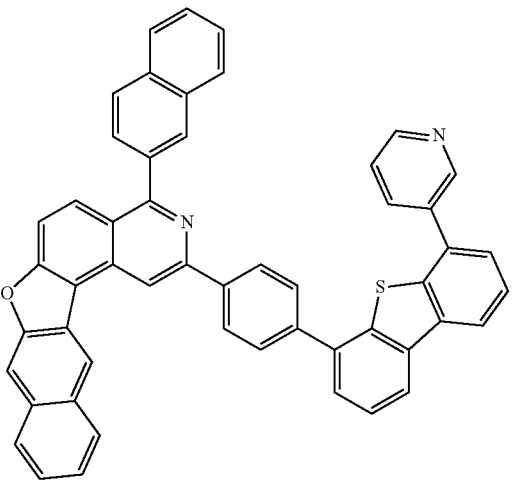
C196
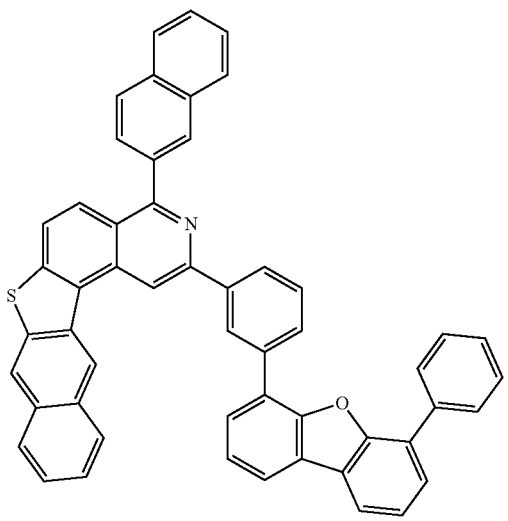

C197
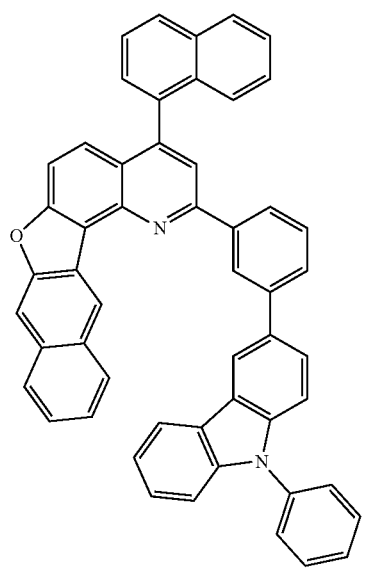
C198
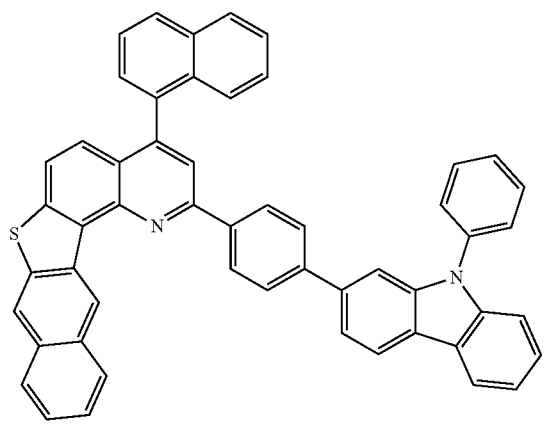
C199
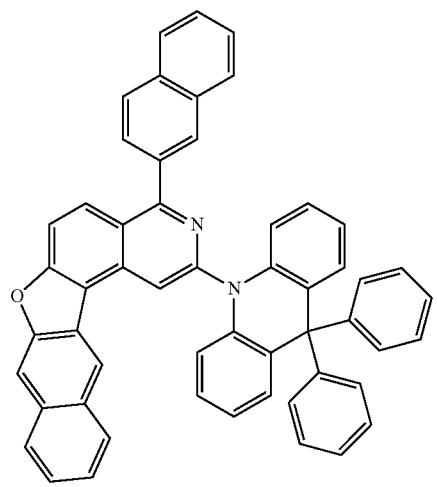
C200
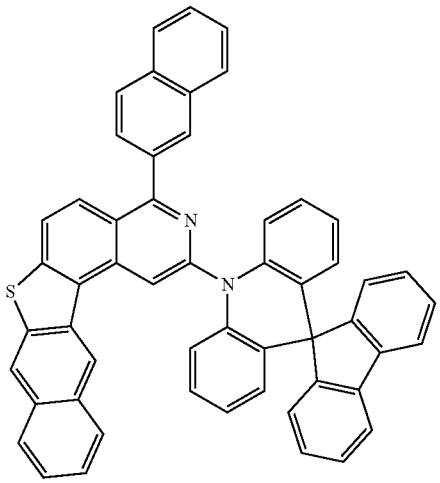
C201
C202
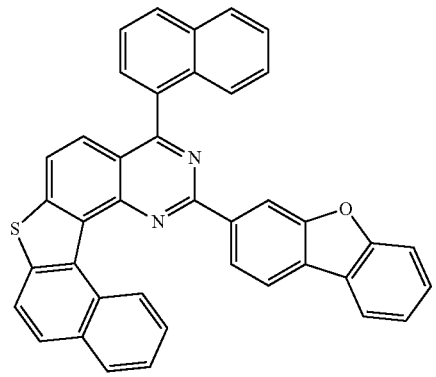

C203
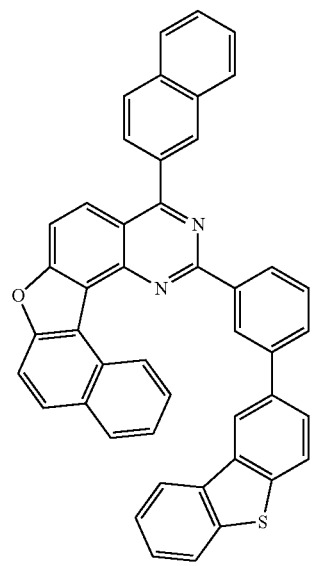
C204
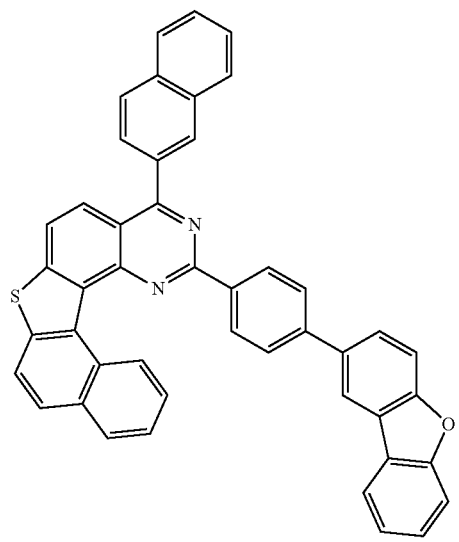
C205
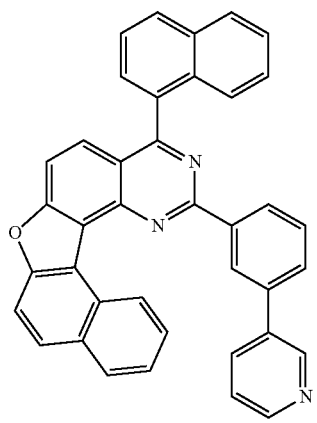
C206
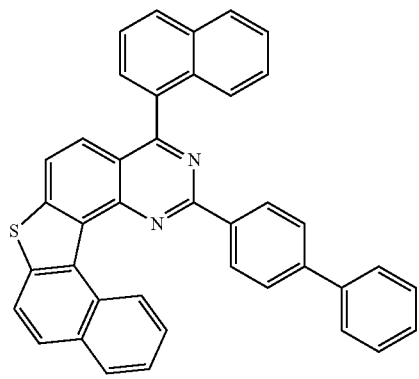
C207
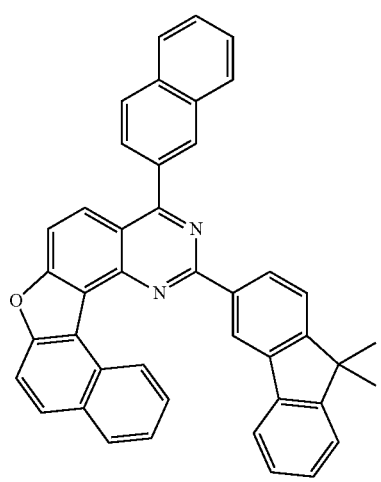
C208
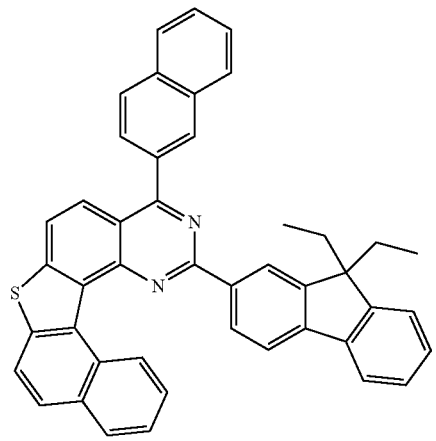

-continued
C209
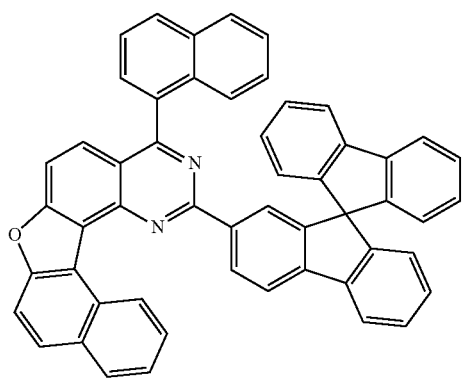
C210
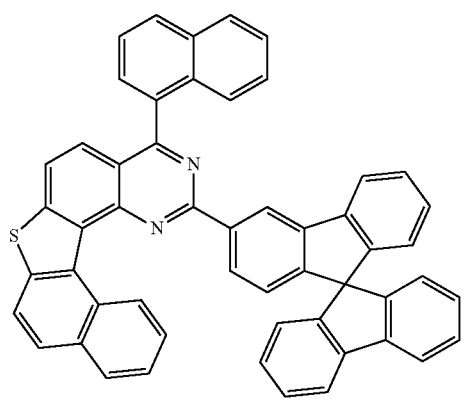
C211
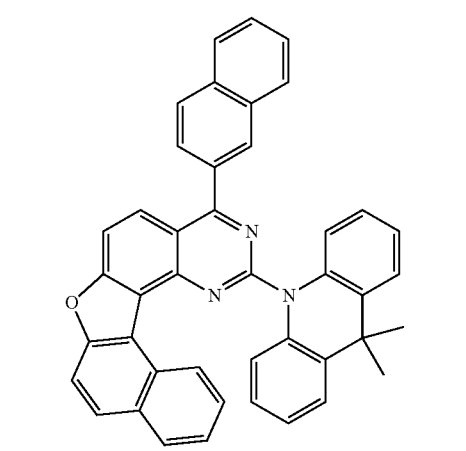
C212
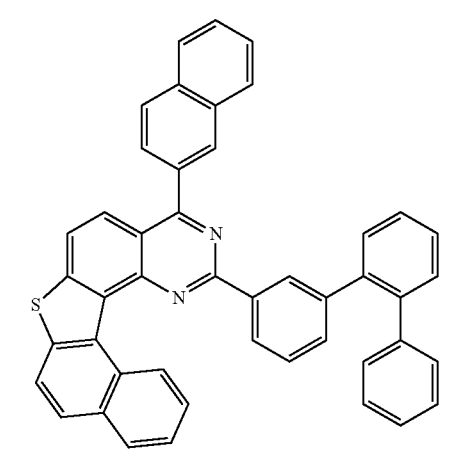
-continued
C213
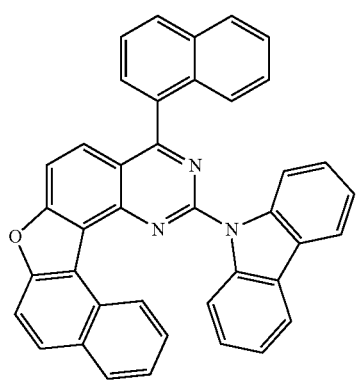
C214
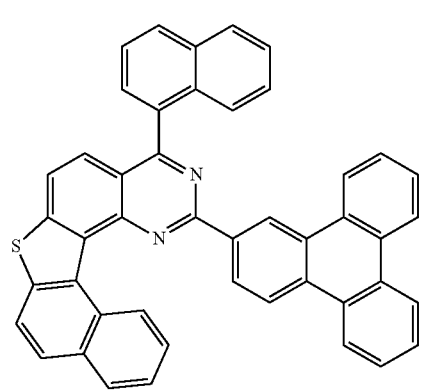
C215
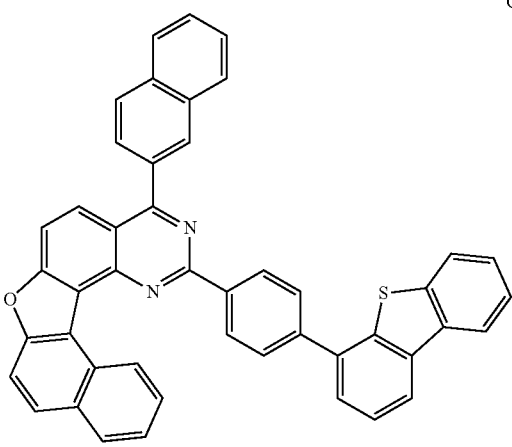
C216
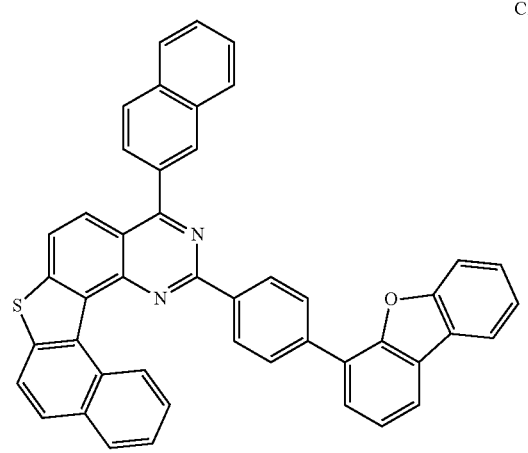

201
-continued
C217
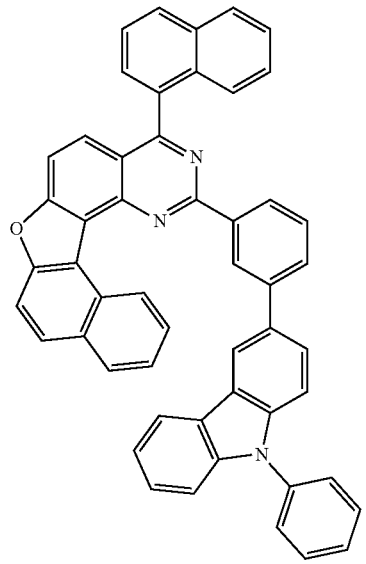
C218
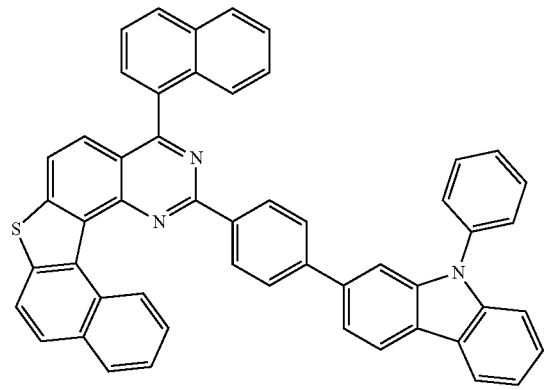
C219
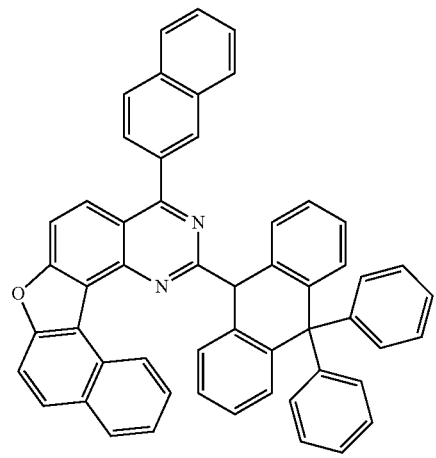
202
-continued
C220
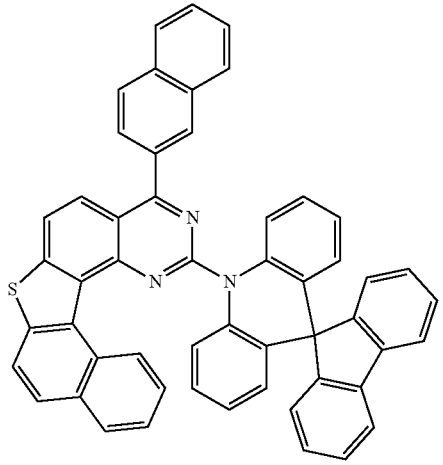
C221
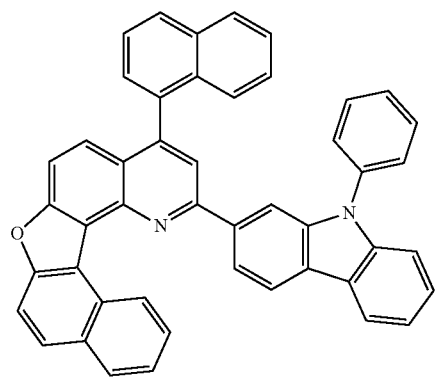
C222
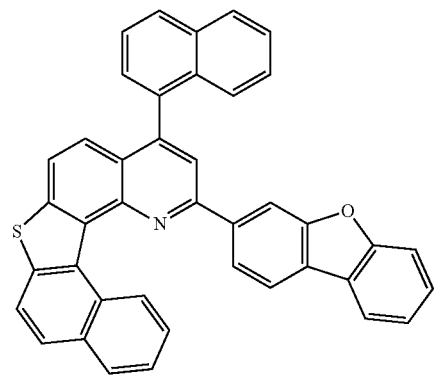

C223
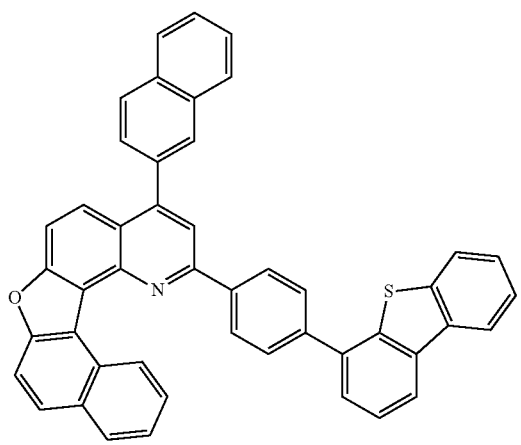
C224
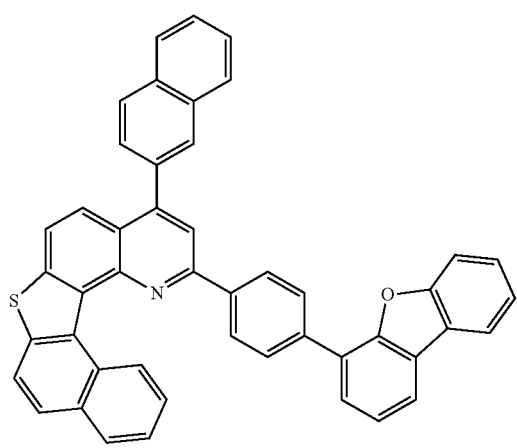
C225
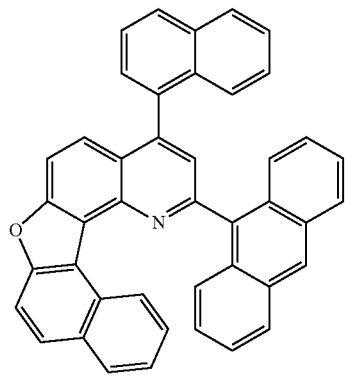
C226
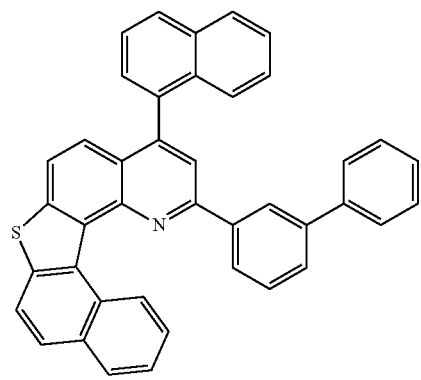
C227
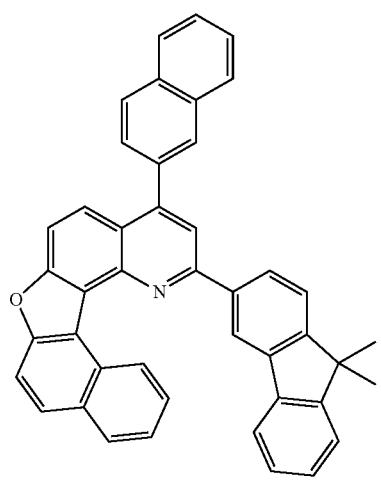
C228
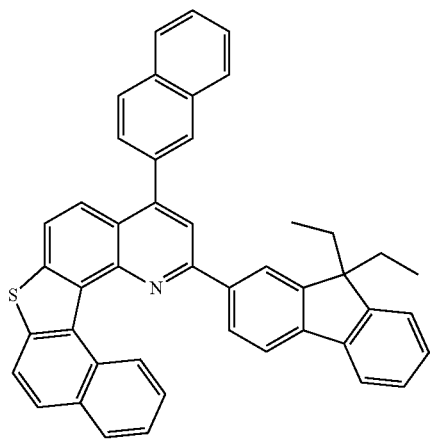

C229
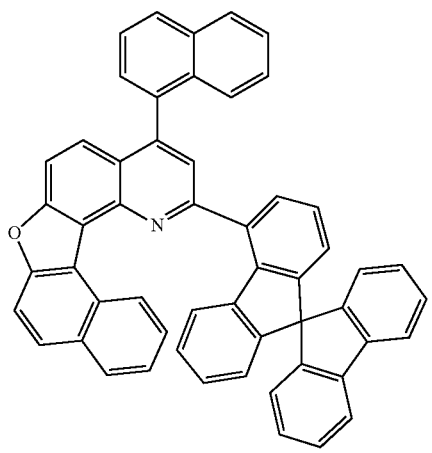
C232
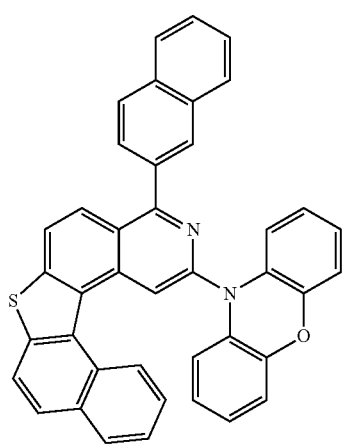
C230
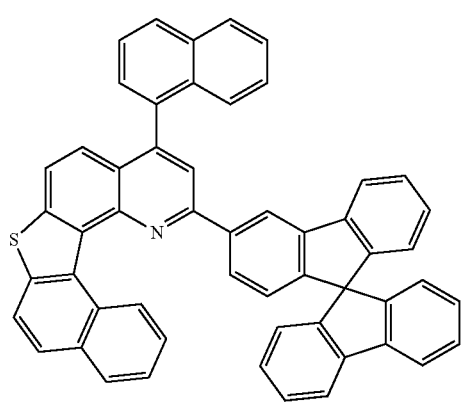
C233
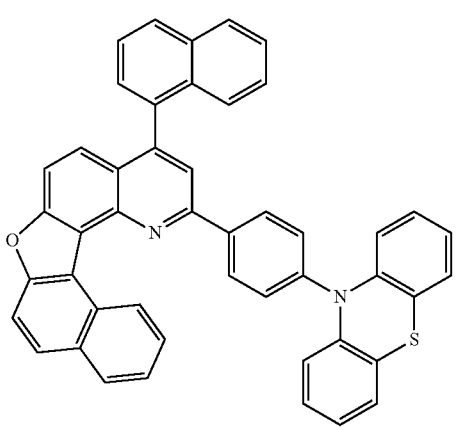
C231
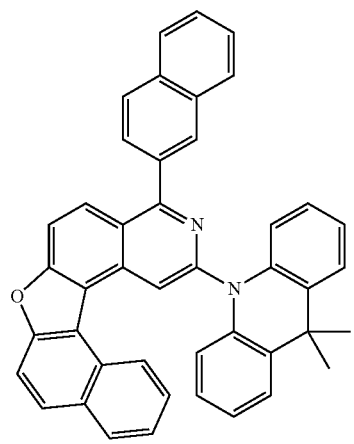
C234
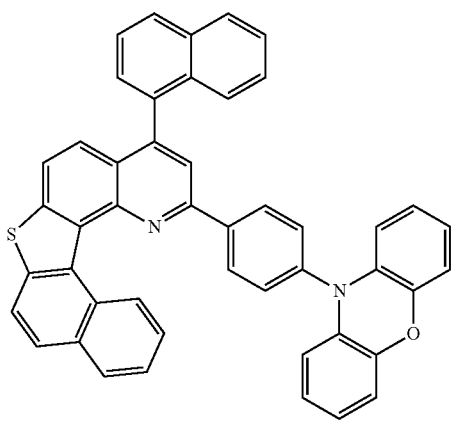

C235

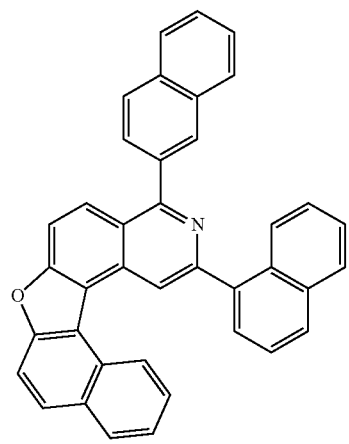

C236

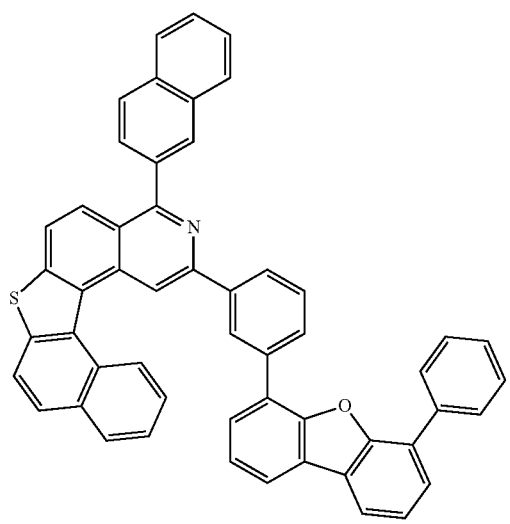

C237

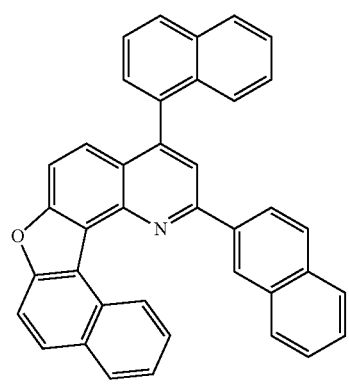

C238

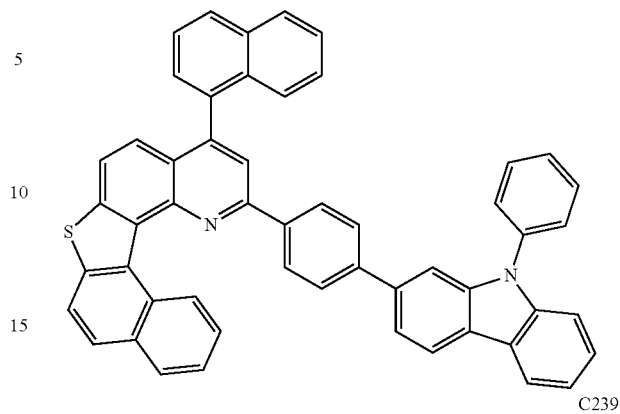

C239

C240

6. An organic electroluminescence device comprising a pair of electrodes having a cathode and an anode, and between the pair of electrodes comprising at least a light emitting layer and one or more layers of organic thin film layers, wherein the light emitting layer and/or the one or more thin film layers comprise the organic compound according to claim 1.

7. The organic electroluminescence device of claim 6, wherein the light emitting layer comprises the compound of formula (A) as a dopant material.

8. The organic electroluminescence device of claim 6, wherein the organic electroluminescence device is a lighting panel.

9. The organic electroluminescence device of claim 6, wherein the organic electroluminescence device is a backlight panel.

\* \* \* \* \*